(12) United States Patent
Sulzer-Mosse et al.

(10) Patent No.: US 8,557,821 B2
(45) Date of Patent: Oct. 15, 2013

(54) MICROBIOCIDAL HETEROCYCLES

(75) Inventors: Sarah Sulzer-Mosse, Stein (CH); Clemens Lamberth, Stein (CH); Mathias Stephan Respondek, Stein (CH); Laura Quaranta, Stein (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 0 days.

(21) Appl. No.: 13/390,036

(22) PCT Filed: Aug. 5, 2010

(86) PCT No.: PCT/EP2010/061381
§ 371 (c)(1),
(2), (4) Date: Feb. 10, 2012

(87) PCT Pub. No.: WO2011/018401
PCT Pub. Date: Feb. 17, 2011

(65) Prior Publication Data
US 2012/0142700 A1    Jun. 7, 2012

(30) Foreign Application Priority Data
Aug. 12, 2009 (EP) .................................. 09167736

(51) Int. Cl.
*A61K 31/497*   (2006.01)
*A61K 31/454*   (2006.01)
*C07D 403/04*   (2006.01)
*C07D 401/04*   (2006.01)

(52) U.S. Cl.
USPC ....... 514/252.14; 514/326; 544/370; 546/209

(58) Field of Classification Search
USPC ............... 544/370; 546/209; 514/252.14, 326
See application file for complete search history.

(56) References Cited

FOREIGN PATENT DOCUMENTS

| WO | 2007/014290 | 2/2007 |
|----|-------------|--------|
| WO | 2009/094445 | 7/2009 |

OTHER PUBLICATIONS

Patani G A et al: "Bioisosterism: A Rational Approach in Drug Design" Chemical Reviews, ACS, Washington, DC, US, 1996.

*Primary Examiner* — Yong Chu
*Assistant Examiner* — Karen Cheng
(74) *Attorney, Agent, or Firm* — R. Kody Jones

(57) ABSTRACT

The present invention relates to heterocyclic compounds of formula (I) which have microbiocidal activity, in particular fungicidal activity, as well as methods of using the compounds of formula (I) to control microbes.

(I)

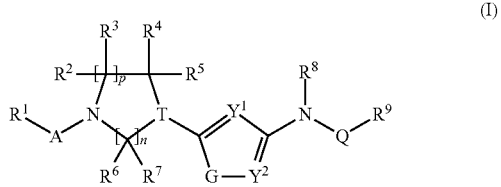

15 Claims, No Drawings

MICROBIOCIDAL HETEROCYCLES

This application is a 371 of International Application No. PCT/EP2010/061381 filed Aug. 5, 2010, which claims priority to EP 09167736.9 filed Aug. 12, 2009, the contents of which are incorporated herein by reference.

The present invention relates to heterocycles, e.g. as active ingredients, which have microbiocidal activity, in particular fungicidal activity. The invention also relates to preparation of these heterocycles, to heterocyclic derivatives used as intermediates in the preparation of these heterocycles, to preparation of these intermediates, to agrochemical compositions which comprise at least one of the heterocycles, to preparation of these compositions and to use of the heterocycles or compositions in agriculture or horticulture for controlling or preventing infestation of plants, harvested food crops, seeds or non-living materials by phytopathogenic microorganisms, preferably fungi.

Certain heterocycles for use as fungicides are described in WO 2007/014290, WO 2008/013622, WO 2008/013925, WO 2008/091580, WO 2008/091594 and WO 2009/055514.

The present invention provides compounds of formula I:

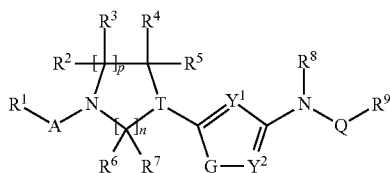

(I)

wherein

A is x-C(=O)—, x-C(=S)—, x-C($R^{10}R^{11}$)—C(=O)—, x-C($R^{12}R^{13}$)—C(=S)—, x-O—C(=O)—, x-O—C(=S)—, x-N($R^{14}$)—C(=O)—, x-N($R^{15}$)—C(=S)—, x-C($R^{16}R^{17}$)—SO$_2$— or x-N=C($R^{26}$)—, in each case x indicates the bond that is connected to $R^1$;

T is $CR^{18}$ or N;

G is O or S;

$Y^1$ and $Y^2$ are independently $CR^{19}$ or N;

Q is —C(=O)-z, —C(=S)-z, —C(=O)—O-z, —C(=S)—O-z, —C(=O)—N($R^{20}$)-z, —C(=S)—N($R^{21}$)-z or —SO$_2$-z-, in each case z indicates the bond that is connected to $R^9$;

n is 1 or 2;

p is 1 or 2, providing that when n is 2, p is 1;

$R^1$ is phenyl, pyridyl, imidazolyl, or pyrazolyl; wherein the phenyl, pyridyl, imidazolyl and pyrazolyl are each optionally substituted by 1 to 3 substituents independently selected from $C_1$-$C_4$ alkyl, $C_1$-$C_4$ haloalkyl, halogen, cyano, hydroxy and amino;

$R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$, $R^{19}$ and $R^{26}$ each independently are hydrogen, halogen, cyano, $C_1$-$C_4$alkyl or $C_1$-$C_4$haloalkyl;

$R^8$, $R^{14}$, $R^{15}$, $R^{20}$ and $R^{21}$ each independently are hydrogen, $C_1$-$C_4$alkyl or $C_1$-$C_4$alkoxy; and $R^9$ is phenyl, benzyl or group (a):

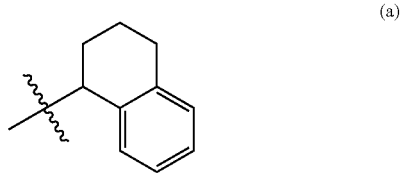 [SMILES: *C1CCCc2ccccc21]

(a)

wherein the phenyl, benzyl and group (a) are each optionally substituted with 1 to 3 substituents independently selected from $C_1$-$C_4$ alkyl, $C_1$-$C_4$ haloalkyl, $C_1$-$C_4$ alkoxy, $C_1$-$C_4$ haloalkoxy, halogen, cyano, hydroxyl, $N(R^{27})_2$, SH, $C_1$-$C_4$ alkylthio, nitro, phenylsulfonyl and phenylsulfinyl, wherein the phenylsulfonyl and phenylsulfinyl are optionally substituted by 1 to 3 substituents independently selected from $C_1$-$C_4$ alkyl, $C_1$-$C_4$ haloalkyl, $C_1$-$C_4$ alkoxy, $C_1$-$C_4$ haloalkoxy, halogen and cyano;

each $R^{27}$ independently is hydrogen, $C_1$-$C_4$ alkyl, phenylsulfonyl or phenylsulfinyl, wherein the phenylsulfonyl and phenylsulfinyl are optionally substituted by 1 to 3 substituents independently selected from $C_1$-$C_4$ alkyl, $C_1$-$C_4$ haloalkyl, $C_1$-$C_4$ alkoxy, $C_1$-$C_4$ haloalkoxy, halogen and cyano; or a salt or a N-oxide thereof.

Where substituents are indicated as being optionally substituted, this means that they may or may not carry one or more identical or different substituents. Normally not more than three such optional substituents are present at the same time.

The term "halogen" refers to fluorine, chlorine, bromine or iodine, preferably fluorine, chlorine or bromine.

The term "amino" refers to —NH$_2$.

Alkyl substituents may be straight-chained or branched. Alkyl on its own or as part of another substituent is, depending upon the number of carbon atoms mentioned, for example, methyl, ethyl, n-propyl, n-butyl, n-pentyl, n-hexyl and the isomers thereof, for example, iso-propyl, iso-butyl, sec-butyl, tert-butyl, iso-amyl or pivaloyl.

A haloalkyl group may contain one or more identical or different halogen atoms and, for example, may stand for CH$_2$Cl, CHCl$_2$, CCl$_3$, CH$_2$F, CHF$_2$, CF$_3$, CF$_3$CH$_2$, CH$_3$CF$_2$, CF$_3$CF$_2$ or CCl$_3$CCl$_2$.

The presence of one or more possible asymmetric carbon atoms in a compound of formula I means that the compounds may occur in optically isomeric forms, i.e. enantiomeric or diastereomeric forms. As a result of the presence of a possible aliphatic C=C double bond, geometric isomerism may occur, i.e. cis-trans or (E)-(Z) isomerism. Also atropisomers may occur as a result of restricted rotation about a single bond. Formula I is intended to include all those possible isomeric forms and mixtures thereof. The present invention includes all those possible isomeric forms and mixtures thereof for a compound of formula I. Likewise, formula I is intended to include all possible tautomers. The present invention includes all possible tautomeric forms for a compound of formula I.

In each case, the compounds of formula I according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Suitable salts of the compounds of formula I include those resulting after addition of acid such as those with an inorganic mineral acid e.g. hydrochloric, hydrobromic, sulphuric, nitric or phosphoric acid, or an organic carboxylic acid e.g. oxalic, tartaric, lactic, butyric, toluic, hexanoic or phthalic acid, or a sulfonic acid e.g. methane, benzene or toluene sulfonic acid.

Preferably the compound of formula I is a compound wherein:

A is x-C(=O)—, x-C(=S)—, x-C($R^{10}R^{11}$)—C(=O)—, x-C($R^{12}R^{13}$)—C(=S)—, x-O—C(=O)—, x-O—C(=S)—, x-N($R^{14}$)—C(=O)—, x-N($R^{15}$)—C(=S)— or x-C($R^{16}R^{17}$)—$SO_2$—, in each case x indicates the bond that is connected to $R^1$;

T is $CR^{18}$ or N;

G is O or S;

$Y^1$ and $Y^2$ are independently $CR^{19}$ or N;

Q is —C(=O)-z, —C(=S)-z, —C(=O)—O-z, —C(=S)—O-z, —C(=O)—N($R^{20}$)-z, —C(=S)—N($R^{21}$)-z or —$SO_2$-z-, in each case z indicates the bond that is connected to $R^9$;

n is 1 or 2;

p is 1 or 2, providing that when n is 2, p is 1;

$R^1$ is phenyl, pyridyl, imidazolyl, or pyrazolyl; wherein the phenyl, pyridyl, imidazolyl and pyrazolyl are each optionally substituted by 1 to 3 substituents independently selected from $C_1$-$C_4$ alkyl, $C_1$-$C_4$ haloalkyl, halogen, cyano, hydroxy and amino;

$R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$ and $R^{19}$ each independently are hydrogen, halogen, cyano, $C_1$-$C_4$alkyl, or $C_1$-$C_4$haloalkyl;

$R^8$, $R^{14}$, $R^{15}$, $R^{20}$ and $R^{21}$ each independently are hydrogen or $C_1$-$C_4$alkyl; and $R^9$ is phenyl, benzyl or group (a):

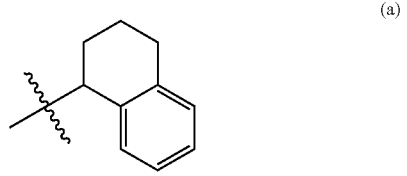

wherein the phenyl, benzyl and group (a) are each optionally substituted with 1 to 3 substituents independently selected from $C_1$-$C_4$ alkyl, $C_1$-$C_4$ haloalkyl, halogen, cyano, hydroxy and amino;

Preferably the compound of formula I is a compound wherein:

A is x-C(=O)—, x-C(=S)—, x-C($R^{10}R^{11}$)—C(=O)—, x-C($R^{12}R^{13}$)—C(=S)—, x-O—C(=O)—, x-O—C(=S)— or x-C($R^{16}R^{17}$)—$SO_2$—, in each case x indicates the bond that is connected to $R^1$;

T is $CR^{18}$ or N;

G is O or S;

$Y^1$ is N;

$Y^2$ is $CR^{19}$ or N;

Q is —C(=O)-z, —C(=S)-z, —C(=O)—O-z, —C(=S)—O-z, —C(=O)—N($R^{20}$)-z, —C(=S)—N($R^{21}$)-z or —$SO_2$-z-, in each case z indicates the bond that is connected to $R^9$;

n is 1 or 2;

p is 1;

$R^1$ is phenyl or pyrazolyl; wherein the phenyl and pyrazolyl are each optionally substituted by 1 to 3 substituents independently selected from $C_1$-$C_4$ alkyl, $C_1$-$C_4$ haloalkyl, halogen, cyano, hydroxy and amino;

$R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$ and $R^{19}$ each independently are hydrogen, halogen, $C_1$-$C_4$alkyl, $C_1$-$C_4$haloalkyl;

$R^8$, $R^{20}$ and $R^{21}$ each independently are hydrogen or $C_1$-$C_4$alkyl; and $R^9$ is phenyl, benzyl or group (a):

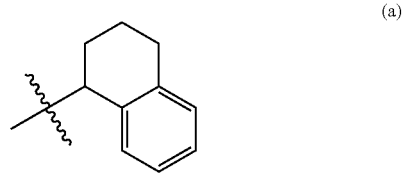 [SMILES: *C1CCCc2ccccc21]

wherein the phenyl, benzyl and group (a) are each optionally substituted with 1 to 3 substituents independently selected from $C_1$-$C_4$ alkyl, $C_1$-$C_4$ haloalkyl, halogen, cyano, hydroxy, and amino.

Preferably the compound of formula I is a compound wherein:

A is x-C(=O)—, -x-$CR^{10}R^{11}$—C(=O)—, x-O—C(=O)— or x-C($R^{16}R^{17}$)—$SO_2$—, in each case x indicates the bond that is connected to $R^1$;

T is $CR^{18}$ or N;

G is S;

$Y^1$ is N;

$Y^2$ is $CR^{19}$ or N;

Q is —C(=O)-z, —C(=O)—O-z, —C(=O)—N($R^{20}$)-z or —$SO_2$-z-, in each case z being the bond to $R^9$;

n is 1 or 2;

p is 1;

$R^1$ is phenyl or pyrazolyl, wherein the phenyl and pyrazolyl are optionally substituted with 1 to 3 substituents independently selected from $C_1$-$C_4$ alkyl, $C_1$-$C_4$ haloalkyl, and halogen;

$R^2$, $R^3$, $R^4$, $R^5$, $R^6$, $R^7$, $R^{10}$, $R^{11}$, $R^{16}$, $R^{17}$, $R^{18}$ and $R^{19}$ each independently are hydrogen, fluoro, or methyl;

$R^8$ and $R^{29}$ each independently are hydrogen or methyl; and $R^9$ is phenyl, benzyl or group (a):

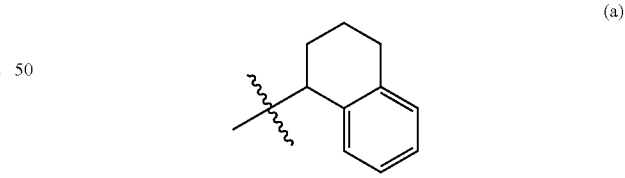

wherein the phenyl, benzyl and group (a) are each optionally substituted with 1 to 3 substituents independently selected from $C_1$-$C_4$ alkyl, $C_1$-$C_4$ haloalkyl, hydroxy and halogen.

Preferably the compound of formula I is a compound wherein:

A is x-C(=O)—, x-$CH_2$—C(=O)—, x-O—C(=O)— or x-$CH_2$—$SO_2$—, in each case x indicates the bond that is connected to $R^1$;

T is CH or N;

G is S;

$Y^1$ is N;

$Y^2$ is CH or N;

Q is —C(=O)-z, —C(=O)—O-z, —C(=O)—NH-z or —SO₂-z-, in each case z indicates the bond that is connected to R⁹;
n is 1 or 2;
p is 1;
R¹ is phenyl or group (b):

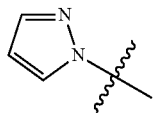
(b)

wherein the phenyl and group (b) are optionally substituted with 1 to 3 substituents independently selected from halogen, $C_1$-$C_4$ alkyl and $C_1$-$C_4$ haloalkyl;
$R^2, R^3, R^4, R^5, R^6$ and $R^7$ are each hydrogen;
$R^8$ is hydrogen; and
$R^9$ is phenyl, benzyl or group (a):

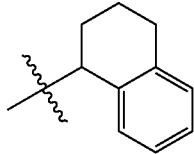
(a)

wherein the phenyl, benzyl and group (a) are each optionally substituted with 1 to 3 substituents independently selected from $C_1$-$C_4$ alkyl, $C_1$-$C_4$ haloalkyl, hydroxy and halogen.
Preferably the compound of formula I is a compound wherein:
A is x-CH₂—C(=O)— wherein x indicates the bond that is connected to R¹;
T is CH;
G is S;
Y¹ is N;
Y² is CH;
Q is —C(=O)-z, —C(=O)—O-z or C(=O)—N(R²⁰)-z, in each case z indicates the bond that is connected to R⁹;
n is 2;
p is 1;
R¹ is selected from group (c) or (d):

(c)

(d)

wherein $R^{22}$, $R^{23}$, $R^{24}$ and $R^{25}$ are independently selected from hydrogen, halogen, methyl and halomethyl;
$R_2, R_3, R_4, R_5, R_6$, and $R_7$ are each hydrogen;
$R_8$, is hydrogen;
$R^9$ is phenyl, benzyl or group (a):

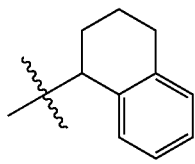
(a)

wherein the phenyl, benzyl and group (a) are optionally substituted with 1 to 3 substituents independently selected from halogen, hydroxy, methyl and halomethyl.
The invention also provides a compound of formula I in which:
A is x-CH₂C(=O)—, x-CH₂C(=S)—, x-OC(=O)—, x-C(=O)— or x-CH₂—SO₂—, in each case x indicates the bond that is connected to R¹;
T is CH or N;
G is O or S;
Y¹ is N;
Y² is CH or N;
Q is —C(=O)-z, —C(=S)-z, —C(=O)O-z, —C(=O)NH-z or —SO₂-z, in each case z indicates the bond that is connected to R⁹;
n is 1 or 2;
p is 1 or 2, providing that when n is 2, p is 1;
R¹ is group (e), (f), (g), or (h):

(e)

(f)

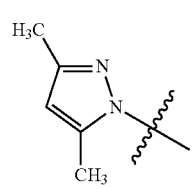
(g)

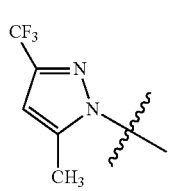
(h)

$R^2$, $R^3$, $R^4$, $R^5$, $R^6$ and $R^7$ are H;
$R^8$ is H or methyl;
$R^9$ is group (i), (j), (k), (l) or (m):

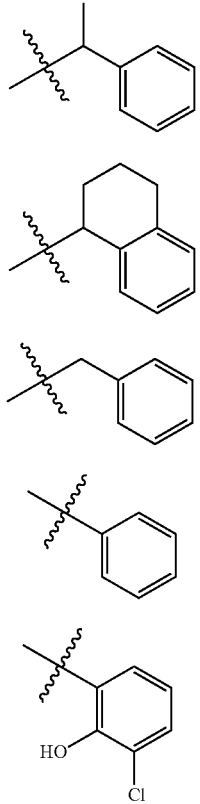

(i)

(j)

(k)

(l)

(m)

The following list provides definitions, including preferred definitions, for substituents A, T, G, $Y^1$, $Y^2$, n, p, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ with reference to compounds of formula I. For any one of these substituents, any of the definitions given below may be combined with any definition of any other substituent given below or elsewhere in this document. The invention includes compounds of formula having all possible combinations of substituent definitions given below. Generally, in this document any substituent definition may be combined with any other substituent definition.

A is x-C(=O)—, x-C(=S)—, x-C($R^{10}R^{11}$)—C(=O)—, x-C($R^{12}R^{13}$)—C(=S)—, x-O—C(=O)—, x-O—C(=S)—, x-N($R^{14}$)—C(=O)—, x-N($R^{15}$)—C(=S)—, x-C($R^{16}R^{17}$)—SO$_2$— or x-N=C($R^{26}$)—, in each case x indicates the bond that is connected to $R^1$. Preferably A is x-C(=O)—, x-C(=S)—, x-C($R^{10}R^{11}$)—C(=O)—, x-C($R^{12}R^{13}$)—C(=S)—, x-O—C(=O)—, x-O—C(=S)—, x-N($R^{14}$)—C(=O)—, x-N($R^{15}$)—C(=S)— or x-C($R^{16}R^{17}$)—SO$_2$—, in each case x indicates the bond that is connected to $R^1$. More preferably, A is x-C(=O)—, x-C(=S)—, x-C($R^{10}R^{11}$)—C(=O)—, x-C($R^{12}R^{13}$)—C(=S)—, x-O—C(=O)—, x-O—C(=S)— or x-C($R^{16}R^{17}$)—SO$_2$—, in each case x indicates the bond that is connected to $R^1$. Even more preferably, A is x-C(=O)—, -x-C$R^{10}R^{11}$-C(=O)—, x-O—C(=O)— or x-C($R^{16}R^{17}$)—SO$_2$—, in each case x indicates the bond that is connected to $R^1$. Yet more preferably, A is x-CH$_2$C(=O)—, x-CH$_2$C(=S)—, x-OC(=O)—, x-C(=O)— or x-CH$_2$—SO$_2$—, in each case x indicates the bond that is connected to $R^1$. Most preferably, A is x-CH$_2$—C(=O)— wherein x indicates the bond that is connected to $R^1$.

T is $CR^{18}$ or N. Preferably, T is CH or N. More preferably, T is CH.

G is O or S. Preferably, G is S.

$Y^1$ is $CR^{19}$ or N. Preferably, $Y^1$ is N.

$Y^2$ is $CR^{19}$ or N. Preferably, $Y^2$ is CH or N. More preferably, $Y^2$ is CH.

Q is —C(=O)-z, —C(=S)-z, —C(=O)—O-z, —C(=S)—O-z, —C(=O)—N($R^{20}$)-z, —C(=S)—N($R^{21}$)-z or —SO$_2$-z-, in each case z indicates the bond that is connected to $R^9$. Preferably, Q is —C(=O)-z, —C(=S)-z, —C(=O)O-z, —C(=O)NH-z or —SO$_2$-z, in each case z indicates the bond that is connected to $R^9$. Preferably, Q is —C(=O)-z, —C(=O)—O-z, —C(=O)—N($R^{20}$)-z or —SO$_2$-z-, in each case z indicates the bond that is connected to $R^9$. More preferably, Q is —C(=O)-z, —C(=O)—O-z, —C(=O)—NH-z or —SO$_2$-z-, in each case z indicates the bond that is connected to $R^9$. Even more preferably, Q is Q is —C(=O)-z, —C(=O)—O-z or C(=O)—N($R^{20}$)-z, in each case z indicates the bond that is connected to $R^9$. Most preferably Q is —C(=O)-z wherein z indicates the bond that is connected to $R^9$.

n is 1 or 2. Preferably, n is 2.

p is 1 or 2, providing that when n is 2, p is 1. Preferably p is 1.

$R^1$ is phenyl, pyridyl, imidazolyl, or pyrazolyl; wherein the phenyl, pyridyl, imidazolyl and pyrazolyl are each optionally substituted by 1 to 3 substituents independently selected from $C_1$-$C_4$ alkyl, $C_1$-$C_4$ haloalkyl, halogen, cyano, hydroxy and amino. Preferably, $R^1$ is phenyl or pyrazolyl; wherein the phenyl and pyrazolyl are each optionally substituted by 1 to 3 substituents independently selected from $C_1$-$C_4$ alkyl, $C_1$-$C_4$ haloalkyl, halogen, cyano, hydroxy, and amino. Preferably, $R^1$ is phenyl or pyrazolyl, wherein the phenyl and pyrazolyl are optionally substituted with 1 to 3 substituents independently selected from $C_1$-$C_4$ alkyl, $C_1$-$C_4$ haloalkyl, and halogen. More preferably, $R^1$ is phenyl or group (b):

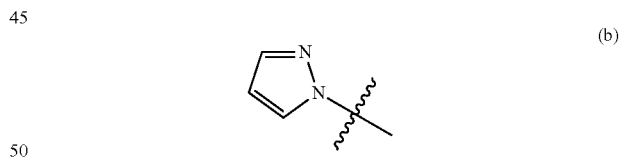

(b)

wherein the phenyl and group (b) are optionally substituted with 1 to 3 substituents independently selected from halogen, $C_1$-$C_4$ alkyl and $C_1$-$C_4$ haloalkyl.

In one group of compounds $R^1$ is selected from group (c) or (d):

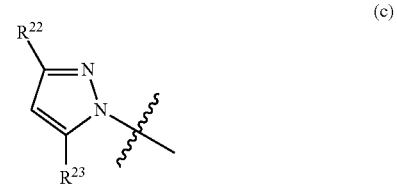

(c)

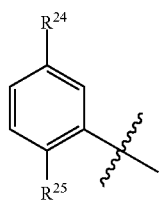
(d)

wherein $R^{22}$, $R^{23}$, $R^{24}$ and $R^{25}$ are independently selected from hydrogen, halogen, methyl and halomethyl.

In one group of compounds $R^1$ is group (e), (f), (g), or (h):

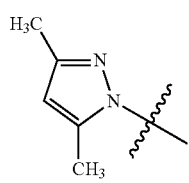
(e)

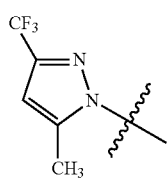
(f)

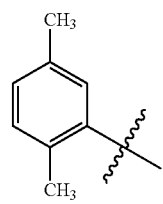
(g)

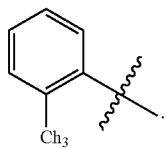
(h)

$R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$, $R^{19}$ each independently are hydrogen, halogen, cyano, $C_1$-$C_4$alkyl, or $C_1$-$C_4$haloalkyl. Preferably, $R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$ and $R^{19}$ each independently are hydrogen, halogen, $C_1$-$C_4$alkyl, or $C_1$-$C_4$haloalkyl. More preferably, $R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$ and $R^{19}$ each independently are hydrogen, fluoro, or methyl. Even more preferably, $R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$ and $R^{19}$ each independently are hydrogen.

$R^8$, $R^{14}$, $R^{15}$, $R^{20}$, and $R^{21}$ each independently are hydrogen or $C_1$-$C_4$alkyl. Preferably, $R^8$, $R^{14}$, $R^{15}$, $R^{20}$, and $R^{21}$ each independently are hydrogen or methyl.

More preferably, $R^8$, $R^{14}$, $R^{15}$, $R^{20}$, and $R^{21}$ each independently are hydrogen.

$R^9$ is phenyl, benzyl or group (a):

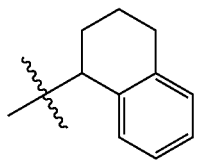
(a)

wherein the phenyl, benzyl and group (a) are each optionally substituted with 1 to 3 substituents independently selected from $C_1$-$C_4$ alkyl, $C_1$-$C_4$ haloalkyl, $C_1$-$C_4$ alkoxy, $C_1$-$C_4$ haloalkoxy, halogen, cyano, hydroxyl, $N(R^{27})_2$, SH, $C_1$-$C_4$ alkylthio, nitro, phenylsulfonyl and phenylsulfinyl, wherein the phenylsulfonyl and phenylsulfinyl are optionally substituted by 1 to 3 substituents independently selected from $C_1$-$C_4$ alkyl, $C_1$-$C_4$ haloalkyl, $C_1$-$C_4$ alkoxy, $C_1$-$C_4$ haloalkoxy, halogen and cyano. Preferably, $R^9$ is phenyl, benzyl or group (a):

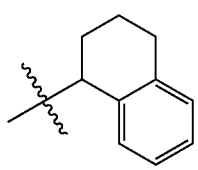
(a)

wherein the phenyl, benzyl and group (a) are each optionally substituted with 1 to 3 substituents independently selected from $C_1$-$C_4$ alkyl, $C_1$-$C_4$ haloalkyl, halogen, cyano, hydroxy and amino. Preferably, $R^9$ is phenyl, benzyl or group (a):

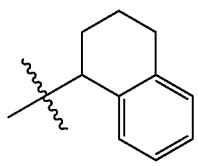
(a)

wherein the phenyl, benzyl and group (a) are each optionally substituted with 1 to 3 substituents independently selected from $C_1$-$C_4$ alkyl, $C_1$-$C_4$ haloalkyl, hydroxy and halogen. More preferably, $R^9$ is phenyl, benzyl or group (a):

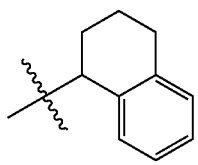
(a)

wherein the phenyl, benzyl and group (a) are optionally substituted with 1 to 3 substituents independently selected from halogen, hydroxy, methyl and halomethyl.

$R^{26}$ is hydrogen, halogen, cyano, $C_1$-$C_4$alkyl, or $C_1$-$C_4$haloalkyl. Preferably, $R^{26}$ is hydrogen, halogen, $C_1$-$C_4$alkyl, or $C_1$-$C_4$haloalkyl. Preferably, $R^{26}$ is hydrogen, fluoro, or methyl. More preferably, $R^{26}$ is hydrogen.

Each $R^{27}$ independently is hydrogen, $C_1$-$C_4$ alkyl, phenylsulfonyl or phenylsulfinyl, wherein the phenylsulfonyl and phenylsulfinyl are optionally substituted by 1 to 3 substituents independently selected from $C_1$-$C_4$ alkyl, $C_1$-$C_4$ haloalkyl, $C_1$-$C_4$ alkoxy, $C_1$-$C_4$ haloalkoxy, halogen and cyano. Preferably, $R^{27}$ is independently is hydrogen, $C_1$-$C_4$ alkyl, phenylsulfonyl or phenylsulfinyl, wherein the phenylsulfonyl and phenylsulfinyl are optionally substituted by 1 to 3 substituents independently selected from halogen, methyl and halomethyl.

In one group of compounds $R^9$ is group (i), (j), (k), (l) or (m):

(i)
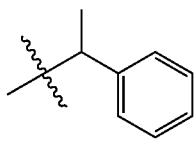

(j)
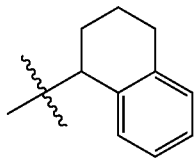

(k)
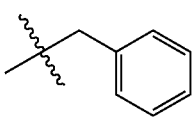

(l)
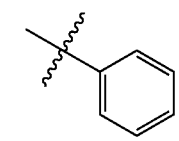

(m)
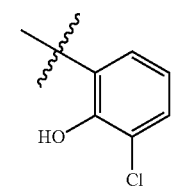

Preferably $R^{22}$ is hydrogen or $CF_3$.

Preferably $R^{23}$, $R^{24}$, and $R^{25}$ are independently hydrogen or methyl.

In one group of compounds G is S, $Y^1$ is N and $Y^2$ is CH.

In one group of compounds p is 1 and n is 2.

In one group of compounds $R^2$, $R^3$, $R^4$, $R^5$, $R^6$ and $R^7$ are H.

In one group of compounds Q is —C(═O)-z, wherein z indicates the bond that is connected to $R^9$.

In one group of compounds A is x-$CH_2$—C(═O)—, wherein x indicates the bond that is connected to $R^1$.

In one group of compounds $R^1$ is group (f)

(f)
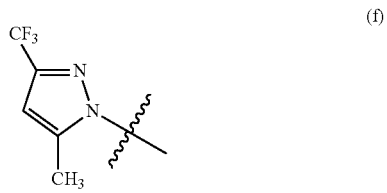 [SMILES: *n1nc(C(F)(F)F)cc1C]

In one group of compounds $R^9$ is phenyl substituted by hydroxyl, and optionally substituted by one or two further substituents as defined above. Preferably the hydroxy is at the ortho position. Preferably one of the further substituents is halogen and is preferably at the meta position adjacent to the hydroxy.

For the avoidance of doubt, when n is 1 and p is 1 compounds of formula I have the formula according to formula IA:

(IA)
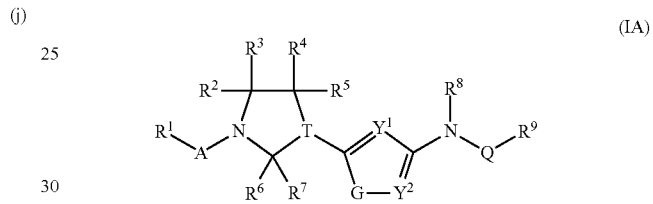

in which A, T, G, $Y^1$, $Y^2$, Q, $R^1$, $R^2$, $R^3$, $R^4$, $R^5$, $R^6$, $R^7$, $R^8$, and $R^9$ have the definitions as described for formula I.

When n is 2 and p is 1, compounds of formula I have the formula according to formula IB:

(IB)
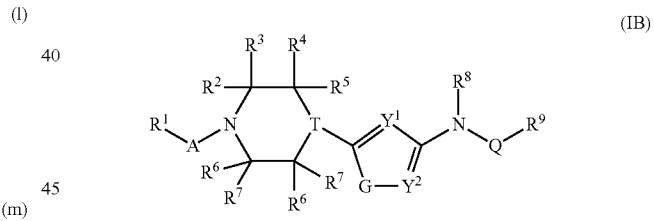

in which A, T, G, $Y^1$, $Y^2$, Q, $R^1$, $R^2$, $R^3$, $R^4$, $R^5$, $R^6$, $R^7$, $R^8$, and $R^9$ have the definitions as described for formula I.

When n is 1 and p is 2, compounds of formula I have the formula according to formula IC:

(IC)
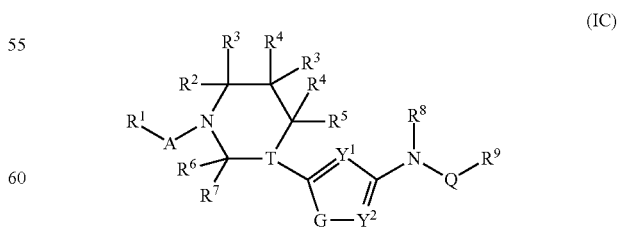

in which A, T, G, $Y^1$, $Y^2$, Q, $R^1$, $R^2$, $R^3$, $R^4$, $R^5$, $R^6$, $R^7$, $R^8$, and $R^9$ have the definitions as described for formula I.

The invention also relates to compounds of formula IA, formula IB and formula IC as shown above.

The invention also relates to compounds of formula ID:

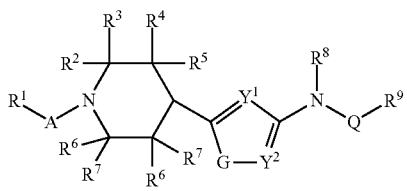

(ID)

in which A, G, $Y^1$, $Y^2$, Q, $R^1$, $R^2$, $R^3$, $R^4$, $R^5$, $R^6$, $R^7$, $R^8$, and $R^9$ have the definitions as described for formula I. Preferred definitions of A, G, $Y^1$, $Y^2$, Q, $R^1$, $R^2$, $R^3$, $R^4$, $R^5$, $R^6$, $R^7$, $R^8$, and $R^9$ are as defined for formula I.

The invention also relates to compounds of formula IE:

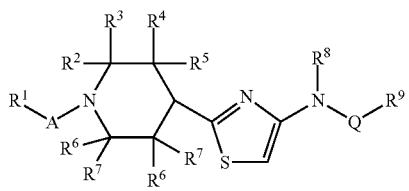

(IE)

in which A, Q, $R^1$, $R^2$, $R^3$, $R^4$, $R^5$, $R^6$, $R^7$, $R^8$, and $R^9$ have the definitions as described for formula I. Preferred definitions of A, Q, $R^1$, $R^2$, $R^3$, $R^4$, $R^5$, $R^6$, $R^7$, $R^8$, and $R^9$ are as defined for formula I.

The invention also relates to compounds of formula IF:

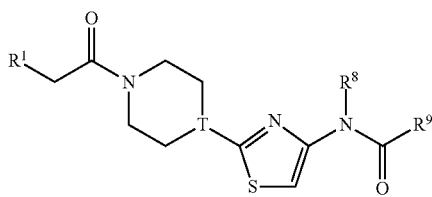

(IF)

wherein T is CH or N
$R^8$ is $CH_3$ or H; and
$R^1$ and $R^9$ have the definitions as described for formula I. Preferred definitions of $R^1$ and $R^9$ are as defined for formula I.

The invention also relates to compounds of formula IG:

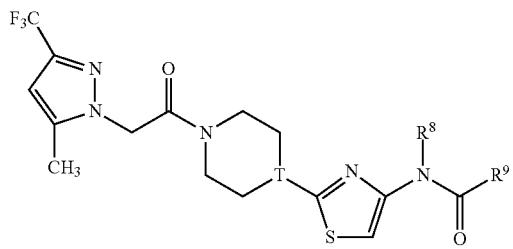

(IG)

wherein T is CH or N
$R^8$ is $CH_3$ or H; and $R^9$ has the definition as described for formula I. Preferred definitions of $R^9$ are as defined for formula I.

The invention also includes compounds of formula I in which $R^1$ is a protecting group, such as an alkyl group. Accordingly the invention includes compounds of formula I.a:

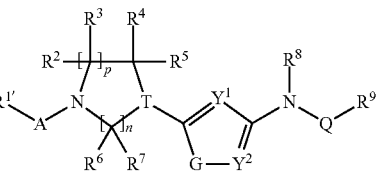

(I.a)

in which $R^{1'}$ is $C_1$-$C_8$ alkyl, e.g. $C_1$-$C_4$ alkyl, e.g. tert-butyl; and A, T, G, $Y^1$, $Y^2$, Q, n, p, $R^2$, $R^3$, $R^4$, $R^5$, $R^6$, $R^7$, $R^8$, and $R^9$ have the definitions as described for formula I. Preferably A is x-O—C(=O)—, x indicating the bond to $R^1$. Preferred definitions of A, T, G, $Y^1$, $Y^2$, Q, n, p, $R^2$, $R^3$, $R^4$, $R^5$, $R^6$, $R^7$, $R^8$, and $R^9$ areas defined for formula I.

These compounds are useful in the synthesis of compounds of formula I.

The invention also includes compounds of formula II:

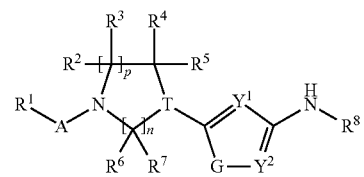

(II)

wherein $R^1$, $R^2$, $R^3$, $R^4$, $R^5$, $R^6$, $R^7$, $R^8$, A, T, G, $Y^1$, $Y^2$, p and n are as defined for formula I. Preferred definitions of $R^1$, $R^2$, $R^3$, $R^4$, $R^5$, $R^6$, $R^7$, $R^8$, A, T, G, $Y^1$, $Y^2$, p and n are as defined for formula I. Compounds of formula II are useful as intermediates in the synthesis of compounds of formula I.

The invention also includes compounds of formula VIII:

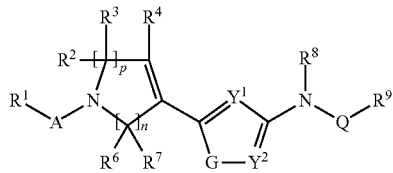

(VIII)

wherein $R^1$, $R^2$, $R^3$, $R^4$, $R^6$, $R^7$, $R^8$, A, T, G, $Y^1$, $Y^2$, p and n are as defined for formula I. Preferred definitions of $R^1$, $R^2$, $R^3$, $R^4$, $R^6$, $R^7$, $R^8$, A, T, G, $Y^1$, $Y^2$, p and n are as defined for formula I. Compounds of formula VIII are useful as intermediates in the synthesis of compounds of formula I.

Preferred individual compounds are:
(R)-1,2,3,4-tetrahydro-naphthalene-1-carboxylic acid (2-{1-[2-(5-methyl-3-trifluoromethyl-pyrazol-1-yl)-acetyl]-piperidin-4-yl}-thiazol-4-yl)amide (Compound No. 1.g.001);
3-chloro-2-hydroxy-N-(2-{1-[2-(5-methyl-3-trifluoromethyl-pyrazol-1-yl)-acetyl]-piperidin-4-yl}-thiazol-4-yl)-benzamide (Compound No. I.g.006);
1,2,3,4-tetrahydro-naphthalene-1-carboxylic acid (2-{1-[2-(5-methyl-3-trifluoromethyl-pyrazol-1-yl)-acetyl]-piperidin-4-yl}-thiazol-4-yl)amide (Compound No. 1.g.011);

(2-{1-[2-(5-methyl-3-trifluoromethyl-pyrazol-1-yl)-acetyl]-piperidin-4-yl}-thiazol-4-yl)-carbamic acid 1,2,3,4-tetrahydro-naphthalen-1-yl ester (Compound No. I.g.013);

N-2-{1-[2-(5-methyl-3-trifluoromethyl-pyrazol-1-yl)-acetyl]-piperidin-4-yl}-thiazol-4-yl)-2-phenyl-propionamide (Compound No. I.g.016);

N-(2-{1-[2-(5-methyl-3-trifluoromethyl-pyrazol-1-yl)-acetyl]-piperidin-4-yl}-thiazol-4-yl)-carbamic acid 1-phenyl-ethyl ester (Compound No. I.g.018)

N-2-{1-[2-(5-methyl-3-trifluoromethyl-pyrazol-1-yl)-acetyl]-piperidin-4-yl}-thiazol-4-yl)-benzamide (Compound No. I.g.021);

2-{1-[2-(5-methyl-3-trifluoromethyl-pyrazol-1-yl)-acetyl]-piperidin-4-yl}-thiazol-4-yl)-carbamic acid phenyl ester (Compound No. I.g.023);

1-(2-{1-[2-(5-methyl-3-trifluoromethyl-pyrazol-1-yl)-acetyl]-piperidin-4-yl}-thiazol-4-yl)-3-phenyl-urea (Compound No. I.g.024);

1,2,3,4-tetrahydro-naphthalene-1-carboxylic acid (2-{1-[2-(2,5-dimethylphenyl)-acetyl]-piperidin-4-yl}-thiazol-4-yl)-amide (Compound No. 1.g. 136);

N-(2-{1-[2-(2,5-Dimethyl-phenyl)-acetyl]-piperidin-4-yl}-thiazol-4-yl)-2-phenyl-propionamide (Compound No. I.g.141);

N-{2-[1-(2,5-Dimethyl-phenylmethanesulfonyl)-piperidin-4-yl]-thiazol-4-yl}-benzamide (Compound No. I.g.246)

1,2,3,4-tetrahydro-naphthalene-1-carboxylic acid {2-[1-(2-o-tolyl-acetyl)-piperidin-4-yl]thiazol-4-yl}-amide (Compound No. I.g.386)

3-fluoro-2-hydroxy-N-(2-{1-[2-(5-methyl-3-trifluoromethyl-pyrazol-1-yl)-acetyl]-piperidin-4-yl}-thiazol-4-yl)-benzamide (Compound No. I.g.501);

3-bromo-2-hydroxy-N-(2-{1-[2-(5-methyl-3-trifluoromethyl-pyrazol-1-yl)-acetyl]-piperidin-4-yl}-thiazol-4-yl)-benzamide (Compound No. I.g.502);

2-hydroxy-N-(2-{1-[2-(5-methyl-3-trifluoromethyl-pyrazol-1-yl)-acetyl]-piperidin-4-yl}-thiazol-4-yl)-benzamide (Compound No. I.g.503);

2-methoxy-N-(2-{1-[2-(5-methyl-3-trifluoromethyl-pyrazol-1-yl)-acetyl]-piperidin-4-yl}-thiazol-4-yl)-benzamide (Compound No. I.g.506);

N-(2-{1-[2-(5-methyl-3-trifluoromethyl-pyrazol-1-yl)-acetyl]-piperidin-4-yl}-thiazol-4-yl)-2-(toluene-4-sulfonylamino)-benzamide (Compound No. I.g.508);

2-methoxy-6-hydroxy-N-(2-{1-[2-(5-methyl-3-trifluoromethyl-pyrazol-1-yl)-acetyl]-piperidin-4-yl}-thiazol-4-yl)-benzamide (Compound No. I.g.509);

2-fluoro-6-hydroxy-N-(2-{1-[2-(5-methyl-3-trifluoromethyl-pyrazol-1-yl)-acetyl]-piperidin-4-yl}-thiazol-4-yl)-benzamide (Compound No. I.g.510);

3-methoxy-2-hydroxy-N-(2-{1-[2-(5-methyl-3-trifluoromethyl-pyrazol-1-yl)-acetyl]-piperidin-4-yl}-thiazol-4-yl)-benzamide (Compound No. I.g.510); 1,2,3,4-tetrahydro-naphthalene-1-carboxylic acid methyl-(2-{1-[2-(5-methyl-3-trifluoromethyl-pyrazol-1-yl)-acetyl]-piperidin-4-yl}-thiazol-4-yl)-amide (Compound No. 1.h.011); and N-methyl-N-2-{1-[2-(5-methyl-3-trifluoromethyl-pyrazol-1-yl)-acetyl]-piperidin-4-yl}-thiazol-4-yl)-2-phenyl-propionamide (Compound No. I.h.016).

1,2,3,4-Tetrahydro-naphthalene-1-carboxylic acid (2-{4-[2-(5-methyl-3-trifluoromethyl-pyrazol-1-yl)acetyl]-piperazin-1-yl}-thiazol-4-yl)amide (Compound No. I.n.011); and N-(2-{4-[2-(5-methyl-3-trifluoromethyl-pyrazol-1-yl)-acetyl]-piperazin-1-yl}-thiazol-4-yl)-benzamide (Compound No. I.n.011).

Compounds of formula (I) can be made as shown in the following schemes.

The compounds of formula I, wherein $R^1$, $R^2$, $R^3$, $R^4$, $R^5$, $R^6$, $R^7$, $R^8$, $R^9$, A, T, G, $Y^1$, $Y^2$, n, p and Q are as defined for formula I can be obtained by transformation of a compound of formula II, wherein $R^1$, $R^2$, $R^3$, $R^4$, $R^5$, $R^6$, $R^7$, $R^8$, A, T, G, $Y^1$, $Y^2$, n, p and Y are as defined for formula I with a compound of formula III, wherein $R^9$ and Q are as defined for formula I and X is a hydroxy, halogen, preferably fluoro, chloro or bromo or alkoxy, such as methoxy, ethoxy. This is shown in Scheme 1.

Scheme 1

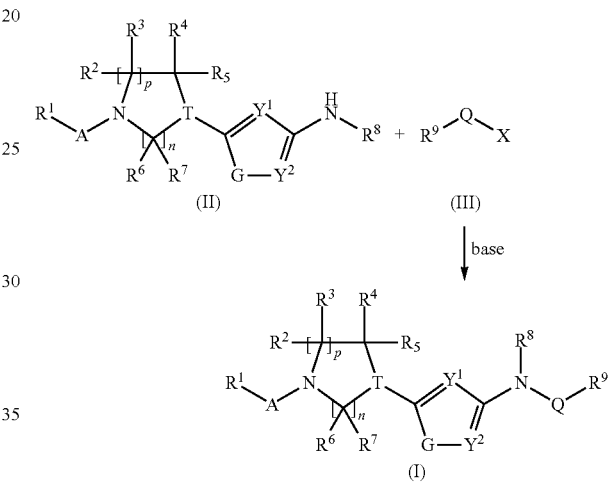

The compounds of formula II.1, wherein $R^1$, $R^2$, $R^3$, $R^4$, $R^5$, $R^6$, $R^7$, A, T, G, n, p, $Y^1$ and $Y^2$ are as defined for formula I, can be obtained by transformation of a compound of formula IV, wherein $R^1$, $R^2$, $R^3$, $R^4$, $R^5$, $R^6$, $R^7$, A, T, G, n, p, $Y^1$ and $Y^2$ are as defined for formula I with an azide, such as diphenyl phosphoryl azide and subsequent Curtius rearrangement of the resulting acyl azide with an alcohol $R^{28}$—OH, wherein $R^{28}$ is $C_1$-$C_6$alkyl or optionally substituted aryl and following carbamate cleavage with a mineral acid, such as hydrochloric acid, sulfuric acid or an organic acid, such as trifluoroacetic acid. This is shown in Scheme 2.

Scheme 2

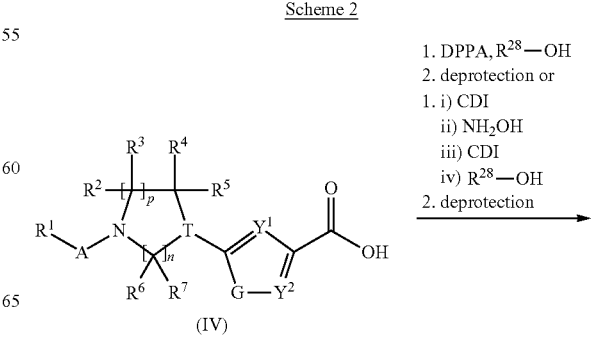

-continued

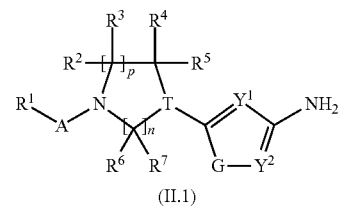

(II.1)

The compounds of formula IV, wherein $R^1$, $R^2$, $R^3$, $R^4$, $R^5$, $R^6$, $R^7$, A, T, G, n, p, $Y^1$ and $Y^2$ are as defined for formula I can be obtained by saponification of a compound of formula V, wherein $R^1$, $R^2$, $R^3$, $R^4$, $R^5$, $R^6$, $R^7$, A, T, G, n, p, $Y^1$ and $Y^2$ are as defined for formula I and $R^{28}$ is $C_1$-$C_6$alkyl or optionally substituted aryl with a base, such as sodium hydroxide, potassium hydroxide or lithium hydroxide. This is shown in Scheme 3.

Scheme 3

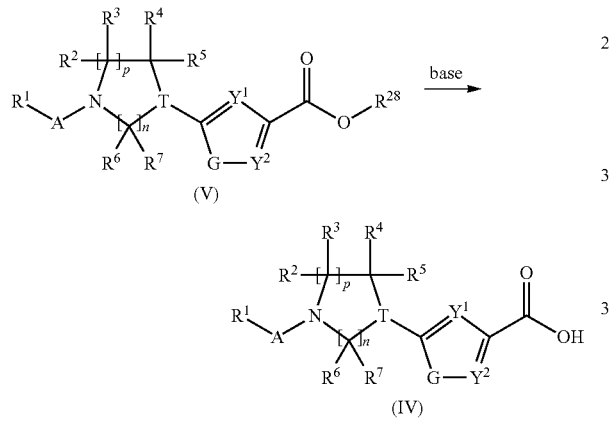

The compounds of formula V, wherein $R^1$, $R^2$, $R^3$, $R^4$, $R^5$, $R^6$, $R^7$, A, T, G, n, p, $Y^1$ and $Y^2$ are as defined for formula I and $R^{28}$ is $C_1$-$C_6$alkyl or optionally substituted aryl can be obtained by transformation of a compound of formula VI, wherein $R^2$, $R^3$, $R^4$, $R^5$, $R^6$, $R^7$, T, G, n, p, $Y^1$ and $Y^2$ are as defined for formula I and $R^{28}$ is $C_1$-$C_6$alkyl or optionally substituted aryl with a compound of formula VII, wherein $R^1$ and A are as defined for formula I and X is a hydroxy, halogen, preferably fluoro, chloro or bromo or alkoxy, such as methoxy, ethoxy. This is shown in Scheme 4.

Scheme 4

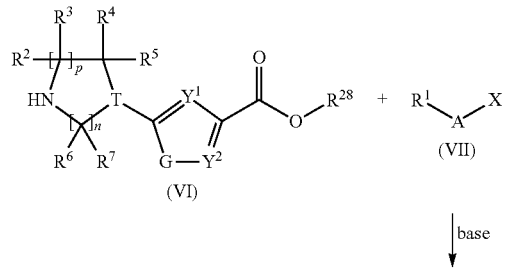

-continued

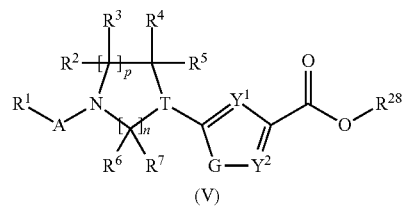

(V)

Alternatively, the compounds of formula I.1, wherein $R^1$, $R^2$, $R^3$, $R^4$, $R^5$, $R^6$, $R^7$, $R^9$, A, T, G, n, $Y^1$ and $Y^2$ are as defined for formula I and $R^{29}$ is $C_1$-$C_6$alkyl can be obtained by transformation of a compound of formula I.2, wherein $R^1$, $R^2$, $R^3$, $R^4$, $R^5$, $R^6$, $R^7$, $R^9$, A, T, G, n, $Y^1$ and $Y^2$ are as defined for formula I with an alkyl halide $R^{29}$-Hal, wherein $R^{29}$ is $C_1$-$C_6$alkyl and Hal is halogen, preferably chloro or bromo. This is shown in Scheme 5.

Scheme 5

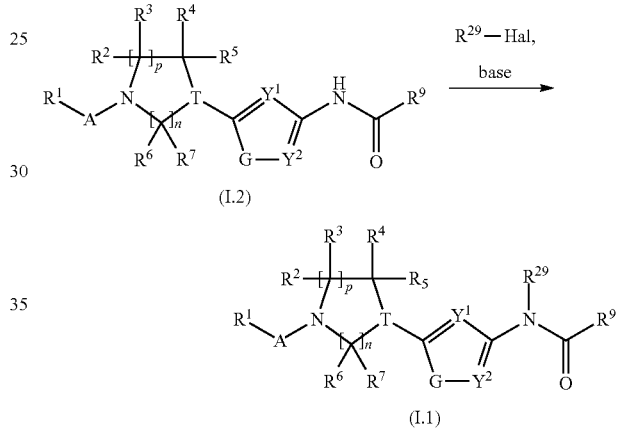

The compounds of formula I.2, wherein $R^1$, $R^2$, $R^3$, $R^4$, $R^5$, $R^6$, $R^7$, $R^9$, A, T, G, n, p, $Y^1$ and $Y^2$ are as defined for formula I can be obtained by transformation of a compound of formula IV, wherein $R^1$, $R^2$, $R^3$, $R^4$, $R^5$, $R^6$, $R^7$, A, T, G, n, p, $Y^1$ and $Y^2$ are as defined for formula I with an azide, such as diphenyl phosphoryl azide and subsequent Curtius rearrangement of the resulting acyl azide with a Grignard reagent $R^9$-Mg-Hal, wherein $R^9$ is as defined for formula I and Hal is halogen, preferably chloro, bromo or iodo, or a boronic acid $R^9$—B$(OH)_2$, wherein $R^9$ is as defined for formula I and a catalyst, such as bis(1,5-cyclooctadiene)rhodium(I) hydroxide. This is shown in Scheme 6.

Scheme 6

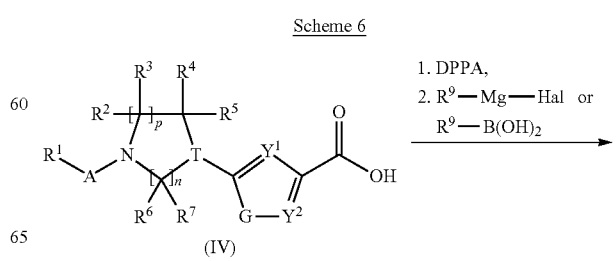

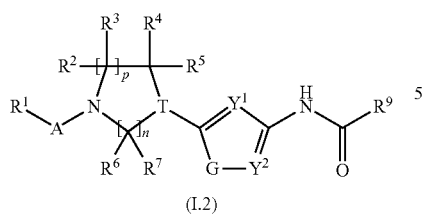

(I.2)

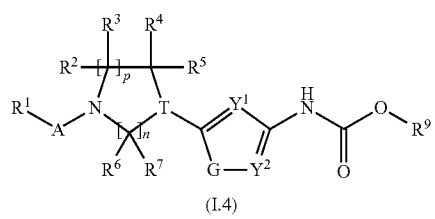

(I.4)

Alternatively, the compounds of formula I.3, wherein $R^1$, $R^2$, $R^3$, $R^4$, $R^5$, $R^6$, $R^7$, $R^9$, A, T, G, n, p, $Y^1$ and $Y^2$ are as defined for formula I and $R^{29}$ is $C_1$-$C_6$alkyl can be obtained by transformation of a compound of formula I.4, wherein $R^1$, $R^2$, $R^3$, $R^4$, $R^5$, $R^6$, $R^7$, $R^9$, A, T, G, n, p, $Y^1$ and $Y^2$ are as defined for formula I with an alkyl halide $R^{29}$-Hal, wherein $R^{29}$ is $C_1$-$C_6$alkyl and Hal is halogen, preferably chloro or bromo. This is shown in Scheme 7.

Alternatively, the compounds of formula I.5, wherein $R^1$, $R^2$, $R^3$, $R^4$, $R^5$, $R^6$, $R^7$, $R^9$, A, T, G, n, $Y^1$ and $Y^2$ are as defined for formula I and $R^{29}$ is $C_1$-$C_6$alkyl can be obtained by transformation of a compound of formula I.6, wherein $R^1$, $R^2$, $R^3$, $R^4$, $R^5$, $R^6$, $R^7$, $R^9$, A, T, G, n, $Y^1$ and $Y^2$ are as defined for formula I with an alkyl halide $R^{29}$-Hal, wherein $R^{29}$ is $C_1$-$C_6$alkyl and Hal is halogen, preferably chloro or bromo. This is shown in Scheme 9.

Scheme 7

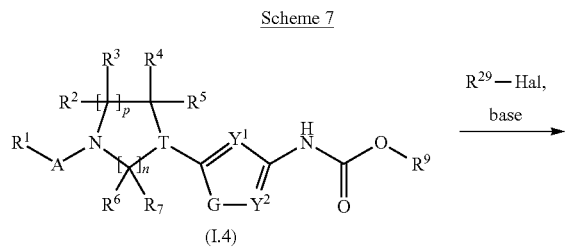

Scheme 9

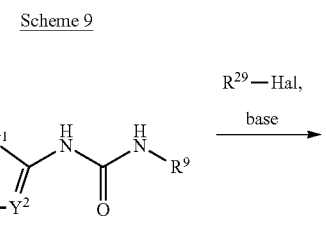

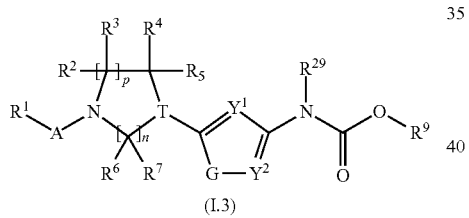

(I.3)

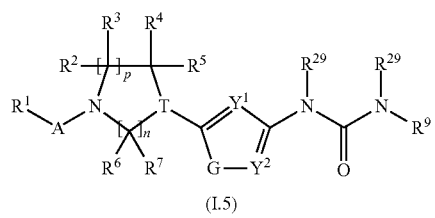

(I.5)

The compounds of formula I.4, wherein $R^1$, $R^2$, $R^3$, $R^4$, $R^5$, $R^6$, $R^7$, $R^9$, A, T, G, n, p, $Y^1$ and $Y^2$ are as defined for formula I can be obtained by transformation of a compound of formula IV, wherein $R^1$, $R^2$, $R^3$, $R^4$, $R^5$, $R^6$, $R^7$, A, T, G, n, p, $Y^1$ and $Y^2$ are as defined for formula I with an azide, such as diphenyl phosphoryl azide and subsequent Curtius rearrangement of the resulting acyl azide with an alcohol $R^9$—OH, wherein $R^9$ is as defined for formula I as defined for formula I. This is shown in Scheme 8.

The compounds of formula I.6, wherein $R^1$, $R^2$, $R^3$, $R^4$, $R^5$, $R^6$, $R^7$, $R^9$, A, T, G, n, p, $Y^1$ and $Y^2$ are as defined for formula I can be obtained by transformation of a compound of formula IV, wherein $R^1$, $R^2$, $R^3$, $R^4$, $R^5$, $R^6$, $R^7$, A, T, G, n, p, $Y^1$ and $Y^2$ are as defined for formula I with an azide, such as diphenyl phosphoryl azide and subsequent Curtius rearrangement of the resulting acyl azide with an amine $R^9$—$NH_2$, wherein $R^9$ is as defined for formula I. This is shown in Scheme 10.

Scheme 8

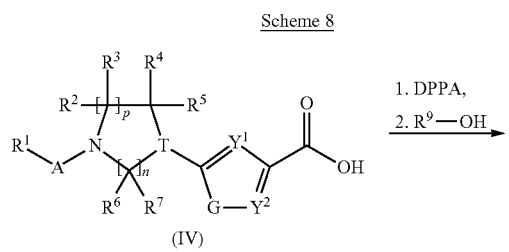

(IV)

Scheme 10

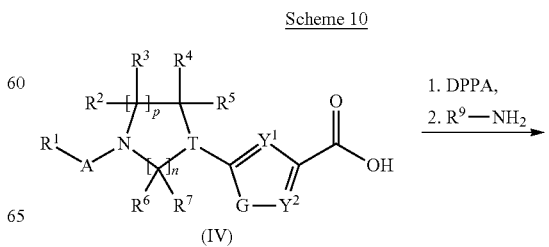

(IV)

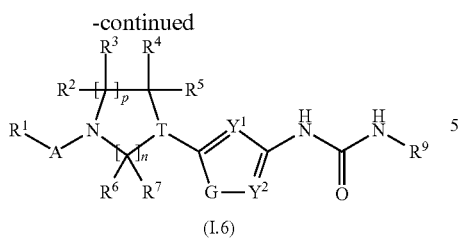

(I.6)

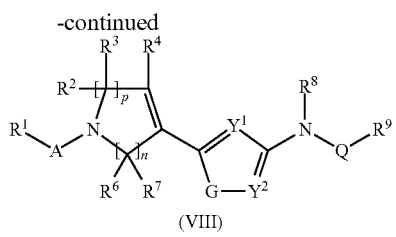

(VIII)

Alternatively, the compounds of formula I.7, wherein $R^1$, $R^2$, $R^3$, $R^4$, $R^5$, $R^6$, $R^7$, $R^8$, $R^9$, A, G, n, p, $Y^1$, $Y^2$ and Q are as defined for formula I, can be obtained by reduction of a compound of formula VIII, wherein $R^1$, $R^2$, $R^3$, $R^4$, $R^5$, $R^6$, $R^7$, $R^8$, $R^9$, A, G, n, p, $Y^1$, $Y^2$ and Q are as defined for formula I with hydrogen and a catalyst, such as palladium on charcoal, platinum or raney-nickel. This is shown in Scheme 11.

Alternatively, the compounds of formula V.1, wherein $R^1$, $R^2$, $R^3$, $R^4$, $R^5$, $R^6$, $R^7$, A, G, n, p, $Y^1$ and $Y^2$ are as defined for formula I and $R^{28}$ is $C_1$-$C_6$alkyl or optionally substituted aryl can be obtained by reduction of a compound of formula XI, wherein $R^1$, $R^2$, $R^3$, $R^4$, $R^5$, $R^6$, $R^7$, A, G, n, p, $Y^1$ and $Y^2$ are as defined for formula I and $R^{28}$ is $C_1$-$C_6$alkyl or optionally substituted aryl with hydrogen and a catalyst, such as palladium on charcoal, platinum or raney-nickel. This is shown in Scheme 13.

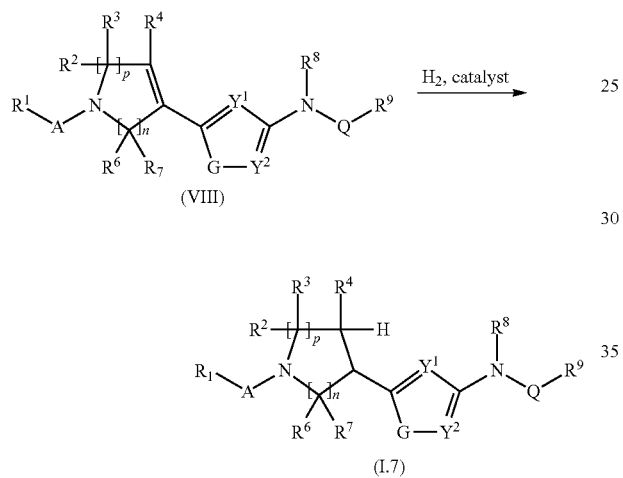

The compounds of formula VIII, wherein $R^1$, $R^2$, $R^3$, $R^4$, $R^5$, $R^6$, $R^7$, $R^8$, $R^9$, A, G, n, p, $Y^1$, $Y^2$ and Q are as defined for formula I can be obtained by cross coupling of a compound of formula IX, wherein $R^8$, $R^9$, G, $Y^1$, $Y^2$ and Q are as defined for formula I and Hal is halogen, preferably chloro, bromo or iodo with a compound of formula X, wherein $R^1$, $R^2$, $R^3$, $R^4$, $R^5$, $R^6$, $R^7$ and A are as defined for formula I and $R^{30}$ is $B(OH)_2$ and a transition metal, such as tetrakis(triphenylphosphine)palladium, and a ligand, such as. This is shown in Scheme 12.

The compounds of formula XI, wherein $R^1$, $R^2$, $R^3$, $R^4$, $R^5$, $R^6$, $R^7$, A, G, n, p, $Y^1$ and $Y^2$ are as defined for formula I and $R^{28}$ is $C_1$-$C_6$alkyl or optionally substituted aryl can be obtained by cross coupling of a compound of formula XII, wherein G, $Y^1$ and $Y^2$ are as defined for formula I, $R^{28}$ is $C_1$-$C_6$alkyl or optionally substituted aryl and Hal is halogen, preferably chloro, bromo or iodo with a compound of formula XIII, wherein $R^1$, $R^2$, $R^3$, $R^4$, $R^5$, $R^6$, $R^7$ and A are as defined for formula I and $R^{30}$ is $B(OH)_2$ and a transition metal, such as bis-(triphenylphosphine)palladium(II) chloride. This is shown in Scheme 14.

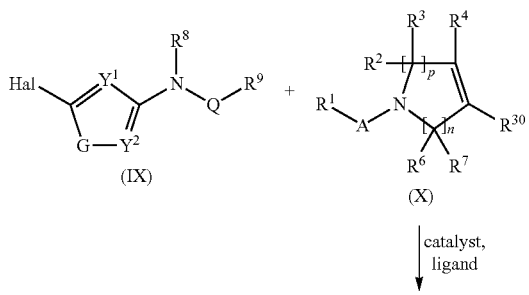

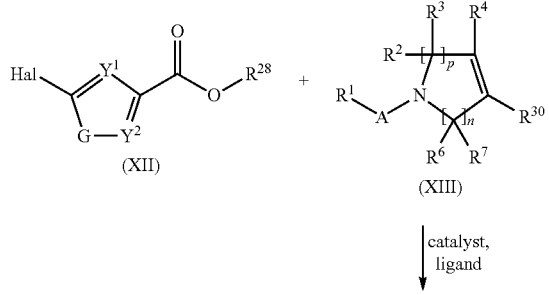

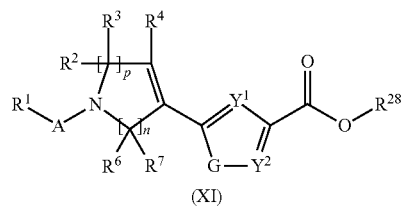

(XI)

Alternatively, the compounds of formula VIII, wherein $R^1$, $R^2$, $R^3$, $R^4$, $R^5$, $R^6$, $R^7$, $R^8$, $R^9$, A, G, n, p, $Y^1$, $Y^2$ and Q are as defined for formula I, can be obtained by cross coupling of a compound of formula XIV, wherein $R^1$, $R^2$, $R^3$, $R^4$, $R^5$, $R^6$, $R^7$, $R^8$, $R^9$, A, G, n, p, $Y^1$, and $Y^2$ are as defined for formula I with a compound of formula XV, wherein $R^8$, $R^9$ and Q are as defined for formula I and a ligand such as Xantphos or dimethylethylenediamine and a catalyst, such as Pd(OAc)$_2$ or copperiodide. This is shown in Scheme 15.

Scheme 15

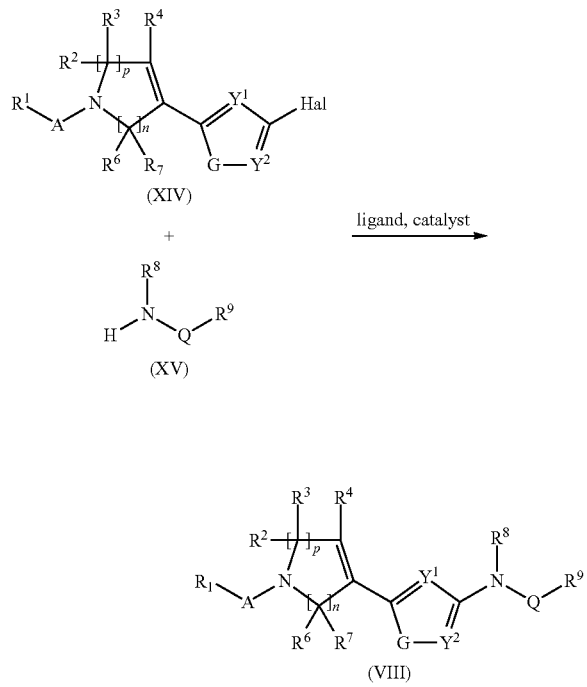

The compounds of formula XIV, wherein $R^1$, $R^2$, $R^3$, $R^4$, $R^5$, $R^6$, $R^7$, A, G, n, p, $Y^1$ and $Y^2$ are as defined for formula I can be obtained by cross coupling of a compound of formula XVI, wherein G, $Y^1$ and $Y^2$ are as defined for formula I, with a compound of formula XIII, wherein $R^1$, $R^2$, $R^3$, $R^4$, $R^5$, $R^6$, $R^7$ and A are as defined for formula I and $R^{30}$ is B(OH)$_2$ and a transition metal, such as bis-(triphenylphosphine)palladium (II) chloride. This is shown in Scheme 16.

Scheme 16

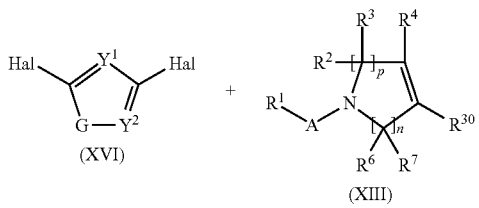

(XVI)       (XIII)

catalyst, ligand

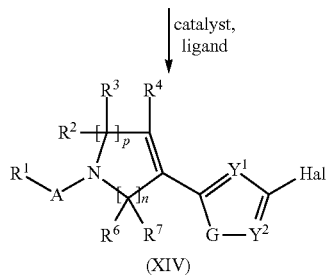

(XIV)

Surprisingly, it has now been found that the novel compounds of formula I have, for practical purposes, a very advantageous level of biological activity for protecting plants against diseases that are caused by fungi.

The compounds of formula I can be used in the agricultural sector and related fields of use e.g. as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, e.g., seed, such as fruits, tubers or grains, or plant cuttings (for example rice), for the protection against fungal infections as well as against phytopathogenic fungi occurring in the soil. The propagation material can be treated with a composition comprising a compound of formula I before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore the compounds according to present invention can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

The compounds of formula I are, for example, effective against the phytopathogenic fungi of the following classes:

Fungi imperfecti (e.g. *Alternaria* spp.), Basidiomycetes (e.g. *Corticium* spp., *Ceratobasidium* spp., *Waitea* spp., *Thanatephorus* spp., *Rhizoctonia* spp., *Hemileia* spp., *Puccinia* spp., *Phakopsora* spp., *Ustilago* spp., *Tilletia* spp.), Ascomycetes (e.g. *Venturia* spp., *Blumeria* spp., *Erysiphe* spp., *Podosphaera* spp., *Uncinula* spp., *Monilinia* spp., *Sclerotinia* spp., *Colletotrichum* spp., *Glomerella* spp., *Fusarium* spp., *Gibberella* spp., *Monographella* spp., *Phaeosphaeria* spp., *Mycosphaerella* spp., *Cercospora* spp., *Pyrenophora* spp., *Rhynchosporium* spp., *Magnaporthe* spp., *Gaeumannomyces* spp., *Oculimacula* spp., *Ramularia* spp., *Botryotinia* spp.) and Oomycetes (e.g. *Phytophthora* spp., *Pythium* spp., *Plasmopara* spp., *Peronospora* spp., *Pseudoperonospora* spp. *Bremia* spp). Outstanding activity is observed against downy mildew (e.g. *Plasmopara viticola*) and late blight (e.g. *Phytophthora infestans*). Furthermore, the novel compounds of formula I are effective against phytopathogenic gram negative and gram positive bacteria (e.g. *Xanthomonas* spp, *Pseudomonas* spp, *Erwinia amylovora, Ralstonia* spp.) and viruses (e.g. tobacco mosaic virus).

Within the scope of present invention, target crops and/or useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as turf and ornamentals.

The useful plants and/or target crops in accordance with the invention include conventional as well as genetically enhanced or engineered varieties such as, for example, insect resistant (e.g. Bt. and VIP varieties) as well as disease resistant, herbicide tolerant (e.g. glyphosate- and glufosinate-resistant maize varieties commercially available under the trade names RoundupReady® and LibertyLink®) and nematode tolerant varieties. By way of example, suitable genetically enhanced or engineered crop varieties include the Stoneville 5599BR cotton and Stoneville 4892BR cotton varieties.

The term "useful plants" and/or "target crops" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" and/or "target crops" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" and/or "target crops" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a plant as used herein is intended to embrace the place on which the plants are growing, where the plant propagation materials of the plants are sown or where the plant propagation materials of the plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I are normally used in the form of compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I may be used in the form of fungicidal compositions for controlling or protecting against phytopathogenic microorganisms, comprising as active ingredient at least one compound of formula I or of at least one preferred individual compound as above-defined, in free form or in agrochemically usable salt form, and at least one of the above-mentioned adjuvants.

The invention provides a fungicidal composition comprising at least one compound formula I an agriculturally acceptable carrier and optionally an adjuvant. An agricultural acceptable carrier is for example a carrier that is suitable for agricultural use. Agricultural carriers are well known in the art. Preferably said fungicidal compositions may comprise an additional fungicidal active ingredient in addition to the compound of formula I.

The compound of formula (I) may be the sole active ingredient of a composition or it may be admixed with one or more additional active ingredients such as an insecticide, fungicide, synergist, herbicide or plant growth regulator where appropriate. An additional active ingredient may, in some cases, result in unexpected synergistic activities. Examples of suitable additional active ingredients include the following: Azoxystrobin (131860-33-8), Dimoxystrobin (149961-52-4), Enestrobin (238410-11-2), Fluoxastrobin (193740-76-0), Kresoxim-methyl (143390-89-0), Metominostrobin (133408-50-1), Orysastrobin (248593-16-0), Picoxystrobin (117428-22-5), Pyraclostrobin (175013-18-0), Azaconazole (60207-31-0), Bromuconazole (116255-48-2), Cyproconazole (94361-06-5), Difenoconazole (119446-68-3), Diniconazole (83657-24-3), Diniconazole-M (83657-18-5), Epoxiconazole (13385-98-8), Fenbuconazole (114369-43-6), Fluquinconazole (136426-54-5), Flusilazole (85509-19-9), Flutriafol (76674-21-0), Hexaconazole (79983-71-4), Imazalil (58594-72-2), Imibenconazole (86598-92-7), Ipconazole (125225-28-7), Metconazole (125116-23-6), Myclobutanil (88671-89-0), Oxpoconazole (174212-12-5), Pefurazoate (58011-68-0), Penconazole (66246-88-6), Prochloraz (67747-09-5), Propiconazole (60207-90-1), Prothioconazole (178928-70-6), Simeconazole (149508-90-7), Tebuconazole (107534-96-3), Tetraconazole (112281-77-3), Triadimefon (43121-43-3), Triadimenol (55219-65-3), Triflumizole (99387-89-0), Triticonazole (131983-72-7), Diclobutrazol (76738-62-0), Etaconazole (60207-93-4), Fluconazole (86386-73-4), Fluconazole-cis (112839-32-4), Thiabendazole (148-79-8), Quinconazole (103970-75-8), Fenpiclonil (74738-17-3), Fludioxonil (131341-86-1), Cyprodinil (121552-61-2), Mepanipyrim (110235-47-7), Pyrimethanil (53112-28-0), Aldimorph (91315-15-0), Dodemorph (1593-77-7), Fenpropimorph (67564-91-4), Tridemorph (81412-43-3), Fenpropidin (67306-00-7), Spiroxamine (118134-30-8), Isopyrazam (881685-58-1), Sedaxane (874967-67-6), Bixafen (581809-46-3), Penthiopyrad (183675-82-3), Fluxapyroxad (907204-31-3), Boscalid (188425-85-6), Penflufen (494793-67-8), Fluopyram (658066-35-4), Mandipropamid (374726-62-2), Benthiavalicarb (413615-35-7), Dimethomorph (110488-70-5), Chlorothalonil (1897-45-6), Fluazinam (79622-59-6), Dithianon (3347-22-6), Metrafenone (220899-03-6), Tricyclazole (41814-78-2), Mefenoxam (70630-17-0), Metalaxyl (57837-19-1), Acibenzolar (126448-41-7) (Acibenzolar-5-methyl (126448-41-7)), Mancozeb (8018-01-7), Ametoctradine (865318-97-4) Ipconazole (125225-28-7), Amisulbrom (348635-87-0), Cyflufenamid (180409-60-3), Ethaboxam (16650-77-3), Fluopicolide (239110-15-7), Fluthianil (304900-25-2), Isotianil (224049-04-1), Proquinazid (189278-12-4), Valiphenal (283159-90-0), 1-methyl-cyclopropene (3100-04-7), Trifloxystrobin (141517-21-7), Sulfur (7704-34-9), Copper ammoniumcarbonate (CAS 33113-08-5); Copper oleate (CAS 1120-44-1); Folpet (133-07-3), Quinoxyfen (124495-18-7), Captan (133-06-2), Fenhexamid (126833-17-8), Glufosinate and its salts (51276-47-2, 35597-44-5 (S-isomer)), Glyphosate (1071-83-6) and its salts (69254-40-6 (Diammonium), 34494-04-7 (Dimethylammonium), 38641-94-0 (Isopropylammonium), 40465-66-5 (Monoammonium), 70901-20-1 (Potassium), 70393-85-0 (Sesquisodium), 81591-81-3 (Trimesium)), 1,3-Dimethyl-1H-pyrazole-4-carboxylic acid (2-dichloromethylene-3-ethyl-1-methyl-indan-4-yl)-amide, 1,3-Dimethyl-1H-pyrazole-4-carboxylic acid (4'-methylsulfanyl-biphenyl-2-yl)-amide, 1,3-Dimethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichloro-phenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine.

Another aspect of invention is related to the use of a compound of formula I or of a preferred individual compound as above-defined, of a composition comprising at least one compound of formula I or at least one preferred individual compound as above-defined, or of a fungicidal mixture comprising at least one compound of formula I or at least one preferred individual compound as above-defined, in admixture with other fungicides, as described above, for controlling or preventing infestation of plants, e.g. useful plants such as crop plants, propagation material thereof, e.g. seeds, harvested crops, e.g. harvested food crops, or non-living materials by phytopathogenic microorganisms, preferably fungal organisms.

A further aspect of invention is related to a method of controlling or preventing an infestation of plants, e.g. useful plants such as crop plants, propagation material thereof, e.g. seeds, harvested crops, e.g. harvested food crops, or of non-living materials by phytopathogenic or spoilage microorganisms or organisms potentially harmful to man, especially fungal organisms, which comprises the application of a compound of formula I or of a preferred individual compound as above-defined as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, which comprises the application of a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, e.g. a composition containing the compound of formula I, and, if desired, a solid or liquid adjuvant or monomers for encapsulating the compound of formula I, may be prepared in a known manner, typically by intimately mixing and/or grinding the compound with extenders, for example solvents, solid carriers and, optionally, surface active compounds (surfactants).

The agrochemical formulations and/or compositions will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting examples illustrate the above-described invention in more detail.

EXAMPLE 1

This Example Illustrates the Preparation of 1,2,3,4-tetrahydro-naphthalene-1-carboxylic acid (2-{1-[2-(5-methyl-3-trifluoromethyl-pyrazol-1-yl)-acetyl]-piperidin-4-yl}-thiazol-4-yl)amide (Compound No. 1.g.011)

a) Preparation of 2-{1-[2-(5-methyl-3-trifluoromethyl-pyrazol-1-yl)-acetyl]-piperidin-4-yl}-thiazole-4-carboxylic acid ethyl ester To a solution of (5-methyl-3-trifluoromethyl-pyrazol-1-yl)-acetic acid (9.1 g, 36.1 mmol) in DMF (100 mL) is added diisopropylethylamine (45 mL, 216 mmol), followed by O-(benzotriazol-1-yl)-N,N,N',N'-tetramethyluronium tetrafluoroborate (15.5 g, 39.7 mmol). After stirring 15 min at RT, 2-piperidin-4-yl-thiazole-4-carboxylic acid ethyl ester hydrochloride (10 g, 36.1 mmol) is added to the reaction mixture. After stirring overnight at RT, solvent is evaporated and the resulting yellow oil is dissolved in ethylacetate (300 mL), washed with saturated aqueous sodium bicarbonate solution (300 mL), 1M HCl solution (300 mL), and brine (100 mL). The organic layer is dried over sodium sulfate, filtered, and evaporated under reduced pressure. The crude mixture is purified by column chromatography on silica gel (dichloromethane/methanol 10:1) to give 2-{1-[2-(5-methyl-3-trifluoromethyl-pyrazol-1-yl)-acetyl]-piperidin-4-yl}-thiazole-4-carboxylic acid ethyl ester (13.6 g, 88%). $^1$H-NMR (400 MHz, CDCl$_3$): δ=1.40 (t, 3H), 1.70-1.85 (m, 2H), 2.16-2.30 (m, 2H), 2.32 (s, 3H), 2.79-2.89 (m, 1H), 3.22-3.43 (m, 1H), 4.03-4.12 (m, 1H), 4.42 (q, 3H), 4.54-4.69 (m, 1H), 4.93-5.08 (2d, 2H (diastereotopic)), 6.35 (s, 1H), 8.10 (br, 1H). MS: m/z=209 (M+1).

b) Preparation of 2-{1-[2-(5-methyl-3-trifluoromethyl-pyrazol-1-yl)-acetyl]-piperidin-4-yl}-thiazole-4-carboxylic acid To a solution of 2-{1-[2-(5-methyl-3-trifluoromethyl-pyrazol-1-yl)-acetyl]-piperidin-4-yl}-thiazole-4-carboxylic acid ethyl ester (2.67 g, 6.2 mmol) in THF (20 mL) is added aqueous solution of sodium hydroxide (2 M, 4.65 mL, 9.3 mmol) at RT. After stirring 3 h at RT, the reaction mixture is acidified with 2M aqueous solution of HCl until pH 2-3, and the solution is extracted with ethylacetate (20 mL). The aqueous layer is re-extracted with ethylacetate (20 mL) and the combined organic layers are washed with brine (10 mL), dried over sodium sulfate, filtered, and evaporated under reduced pressure to give 2-{1-[2-(5-methyl-3-trifluoromethyl-pyrazol-1-yl)-acetyl]-piperidin-4-yl}-thiazole-4-carboxylic acid (2.33 g, 94%), which can be used in the next step without further purification. $^1$H-NMR (400 MHz, d$_6$-acetone): δ=1.69-1.82 (m, 1H), 1.87-2.02 (m, 1H), 2.16-2.37 (m, 2H), 2.38 (s, 3H), 2.89-2.99 (m, 1H), 3.38-3.48 (m, 2H), 4.14-4.22 (m, 1H), 4.50-4.69 (m, 1H), 5.20-5.36 (2d, 2H (diastereotopic)), 6.41, (s, 1H), 8.34 (s, 1H). MS: m/z=403 (M+1).

c) Preparation of 2-{1-[2-(5-methyl-3-trifluoromethyl-pyrazol-1-yl)-acetyl]-piperidin-4-yl}-thiazol-4-yl)-carbamic acid tert-butyl ester To a solution of 2-{1-[2-(5-methyl-3-trifluoromethyl-pyrazol-1-yl)-acetyl]-piperidin-4-yl}-thiazole-4-carboxylic acid (9.95 g, 24.74 mmol) in tert-butanol (90 mL) is added triethylamine (8.2 mL, 56.9 mmol). After stirring 30 min. at RT, diphenylphosphoryl azide (10.9 mL, 49.5 mmol) is added and the reaction mixture is divided in 6 portions and each portion was irradiated under microwave (100° C., 15 min.). After cooling to RT, all portions are combined and water (3 mL) is added to the reaction mixture and stirred for 30 minutes. Acetonitrile (40 mL) is then added, followed by addition of basic Amberlyst A21. After stirring overnight at RT, the resin is filtered off, and solvents are evaporated under reduced pressure. The residue is purified by column chromatography on silica gel (ethyl acetate/cyclohexane 7:3) to give 2-{1-[2-(5-methyl-3-trifluoromethyl-pyrazol-1-yl)-acetyl]-piperidin-4-yl}-thiazol-4-yl)-carbamic acid tert-butyl ester (9.6 g, 82%). $^1$H-NMR (400 MHz, CDCl$_3$): δ=1.53 (s, 9H), 1.68-1.78 (m, 2H), 2.08-2.19 (m, 2H), 2.32 (s, 3H), 2.85-2.95 (m, 1H), 3.10-3.20 (m, 1H), 3.23-3.34 (m, 1H), 3.97-4.04 (m, 1H), 4.50-4.58 (m, 1H), 4.93-5.05 (2d, 2H, diastereotopic protons), 6.33 (s, 1H), 7.10 (br, 1H), 7.30 (s, 1H). MS: m/z=474 (M+1).

d) Preparation of 1-[4-(4-amino-thiazol-2-yl)-piperidin-1-yl]-2-(5-methyl-3-trifluoromethyl-pyrazol-1-yl)-ethanone To a solution of 2-{1-[2-(5-methyl-3-trifluoromethyl-pyrazol-1-yl)-acetyl]-piperidin-4-yl}-thiazol-4-yl)-carbamic acid tert-butyl ester (9.6 g, 20.3 mmol) is added a solution of 4M HCl in dioxane (50 mL, 203 mmol)) at RT. After stirring 2 days at RT, the solvent is evaporated under reduced pressure. The resulting yellowish foam is triturated with diethylether, and filtered to give 1-[4-(4-Amino-thiazol-2-yl)-piperidin-1-yl]-2-(5-methyl-3-trifluoromethyl-pyrazol-1-yl)-ethanone hydrochloride salt, which is suspended in aqueous saturated sodium bicarbonate (500 mL). After stirring 30 min. at RT, the reaction mixture is extracted with ethylacetate (500 mL). The combined organic layers are washed with water (100 mL) and brine (100 mL), filtered, dried over sodium sulfate, and evaporated under reduced pressure to give 1-[4-(4-amino-thiazol-2-yl)-piperidin-1-yl]-2-(5-methyl-3-trifluoromethyl-pyrazol-1-yl)-ethanone (5.63 g, 74%). $^1$H-NMR (400 MHz, CDCl$_3$): δ=1.65-1.80 (m, 2H), 2.08-2.20 (m, 2H), 2.31 (s, 3H), 2.81-2.91 (m, 1H), 3.08-3.18 (m, 1H), 3.21-3.32 (m, 1H), 3.95-4.08 (m, 3H), 4.50-4.59 (m, 1H), 4.93-5.04 (2d, 2H, diastereotopic protons), 5.84 (s, 1H), 6.32 (s, 1H). MS: m/z=374 (M+1).

e) Preparation of 1,2,3,4-tetrahydro-naphthalene-1-carboxylic acid (2-{1-[2-(5-methyl-3-trifluoromethyl-pyrazol-1-yl)-acetyl]-piperidin-4-yl}-thiazol-4-yl)amide (Compound No. I.g.011)

To a solution of 1-[4-(4-amino-thiazol-2-yl)-piperidin-1-yl]-2-(5-methyl-3-trifluoromethyl-pyrazol-1-yl)-ethanone (120 mg, 0.32 mmol) and diisopropylethylamine (0.2 mL, 0.96 mmol) in dichloromethane (5 mL) is added dropwise a solution of 1,2,3,4-tetrahydro-naphthalene-1-carbonyl chloride (74 mg, 0.38 mmol) in dichloromethane (3 mL) at 0° C. After stirring overnight at RT, the solvent is evaporated and the residue is purified by flash chromatography on silica gel (ethylacetate/cyclohexane 1:1) to give 1,2,3,4-tetrahydro-naphthalene-1-carboxylic acid (2-{1-[2-(5-methyl-3-trifluoromethyl-pyrazol-1-yl)-acetyl]-piperidin-4-yl}-thiazol-4-yl)amide (Compound No. 1.g.011, 82 mg, 48%). M.p.=179.2-181.3° C. $^1$H-NMR (400 MHz, CDCl$_3$): δ=1.60-1.75 (m, 3H), 1.81-1.89 (m, 2H), 2.05-2.15 (m, 2H), 2.31 (s, 3H), 2.32-2.40 (m, 1H), 2.77-2.94 (m, 3H), 3.05-3.18 (m, 1H), 3.19-3.29 (m, 1H), 3.87 (t, 1H), 3.95-4.04 (m, 1H), 4.50-4.59 (m, 1H), 4.90-5.06 (2d, 2H, diastereotopic protons), 6.32 (s, 1H), 7.25-7.30 (m, 4H), 7.49 (s, 1H), 7.79 (br, 1H). MS: m/z=532 (M+1).

EXAMPLE 2

This Example Illustrates the Preparation of 2-{1-[2-(5-Methyl-3-trifluoromethyl-pyrazol-1-yl)-acetyl]-piperidin-4-yl}-thiazol-4-yl)-carbamic acid phenyl ester (Compound No. I.g.023)

a) Preparation of 2-{1-[2-(5-methyl-3-trifluoromethyl-pyrazol-1-yl)-acetyl]-piperidin-4-yl}-thiazol-4-yl)-carbamic acid phenyl ester (Compound No. I.g.023)

To a solution of 1-[4-(4-amino-thiazol-2-yl)-piperidin-1-yl]-2-(5-methyl-3-trifluoromethyl-pyrazol-1-yl)-ethanone (80 mg, 0.21 mmol) in dichloromethane (5 mL) is added diisopropylethylamine (0.053 mL, 0.25 mmol), and subsequently phenylchloroformate (0.033 mL, 0.21 mmol) at 0° C. After stirring overnight at RT, solvents are evaporated under reduced pressure and the residue is purified by column chromatography on silica gel (ethyl acetate/heptane 7:3) to give 2-{1-[2-(5-methyl-3-trifluoromethyl-pyrazol-1-yl)-acetyl]-piperidin-4-yl}-thiazol-4-yl)-carbamic acid phenyl ester (Compound No. I.g.023, 71 mg, 67%). $^1$H-NMR (400 MHz, CDCl$_3$): δ=1.57-1.78 (m, 2H), 2.08-2.19 (m, 2H), 2.22 (s, 3H), 2.75-2.81 (m, 1H), 3.05-3.20 (m, 2H), 3.95-3.99 (m, 1H), 4.44-4.52 (m, 1H), 4.83-4.98 (2d, 2H, diastereotopic protons), 6.25 (s, 1H), 7.05-7.20 (m, 3H), 7.29-7.38 (m, 2H), 7.95 (br, 1H). MS: m/z=494 (M+1).

EXAMPLE 3

This Example Illustrates the Preparation of 1-(2-{1-[2-(5-Methyl-3-trifluoromethyl-pyrazol-1-yl)-acetyl]-piperidin-4-yl}-thiazol-4-yl)-3-phenyl-urea (Compound No. I.g.024)

a) Preparation of 1-(2-{1-[2-(5-methyl-3-trifluoromethyl-pyrazol-1-yl)-acetyl]-piperidin-4-yl}-thiazol-4-yl)-3-phenyl-urea (Compound No. I.g.024)

To a solution of 1-[4-(4-amino-thiazol-2-yl)-piperidin-1-yl]-2-(5-methyl-3-trifluoromethyl-pyrazol-1-yl)-ethanone (100 mg, 0.27 mmol) in THF (5 mL) is added dropwise a solution of phenylisocyanate (30 µL, 0.28 mmol) in THF (1 mL) at 0° C. After stirring overnight at RT, methanol (1 mL) is added to the reaction mixture. After stirring 15 min. at RT, the solvents are evaporated and the residue was triturated with diethylether (5 mL) to induce precipitation. The resulting solid is filtered and dried under vacuum to give 1-(2-{1-[2-(5-methyl-3-trifluoromethyl-pyrazol-1-yl)-acetyl]-piperidin-4-yl}-thiazol-4-yl)-3-phenyl-urea as beige solid (Compound No. I.g.024, 105 mg, 79%). M.p.=192.6° C. $^1$H-NMR (400 MHz, CDCl$_3$): δ=$^1$H-NMR (MeOD): d=1.65 (m, 1H), 1.80 (m, 1H), 2.40 (m, 2H), 2.30 (s, 3H), 2.98 (m, 1H), 3.30 (m, 1H), 3.39 (m, 1H), 4.10 (m, 1H), 4.52 (m, 1H), 5.22 (2d, 2H, diastereotopic), 6.42 (s, 1H), 7.05 (t, 1H), 7.09 (s, 1H), 7.26-7.45 (m, 6H). MS: m/z=494 (M+1).

EXAMPLE 4

This Example Illustrates the Preparation of N-(2-{1-[2-(5-methyl-3-trifluoromethyl-pyrazol-1-yl)-acetyl]-piperidin-4-yl}-thiazol-4-yl)-C-phenyl-methanesulfonamide (Compound No. I.g.025)

a) Preparation of N-(2-{1-[2-(5-methyl-3-trifluoromethyl-pyrazol-1-yl)-acetyl]-piperidin-4-yl}-thiazol-4-yl)-benzenesulfonamide (Compound No. I.g.025)

To a solution of 1-[4-(4-amino-thiazol-2-yl)-piperidin-1-yl]-2-(5-methyl-3-trifluoromethyl-pyrazol-1-yl)-ethanone (100 mg, 0.04 mmol) in dimethylacetamide (0.8 mL) is added diisopropylethylamine (8.6 µL, 0.28 mmol), followed by benzenesulfonyl chloride (8.8 mg, 0.05 mmol) at RT. After stirring 15 min at 60° C., the reaction mixture is purified directly by preparative HPLC to give N-(2-{1-[2-(5-methyl-3-trifluoromethyl-pyrazol-1-yl)-acetyl]-piperidin-4-yl}-thiazol-4-yl)-benzenesulfonamide (Compound No. I.g.025). MS: m/z=514 (M+1).

EXAMPLE 5

This Example Illustrates the Preparation of N-(2-{1-[2-(2,5-Dimethyl-phenyl)-acetyl]-piperidin-4-yl}-thiazol-4-yl)-2-phenyl-propionamide (Compound No. I.g.141)

a) Preparation of 2-{1-[2-(2,5-dimethyl-phenyl)-acetyl]-piperidin-4-yl}-thiazole-4-carboxylic acid ethyl ester To a solution of 2,5-dimethylphenylacetic acid (5.45 g, 27.4 mmol) in DMF (80 mL) is added diisopropylethylamine (85.4 mL, 411.32 mmol), followed by O-(benzotriazol-1-yl)-N,N,N',N'-tetramethyluronium tetrafluoroborate (12.8 g, 32.9 mmol) at 0° C. After stirring 15 min at RT, 2-piperidin-4-yl-thiazole-4-carboxylic acid ethyl ester (6.59 g, 27.4 mmol) is added to the reaction mixture. After stirring overnight at RT, solvent is evaporated and the resulting yellow oil is dissolved in ethylacetate (500 mL), washed with aqueous saturated sodium bicarbonate solution (500 mL) and the aqueous phase is re-extracted with ethylacetate (100 mL). The combined organic layers are washed with 0.5M HCl solution (400 mL) and brine (400 mL), dried over sodium sulfate, filtered, and evaporated under reduced pressure to give 2-{1-[2-(2,5-dimethyl-phenyl)-acetyl]-piperidin-4-yl}-thiazole-4-carboxylic acid ethyl ester (10.46 g, 98%), which can be used in the next step without further purification. $^1$H-NMR (400 MHz, CDCl$_3$): δ=1.41 (t, 3H), 1.52-1.82 (m, 2H), 2.10-2.22 (m, 2H), 2.25 (s, 3H), 2.30 (s, 3H), 2.73-2.86 (m, 1H), 3.08-3.22 (m, 1H), 3.29-3.40 (m, 1H), 3.68 (s, 2H), 3.8-3.95 (m, 1H), 4.38-4.42 (q, 2H), 4.73-4.88 (m, 1H), 6.96 (s, 1H), 6.98-7.01 (d, 1H), 7.08 (d, 1H), 8.10 (s, 1H). MS: m/z=387 (M+1).

b) Preparation of 2-{1-[2-(2,5-dimethyl-phenyl)-acetyl]-piperidin-4-yl}-thiazole-4-carboxylic acid To a solution of 2-{1-[2-(2,5-dimethyl-phenyl)-acetyl]-piperidin-4-yl}-thiazole-4-carboxylic acid ethyl ester (10.46 g, 27.06 mmol) in THF (30 mL) is added aqueous solution of sodium hydroxide (2 M, 20.3 mL) at RT. After stirring 3 h at RT, the reaction mixture is acidified with aqueous solution of HCl (2 M) until pH 2-3, and ethylacetate (30 mL) is added to the reaction mixture, and layers are separated. The aqueous layer is extracted with ethyl acetate (20 mL) and the combined organic layers are washed with brine (10 mL), dried over sodium sulafte, filtered, and evaporated under reduced pressure to give 2-{1-[2-(2,5-dimethyl-phenyl)-acetyl]-piperidin-4-yl}-thiazole-4-carboxylic acid (5.9 g, 60.8%), which can be used in the next step without further purification. $^1$H-NMR (400 MHz, d$_6$-DMSO): δ=1.55-1.65 (m, 2H), 2.01-2.12 (m, 2H), 2.15 (s, 3H), 2.22 (s, 3H), 2.77-2.86 (m, 1H), 3.18-3.29 (m, 1H), 3.65 (d, 2H), 3.98-4.07 (m, 1H), 4.45-4.53 (m, 1H), 6.90 (s, 1H), 6.92 (s, 1H), 6.93 (s, 1H), 7.04 (d, 1H), 8.49 (br, 1H), 12.95 (s, 1H). MS: m/z=359 (M+1).

c) Preparation of (2-{1-[2-(2,5-dimethyl-phenyl)-acetyl]-piperidin-4-yl}-thiazol-4-yl)-carbamic acid tert-butyl ester To a solution of 2-{1-[2-(2,5-dimethyl-phenyl)-acetyl]-piperidin-4-yl}-thiazole-4-carboxylic acid (5.65 g, 15.76 mmol) in tert-butanol (60 mL) is added triethylamine (5.2 mL, 36.2 mmol). After stirring 30 min. at RT, diphenylphosphoryl azide (6.9 mL, 31.5 mmol) is added and the reaction mixture is divided in 4 portions and each portion is irradiated under microwave (100° C., 15 min.). After cooling to RT, all portions are combined and water (1 mL) is added to the reaction mixture and stirred for 30 minutes. Acetonitrile (50 mL) is then added, followed by addition of basic Amberlyst A21. After stirring overnight at RT, the resin is filtered off, and solvents are evaporated under reduced pressure. The remainder is purified by column chromatography on silica gel (ethyl acetate/cyclohexane 7:3) to give (2-{1-[2-(2,5-dimethyl-phenyl)-acetyl]-piperidin-4-yl}-thiazol-4-yl)-carbamic acid tert-butyl ester (4.93 g, 73%). $^1$H-NMR (400 MHz, CDCl$_3$): δ=1.53 (s, 9H), 1.53-1.61 (m, 1H), 1.67-1.79 (m, 1H), 1.95-2.04 (m, 1H), 2.08-2.14 (m, 1H), 2.25 (s, 3H), 2.30 (s, 3H), 2.80-2.90 (m, 1H), 3.06-3.20 (m, 2H), 3.68 (s, 2H), 3.80-3.89 (m, 1H), 4.68-4.74 (m, 1H), 6.95 (s, 1H), 6.98 (d, 1H), 7.07 (d, 1H), 7.23 (s, 1H). MS: m/z=430 (M+1).

d) Preparation of 1-[4-(4-amino-thiazol-2-yl)-piperidin-1-yl]-2-(2,5-dimethyl-phenyl)-ethanone To a solution of (2-{1-[2-(2,5-dimethyl-phenyl)-acetyl]-piperidin-4-yl}-thiazol-4-yl)-carbamic acid tert-butyl ester (5.65 g, 13.15 mmol) is added a solution of 4M HCl in dioxane (35 mL) at RT. After stirring 3 days at RT, the solvent is evaporated under reduce pressure. The resulting solid is triturated with diethylether, and filtered to give 1-[4-(4-amino-thiazol-2-yl)piperidin-1-yl]-2-(2,5-dimethyl-phenyl)-ethanone hydrochloride salt, which is suspended in aqueous saturated sodium bicarbonate (500 mL). After stirring 30 min at RT, the reaction mixture is extracted with ethyl acetate (500 mL). The combined organic layers are washed with water (100 mL) and brine (100 mL), filtered, dried over sodium sulfate, and evaporated under reduced pressure to give 1-[4-(4-amino-thiazol-2-yl)-piperidin-1-yl]-2-(2,5-dimethyl-phenyl)-ethanone (3.27 g, 75%). $^1$H-NMR (400 MHz, CDCl$_3$): δ=1.53-1.61 (m, 1H), 1.67-1.79 (m, 1H), 1.95-2.04 (m, 1H), 2.08-2.13 (m, 1H), 2.25 (s, 3H), 2.30 (s, 3H), 2.78-2.88 (m, 1H), 3.06-3.20 (m, 2H), 3.68 (s, 2H), 3.80-3.89 (m, 1H), 4.05 (s, 1H), 4.68-4.74 (m, 1H), 6.95 (s, 1H), 6.98 (d, 1H), 7.07 (d, 1H), 7.23 (s, 1H). MS: m/z=330 (M+1). MS: m/z=330 (M+1).

e) Preparation of N-(2-{1-[2-(2,5-dimethyl-phenyl)-acetyl]-piperidin-4-yl}-thiazol-4-yl)-2-phenyl-propionamide (Compound No. I.g.141)

To a solution of (rac.)-2-phenylpropionic acid (46 mg, 0.30 mmol) and diisopropylethylamine (0.15 mL, 0.9 mmol) in acetonitrile (2 mL) is added benzotriazole-1-yl-oxy-tris-(dimethylamino)-phosphonium hexafluorophosphate (322 mg, 0.73 mmol) at RT. After stirring 30 min at RT, 1-[4-(4-amino-thiazol-2-yl)-piperidin-1-yl]-2-(2,5-dimethyl-phenyl)-ethanone (100 mg, 0.30 mmol) is added to the reaction mixture. After stirring overnight at RT, the solvent is evaporated and the residue is purified by flash chromatography on silica gel (ethylacetate/cyclohexane 1:1) to give N-(2-{1-[2-(2,5-dimethyl-phenyl)-acetyl]-piperidin-4-yl}-thiazol-4-yl)-2-phenyl-propionamide (Compound No. I.g.141, 19 mg, 13.4%). $^1$H-NMR (400 MHz, CDCl$_3$): δ=1.46-1.39 (m, 1H), 1.52 (d, 3H), 1.68-1.56 (m, 1H), 1.89-1.83 (m, 1H), 2.01-1.97 (m, 1H), 2.15 (s, 3H), 2.19 (s, 3H), 2.73-2.67 (m, 1H), 3.18-2.92 (m, 2H), 3.59 (s, 2H), 3.68-3.63 (q, 1H), 3.78-3.71 (m, 1H), 4.65-4.62 (m, 1H), 6.91-6.82 (m, 2H), 7.02-6.98 (m, 1H), 7.31-7.15 (m, 5H), 7.42 (s, 1H), 8.05 (br, 1H). MS: m/z=462 (M+1).

Table 1 below illustrates examples of individual compounds of formula I according to the invention.

TABLE 1

| individual compounds of formula I according to the invention | | | | |
|---|---|---|---|---|
| Compound No. | R$^1$ | A | Q | R$^9$ |
| 001 | 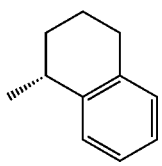 | —CH$_2$C(=O)— | —C(=O)— | |

TABLE 1-continued individual compounds of formula I according to the invention

| Compound No. | R¹ | A | Q | R⁹ |
|---|---|---|---|---|
| 002 | CF₃-pyrazole-N-CH₃, CH₃ | —CH₂C(=O)— | —C(=S)— | (S)-1,2,3,4-tetrahydronaphthalen-1-yl |
| 003 | CF₃-pyrazole-N-CH₃, CH₃ | —CH₂C(=O)— | —C(=O)O— | (S)-1,2,3,4-tetrahydronaphthalen-1-yl |
| 004 | CF₃-pyrazole-N-CH₃, CH₃ | —CH₂C(=O)— | —C(=O)NH— | (S)-1,2,3,4-tetrahydronaphthalen-1-yl |
| 005 | CF₃-pyrazole-N-CH₃, CH₃ | —CH₂C(=O)— | —SO₂— | (S)-1,2,3,4-tetrahydronaphthalen-1-yl |
| 006 | CF₃-pyrazole-N-CH₃, CH₃ | —CH₂C(=O)— | —C(=O)— | 2-methyl-6-chlorophenol |
| 007 | CF₃-pyrazole-N-CH₃, CH₃ | —CH₂C(=O)— | —C(=S)— | 2-methyl-6-chlorophenol |
| 008 | CF₃-pyrazole-N-CH₃, CH₃ | —CH₂C(=O)— | —C(=O)O— | 2-methyl-6-chlorophenol |
| 009 | CF₃-pyrazole-N-CH₃, CH₃ | —CH₂C(=O)— | —C(=O)NH— | 2-methyl-6-chlorophenol |

TABLE 1-continued
individual compounds of formula I according to the invention
| Compound No. | R¹ | A | Q | R⁹ |
|---|---|---|---|---|
| 010 | 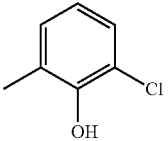 | —CH₂C(=O)— | —SO₂— | 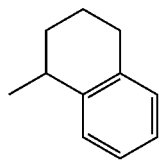 |
| 011 | 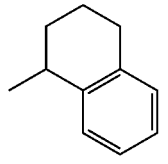 | —CH₂C(=O)— | —C(=O)— | 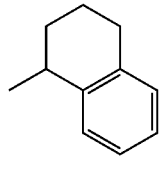 |
| 012 | 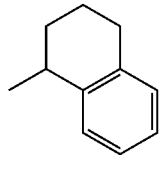 | —CH₂C(=O)— | —C(=S)— | 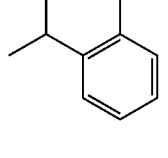 |
| 013 | 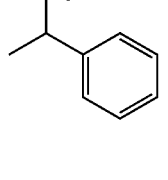 | —CH₂C(=O)— | —C(=O)O— | 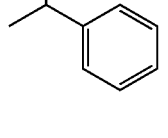 |
| 014 | (pyrazole-CF₃, CH₃) | —CH₂C(=O)— | —C(=O)NH— | (tetrahydronaphthyl) |
| 015 | (pyrazole-CF₃, CH₃) | —CH₂C(=O)— | —SO₂— | (tetrahydronaphthyl) |
| 016 | (pyrazole-CF₃, CH₃) | —CH₂C(=O)— | —C(=O)— | CH₃-CH-Ph |
| 017 | (pyrazole-CF₃, CH₃) | —CH₂C(=O)— | —C(=S)— | CH₃-CH-Ph |

TABLE 1-continued
individual compounds of formula I according to the invention
| Compound No. | R¹ | A | Q | R⁹ |
|---|---|---|---|---|
| 018 | 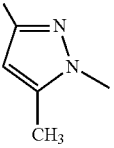 | —CH₂C(=O)— | —C(=O)O— | 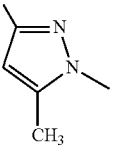 |
| 019 | 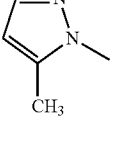 | —CH₂C(=O)— | —C(=O)NH— | 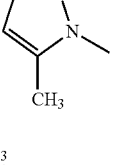 |
| 020 | 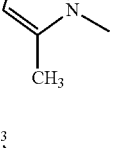 | —CH₂C(=O)— | —SO₂— | 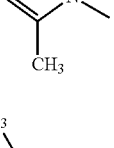 |
| 021 | 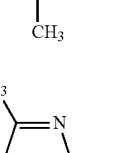 | —CH₂C(=O)— | —C(=O)— | 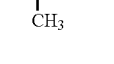 |
| 022 | | —CH₂C(=O)— | —C(=S)— | |
| 023 | | —CH₂C(=O)— | —C(=O)O— | |
| 024 | | —CH₂C(=O)— | —C(=O)NH— | |
| 025 | | —CH₂C(=O)— | —SO₂— | |

TABLE 1-continued individual compounds of formula I according to the invention

| Compound No. | R¹ | A | Q | R⁹ |
|---|---|---|---|---|
| 026 | 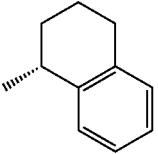 CF₃, CH₃ (pyrazole) | —CH₂C(=S)— | —C(=O)— | 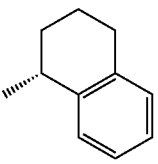 tetrahydronaphthyl |
| 027 | CF₃, CH₃ (pyrazole) | —CH₂C(=S)— | —C(=S)— | tetrahydronaphthyl |
| 028 | CF₃, CH₃ (pyrazole) | —CH₂C(=S)— | —C(=O)O— | tetrahydronaphthyl |
| 029 | CF₃, CH₃ (pyrazole) | —CH₂C(=S)— | —C(=O)NH— | tetrahydronaphthyl |
| 030 | CF₃, CH₃ (pyrazole) | —CH₂C(=S)— | —SO₂— | tetrahydronaphthyl |
| 031 | CF₃, CH₃ (pyrazole) | —CH₂C(=S)— | —C(=O)— | 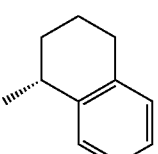 2-chloro-6-methylphenol |
| 032 | CF₃, CH₃ (pyrazole) | —CH₂C(=S)— | —C(=S)— | 2-chloro-6-methylphenol |
| 033 | CF₃, CH₃ (pyrazole) | —CH₂C(=S)— | —C(=O)O— | 2-chloro-6-methylphenol |

TABLE 1-continued
individual compounds of formula I according to the invention
| Compound No. | R¹ | A | Q | R⁹ |
|---|---|---|---|---|
| 034 | 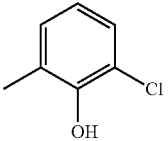 | —CH₂C(=S)— | —C(=O)NH— | 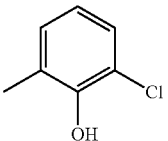 |
| 035 | 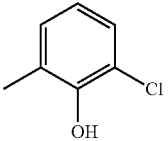 | —CH₂C(=S)— | —SO₂— | 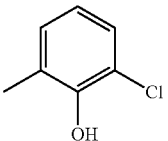 |
| 036 | 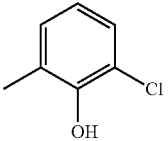 | —CH₂C(=S)— | —C(=O)— | 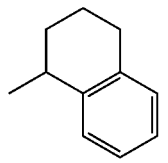 |
| 037 | 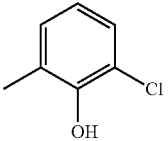 | —CH₂C(=S)— | —C(=S)— | 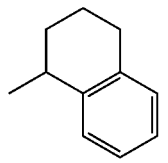 |
| 038 | 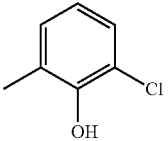 | —CH₂C(=S)— | —C(=O)O— | 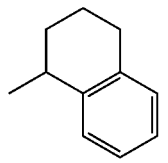 |
| 039 | 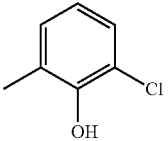 | —CH₂C(=S)— | —C(=O)NH— | 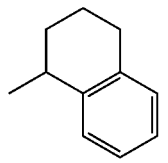 |
| 040 | 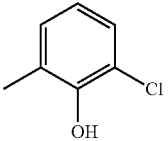 | —CH₂C(=S)— | —SO₂— | 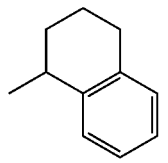 |
| 041 | 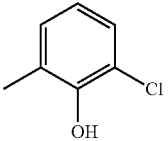 | —CH₂C(=S)— | —C(=O)— | 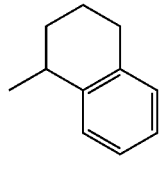 |

TABLE 1-continued
individual compounds of formula I according to the invention
| Compound No. | R¹ | A | Q | R⁹ |
|---|---|---|---|---|
| 042 | 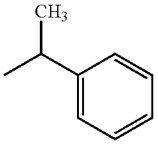 | —CH₂C(=S)— | —C(=S)— | 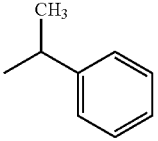 |
| 043 | 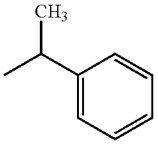 | —CH₂C(=S)— | —C(=O)O— | 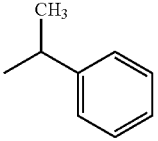 |
| 044 | 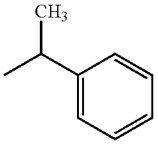 | —CH₂C(=S)— | —C(=O)NH— | 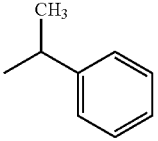 |
| 045 | 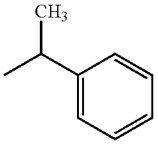 | —CH₂C(=S)— | —SO₂— | 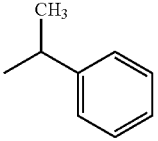 |
| 046 | 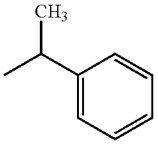 | —CH₂C(=S)— | —C(=O)— | 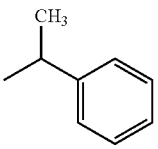 |
| 047 | 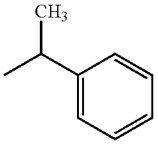 | —CH₂C(=S)— | —C(=S)— | 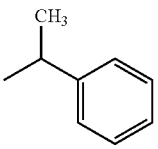 |
| 048 | 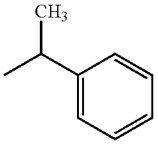 | —CH₂C(=S)— | —C(=O)O— | 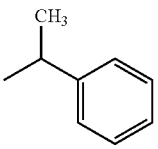 |
| 049 | 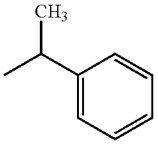 | —CH₂C(=S)— | —C(=O)NH— | 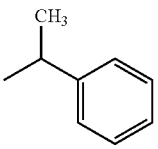 |

TABLE 1-continued
individual compounds of formula I according to the invention
| Compound No. | R¹ | A | Q | R⁹ |
|---|---|---|---|---|
| 050 | 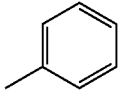 | —CH₂C(=S)— | —SO₂— | 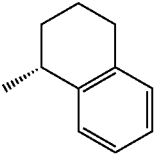 |
| 051 | 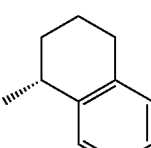 | —OC(=O)— | —C(=O)— | 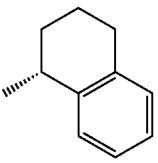 |
| 052 | 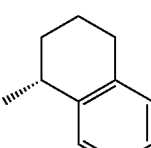 | —OC(=O)— | —C(=S)— | 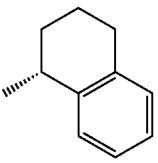 |
| 053 | 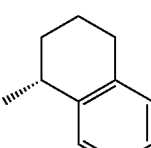 | —OC(=O)— | —C(=O)O— | 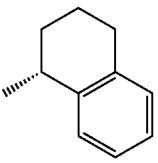 |
| 054 | 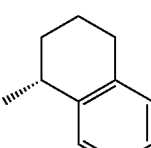 | —OC(=O)— | —C(=O)NH— | 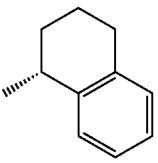 |
| 055 | 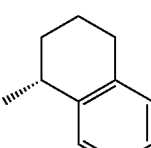 | —OC(=O)— | —SO₂— | 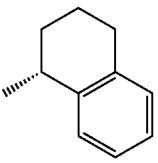 |
| 056 | 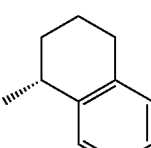 | —OC(=O)— | —C(=O)— | 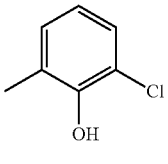 |
| 057 | 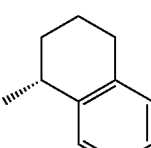 | —OC(=O)— | —C(=S)— | 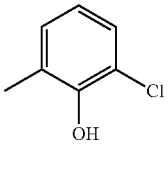 |

TABLE 1-continued individual compounds of formula I according to the invention

| Compound No. | R¹ | A | Q | R⁹ |
|---|---|---|---|---|
| 058 | 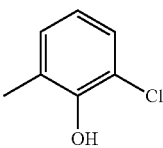 | —OC(=O)— | —C(=O)O— | 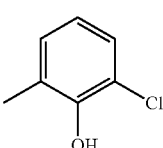 |
| 059 | 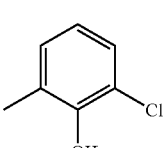 | —OC(=O)— | —C(=O)NH— | 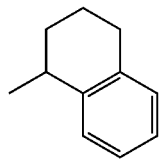 |
| 060 | 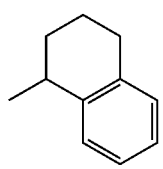 | —OC(=O)— | —SO₂— | 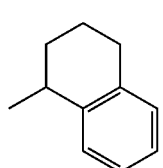 |
| 061 | 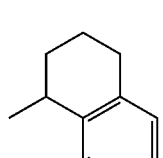 | —OC(=O)— | —C(=O)— | 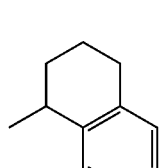 |
| 062 | (CF₃ pyrazole with N-CH₃, CH₃) | —OC(=O)— | —C(=S)— | (tetrahydronaphthyl) |
| 063 | (CF₃ pyrazole with N-CH₃, CH₃) | —OC(=O)— | —C(=O)O— | (tetrahydronaphthyl) |
| 064 | (CF₃ pyrazole with N-CH₃, CH₃) | —OC(=O)— | —C(=O)NH— | (tetrahydronaphthyl) |
| 065 | (CF₃ pyrazole with N-CH₃, CH₃) | —OC(=O)— | —SO₂— | (tetrahydronaphthyl) |

TABLE 1-continued
individual compounds of formula I according to the invention
| Compound No. | R¹ | A | Q | R⁹ |
|---|---|---|---|---|
| 066 | 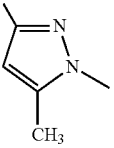 | —OC(=O)— | —C(=O)— | 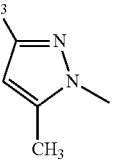 |
| 067 | 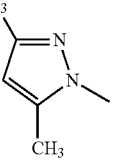 | —OC(=O)— | —C(=S)— | 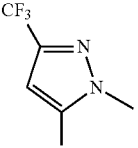 |
| 068 | 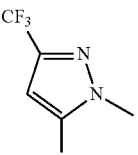 | —OC(=O)— | —C(=O)O— | 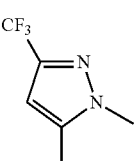 |
| 069 | 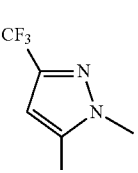 | —OC(=O)— | —C(=O)NH— | 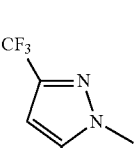 |
| 070 | CF₃ pyrazole with N—CH₃, CH₃ | —OC(=O)— | —SO₂— | isopropylphenyl |
| 071 | CF₃ pyrazole with N—CH₃, CH₃ | —OC(=O)— | —C(=O)— | methylphenyl |
| 072 | CF₃ pyrazole with N—CH₃, CH₃ | —OC(=O)— | —C(=S)— | methylphenyl |
| 073 | CF₃ pyrazole with N—CH₃, CH₃ | —OC(=O)— | —C(=O)O— | methylphenyl |

TABLE 1-continued
individual compounds of formula I according to the invention
| Compound No. | R¹ | A | Q | R⁹ |
|---|---|---|---|---|
| 074 | 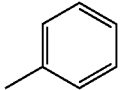 | —OC(=O)— | —C(=O)NH— | 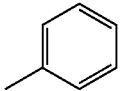 |
| 075 | 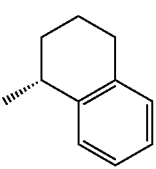 | —OC(=O)— | —SO₂— | 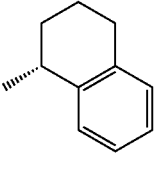 |
| 076 | 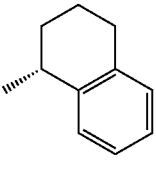 | —C(=O)— | —C(=O)— | 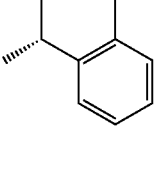 |
| 077 | 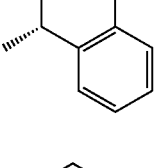 | —C(=O)— | —C(=S)— | 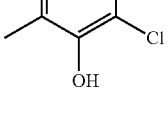 |
| 078 |  | —C(=O)— | —C(=O)O— |  |
| 079 |  | —C(=O)— | —C(=O)NH— |  |
| 080 |  | —C(=O)— | —SO₂— |  |
| 081 |  | —C(=O)— | —C(=O)— |  |

TABLE 1-continued
individual compounds of formula I according to the invention
| Compound No. | R¹ | A | Q | R⁹ |
|---|---|---|---|---|
| 082 | 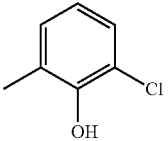 | —C(=O)— | —C(=S)— | 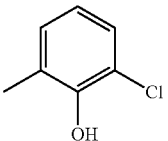 |
| 083 | 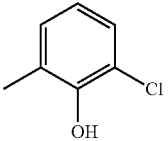 | —C(=O)— | —C(=O)O— | 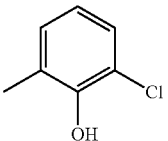 |
| 084 | 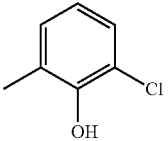 | —C(=O)— | —C(=O)NH— | 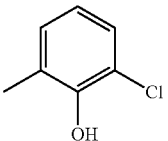 |
| 085 | 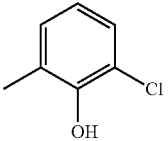 | —C(=O)— | —SO₂— | 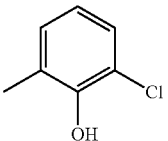 |
| 086 | 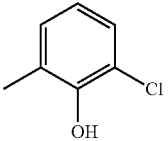 | —C(=O)— | —C(=O)— | 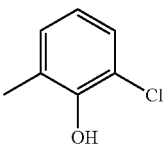 |
| 087 | 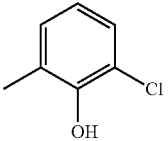 | —C(=O)— | —C(=S)— | 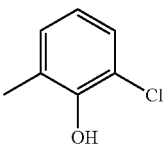 |
| 088 | 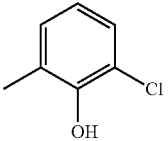 | —C(=O)— | —C(=O)O— | 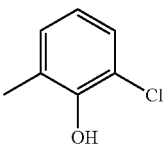 |
| 089 | 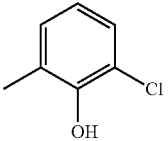 | —C(=O)— | —C(=O)NH— | 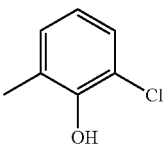 |

TABLE 1-continued
individual compounds of formula I according to the invention
| Compound No. | R¹ | A | Q | R⁹ |
|---|---|---|---|---|
| 090 | 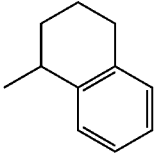 | —C(=O)— | —SO₂— | 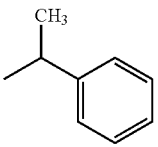 |
| 091 | 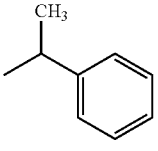 | —C(=O)— | —C(=O)— | 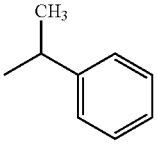 |
| 092 | 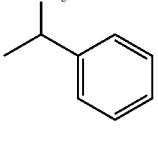 | —C(=O)— | —C(=S)— | 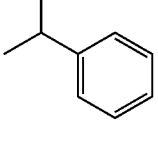 |
| 093 | 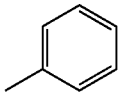 | —C(=O)— | —C(=O)O— | 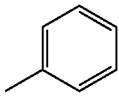 |
| 094 | CF₃-pyrazole-CH₃ | —C(=O)— | —C(=O)NH— | isopropylphenyl |
| 095 | CF₃-pyrazole-CH₃ | —C(=O)— | —SO₂— | isopropylphenyl |
| 096 | CF₃-pyrazole-CH₃ | —C(=O)— | —C(=O)— | methylphenyl |
| 097 | CF₃-pyrazole-CH₃ | —C(=O)— | —C(=S)— | methylphenyl |

TABLE 1-continued
individual compounds of formula I according to the invention
| Compound No. | R¹ | A | Q | R⁹ |
|---|---|---|---|---|
| 098 | 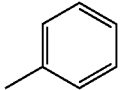 | —C(=O)— | —C(=O)O— | 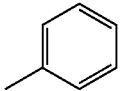 |
| 099 | 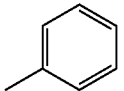 | —C(=O)— | —C(=O)NH— | 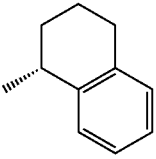 |
| 100 | 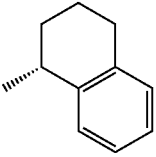 | —C(=O)— | —SO₂— | 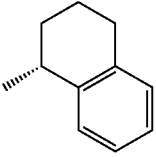 |
| 101 | 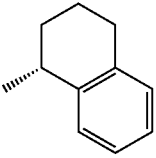 | —CH₂SO₂— | —C(=O)— | 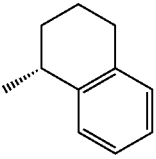 |
| 102 | CF₃ pyrazole-CH₃ | —CH₂SO₂— | —C(=S)— | tetrahydronaphthyl |
| 103 | CF₃ pyrazole-CH₃ | —CH₂SO₂— | —C(=O)O— | tetrahydronaphthyl |
| 104 | CF₃ pyrazole-CH₃ | —CH₂SO₂— | —C(=O)NH— | tetrahydronaphthyl |
| 105 | CF₃ pyrazole-CH₃ | —CH₂SO₂— | —SO₂— | tetrahydronaphthyl |

TABLE 1-continued
individual compounds of formula I according to the invention
| Compound No. | R¹ | A | Q | R⁹ |
|---|---|---|---|---|
| 106 | 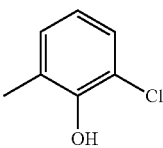 | —CH₂SO₂— | —C(═O)— | 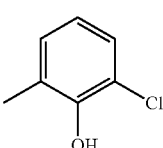 |
| 107 | 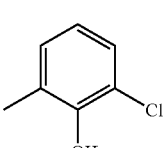 | —CH₂SO₂— | —C(═S)— | 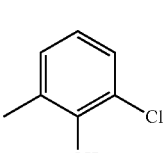 |
| 108 | 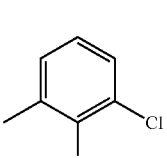 | —CH₂SO₂— | —C(═O)O— | 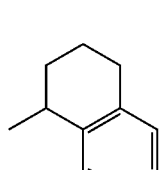 |
| 109 | 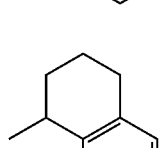 | —CH₂SO₂— | —C(═O)NH— | 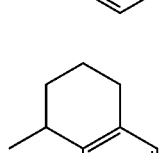 |
| 110 | | —CH₂SO₂— | —SO₂— | |
| 111 | | —CH₂SO₂— | —C(═O)— | |
| 112 | | —CH₂SO₂— | —C(═S)— | |
| 113 | | —CH₂SO₂— | —C(═O)O— | |

TABLE 1-continued
individual compounds of formula I according to the invention
| Compound No. | R¹ | A | Q | R⁹ |
|---|---|---|---|---|
| 114 | 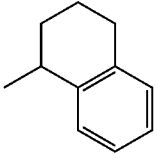 | —CH₂SO₂— | —C(=O)NH— | 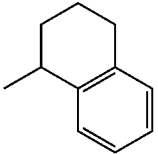 |
| 115 | 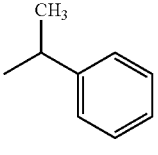 | —CH₂SO₂— | —SO₂— | 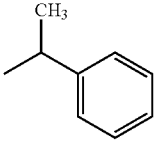 |
| 116 | 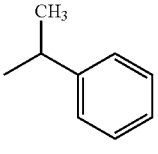 | —CH₂SO₂— | —C(=O)— | 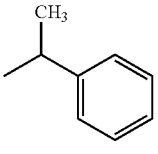 |
| 117 | 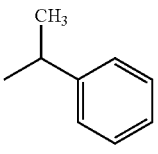 | —CH₂SO₂— | —C(=S)— | 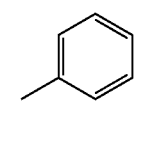 |
| 118 |  | —CH₂SO₂— | —C(=O)O— |  |
| 119 |  | —CH₂SO₂— | —C(=O)NH— |  |
| 120 |  | —CH₂SO₂— | —SO₂— |  |
| 121 |  | —CH₂SO₂— | —C(=O)— |  |

TABLE 1-continued
individual compounds of formula I according to the invention
| Compound No. | R¹ | A | Q | R⁹ |
|---|---|---|---|---|
| 122 | 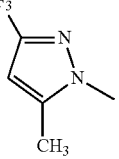 | —CH₂SO₂— | —C(=S)— | 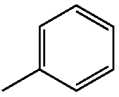 |
| 123 | 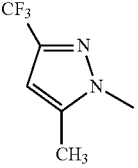 | —CH₂SO₂— | —C(=O)O— | 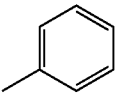 |
| 124 | 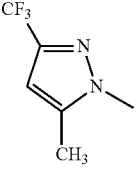 | —CH₂SO₂— | —C(=O)NH— | 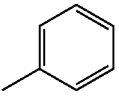 |
| 125 | 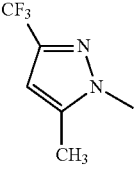 | —CH₂SO₂— | —SO₂— | 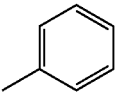 |
| 126 | 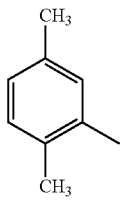 | —CH₂C(=O)— | —C(=O)— | 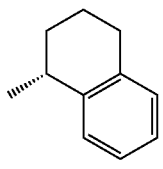 |
| 127 | 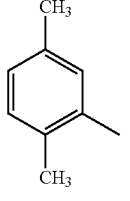 | —CH₂C(=O)— | —C(=S)— | 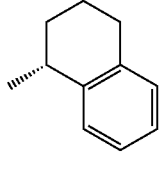 |
| 128 | 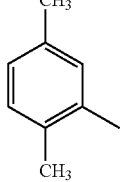 | —CH₂C(=O)— | —C(=O)O— | 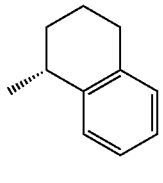 |

TABLE 1-continued
individual compounds of formula I according to the invention
| Compound No. | R¹ | A | Q | R⁹ |
|---|---|---|---|---|
| 129 | 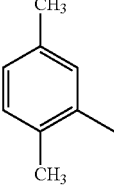 | —CH₂C(=O)— | —C(=O)NH— | 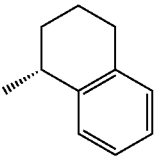 |
| 130 | 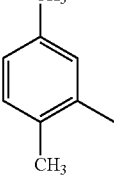 | —CH₂C(=O)— | —SO₂— | 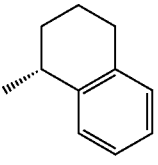 |
| 131 | 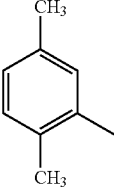 | —CH₂C(=O)— | —C(=O)— | 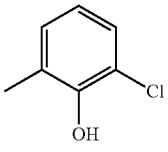 |
| 132 | 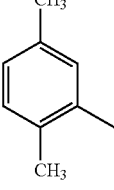 | —CH₂C(=O)— | —C(=S)— | 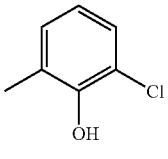 |
| 133 | 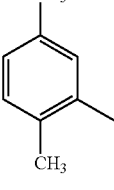 | —CH₂C(=O)— | —C(=O)O— | 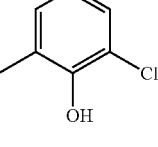 |
| 134 | 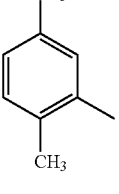 | —CH₂C(=O)— | —C(=O)NH— | 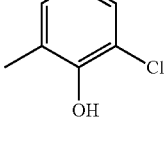 |
| 135 | 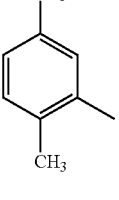 | —CH₂C(=O)— | —SO₂— | 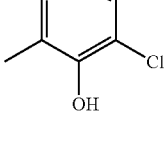 |

TABLE 1-continued
individual compounds of formula I according to the invention
| Compound No. | R¹ | A | Q | R⁹ |
|---|---|---|---|---|
| 136 | 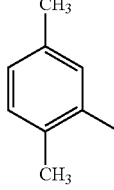 | —CH₂C(=O)— | —C(=O)— | 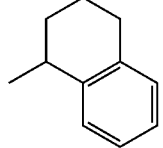 |
| 137 | 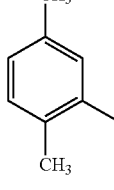 | —CH₂C(=O)— | —C(=S)— | 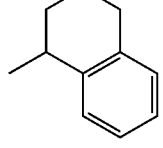 |
| 138 | 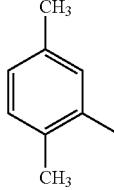 | —CH₂C(=O)— | —C(=O)O— | 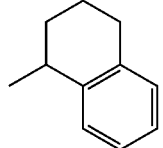 |
| 139 | 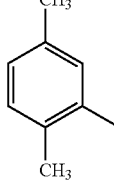 | —CH₂C(=O)— | —C(=O)NH— | 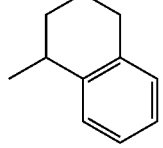 |
| 140 | 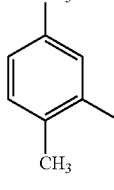 | —CH₂C(=O)— | —SO₂— | 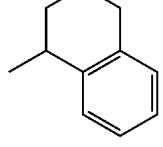 |
| 141 | 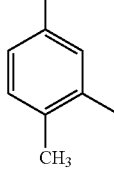 | —CH₂C(=O)— | —C(=O)— | 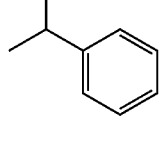 |
| 142 | 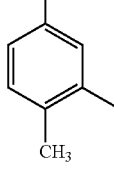 | —CH₂C(=O)— | —C(=S)— | 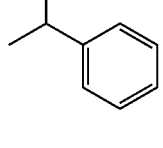 |

TABLE 1-continued individual compounds of formula I according to the invention

| Compound No. | R¹ | A | Q | R⁹ |
|---|---|---|---|---|
| 143 | 2,4-dimethylphenyl (CH₃, CH₃) | —CH₂C(=O)— | —C(=O)O— | 1-phenylethyl (CH₃) |
| 144 | 2,4-dimethylphenyl (CH₃, CH₃) | —CH₂C(=O)— | —C(=O)NH— | 1-phenylethyl (CH₃) |
| 145 | 2,4-dimethylphenyl (CH₃, CH₃) | —CH₂C(=O)— | —SO₂— | 1-phenylethyl (CH₃) |
| 146 | 2,4-dimethylphenyl (CH₃, CH₃) | —CH₂C(=O)— | —C(=O)— | tolyl |
| 147 | 2,4-dimethylphenyl (CH₃, CH₃) | —CH₂C(=O)— | —C(=S)— | tolyl |
| 148 | 2,4-dimethylphenyl (CH₃, CH₃) | —CH₂C(=O)— | —C(=O)O— | tolyl |
| 149 | 2,4-dimethylphenyl (CH₃, CH₃) | —CH₂C(=O)— | —C(=O)NH— | tolyl |

TABLE 1-continued
individual compounds of formula I according to the invention
| Compound No. | R¹ | A | Q | R⁹ |
|---|---|---|---|---|
| 150 | 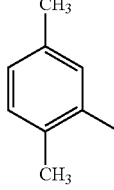 | —CH₂C(=O)— | —SO₂— | 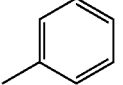 |
| 151 | 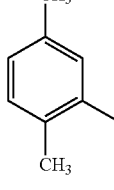 | —CH₂C(=S)— | —C(=O)— | 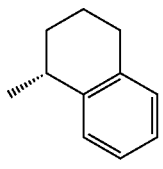 |
| 152 | 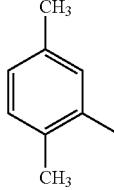 | —CH₂C(=S)— | —C(=S)— | 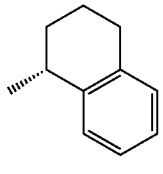 |
| 153 | 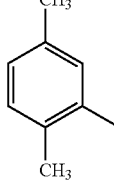 | —CH₂C(=S)— | —C(=O)O— | 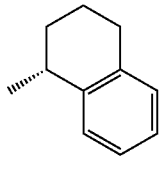 |
| 154 | 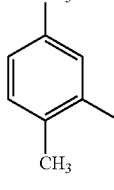 | —CH₂C(=S)— | —C(=O)NH— | 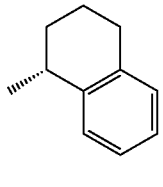 |
| 155 | 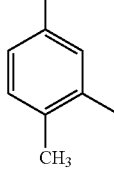 | —CH₂C(=S)— | —SO₂— | 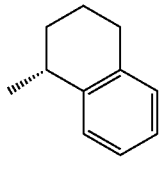 |
| 156 | 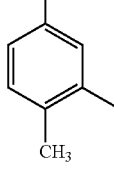 | —CH₂C(=S)— | —C(=O)— | 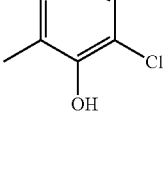 |

TABLE 1-continued
individual compounds of formula I according to the invention
| Compound No. | R¹ | A | Q | R⁹ |
|---|---|---|---|---|
| 157 | 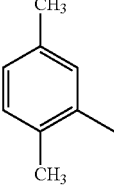 | —CH₂C(=S)— | —C(=S)— | 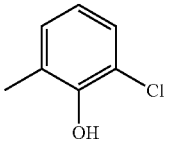 |
| 158 | 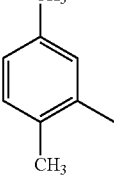 | —CH₂C(=S)— | —C(=O)O— | 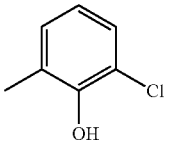 |
| 159 | 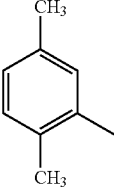 | —CH₂C(=S)— | —C(=O)NH— | 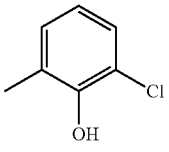 |
| 160 | 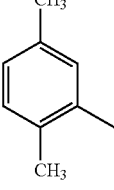 | —CH₂C(=S)— | —SO₂— | 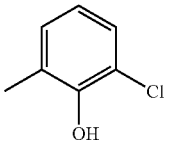 |
| 161 | 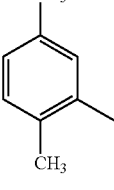 | —CH₂C(=S)— | —C(=O)— | 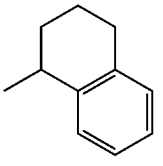 |
| 162 | 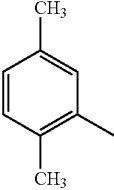 | —CH₂C(=S)— | —C(=S)— | 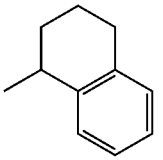 |
| 163 | 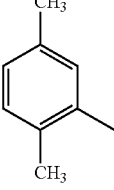 | —CH₂C(=S)— | —C(=O)O— | 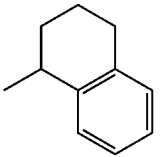 |

TABLE 1-continued
individual compounds of formula I according to the invention
| Compound No. | R¹ | A | Q | R⁹ |
|---|---|---|---|---|
| 164 | 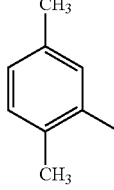 | —CH₂C(=S)— | —C(=O)NH— | 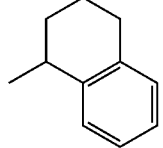 |
| 165 | 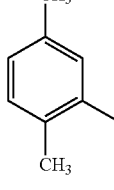 | —CH₂C(=S)— | —SO₂— | 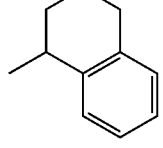 |
| 166 | 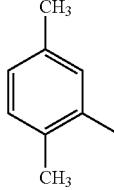 | —CH₂C(=S)— | —C(=O)— | 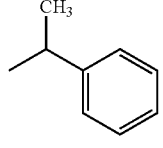 |
| 167 | 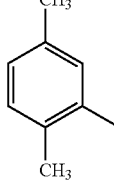 | —CH₂C(=S)— | —C(=S)— | 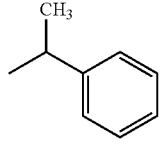 |
| 168 | 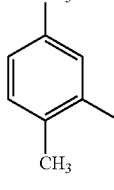 | —CH₂C(=S)— | —C(=O)O— | 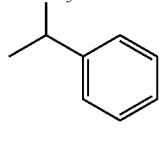 |
| 169 | 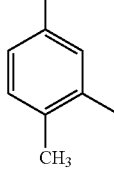 | —CH₂C(=S)— | —C(=O)NH— | 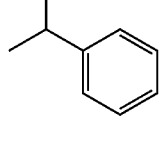 |
| 170 | 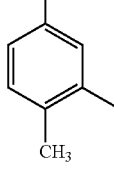 | —CH₂C(=S)— | —SO₂— | 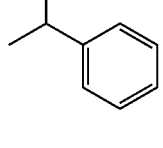 |

TABLE 1-continued
individual compounds of formula I according to the invention
| Compound No. | R¹ | A | Q | R⁹ |
|---|---|---|---|---|
| 171 | 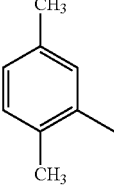 | —CH₂C(=S)— | —C(=O)— | 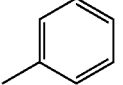 |
| 172 | 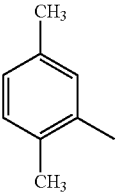 | —CH₂C(=S)— | —C(=S)— | 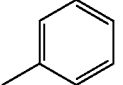 |
| 173 | 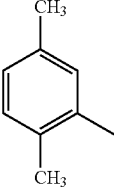 | —CH₂C(=S)— | —C(=O)O— | 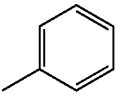 |
| 174 | 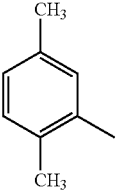 | —CH₂C(=S)— | —C(=O)NH— | 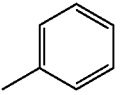 |
| 175 | 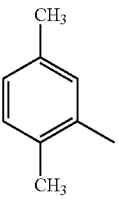 | —CH₂C(=S)— | —SO₂— | 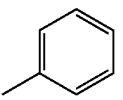 |
| 176 | 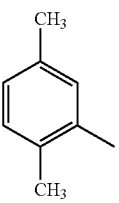 | —OC(=O)— | —C(=O)— | 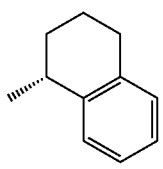 |
| 177 | 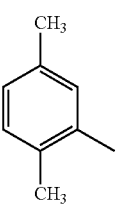 | —OC(=O)— | —C(=S)— | 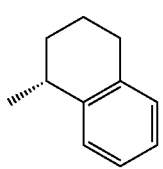 |

TABLE 1-continued
individual compounds of formula I according to the invention
| Compound No. | R¹ | A | Q | R⁹ |
|---|---|---|---|---|
| 178 | 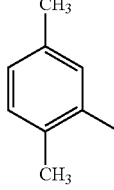 | —OC(=O)— | —C(=O)O— | 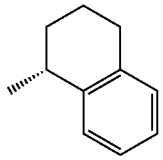 |
| 179 | 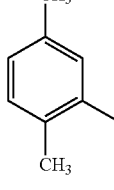 | —OC(=O)— | —C(=O)NH— | 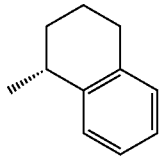 |
| 180 | 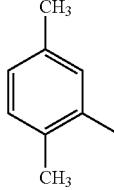 | —OC(=O)— | —SO₂— | 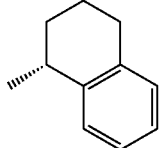 |
| 181 | 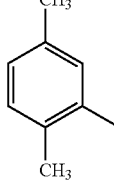 | —OC(=O)— | —C(=O)— | 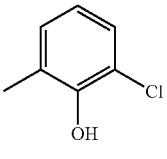 |
| 182 | 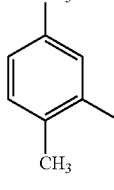 | —OC(=O)— | —C(=S)— | 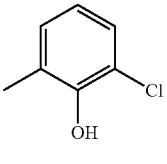 |
| 183 | 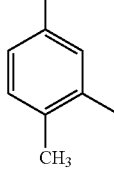 | —OC(=O)— | —C(=O)O— | 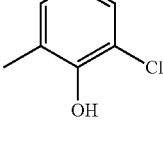 |
| 184 | 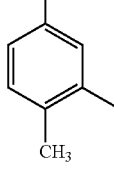 | —OC(=O)— | —C(=O)NH— | 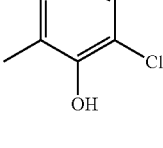 |

TABLE 1-continued
individual compounds of formula I according to the invention
| Compound No. | R¹ | A | Q | R⁹ |
|---|---|---|---|---|
| 185 | 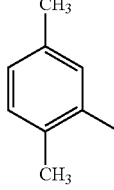 | —OC(=O)— | —SO₂— | 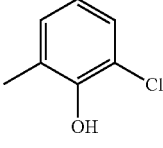 |
| 186 | 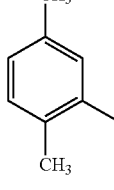 | —OC(=O)— | —C(=O)— | 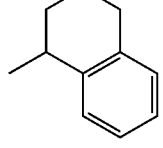 |
| 187 | 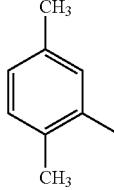 | —OC(=O)— | —C(=S)— | 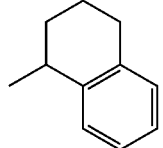 |
| 188 | 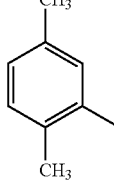 | —OC(=O)— | —C(=O)O— | 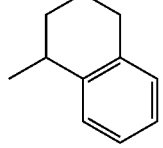 |
| 189 | 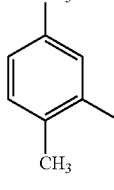 | —OC(=O)— | —C(=O)NH— | 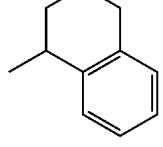 |
| 190 | 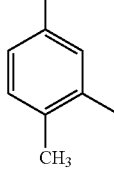 | —OC(=O)— | —SO₂— | 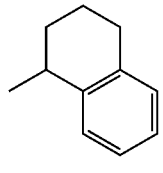 |
| 191 | 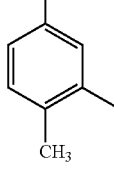 | —OC(=O)— | —C(=O)— | 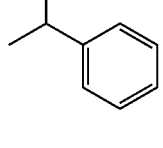 |

TABLE 1-continued
individual compounds of formula I according to the invention
| Compound No. | R¹ | A | Q | R⁹ |
|---|---|---|---|---|
| 192 | 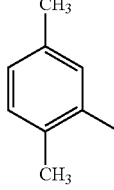 | —OC(=O)— | —C(=S)— | 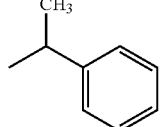 |
| 193 | 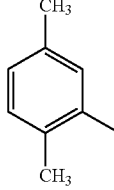 | —OC(=O)— | —C(=O)O— | 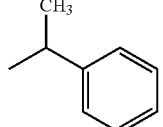 |
| 194 | 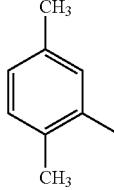 | —OC(=O)— | —C(=O)NH— | 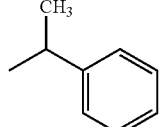 |
| 195 | 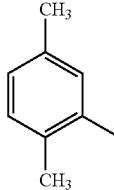 | —OC(=O)— | —SO₂— | 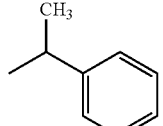 |
| 196 | 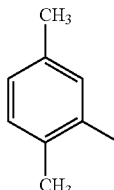 | —OC(=O)— | —C(=O)— | 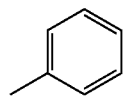 |
| 197 | 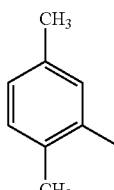 | —OC(=O)— | —C(=S)— | 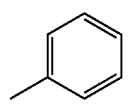 |
| 198 | 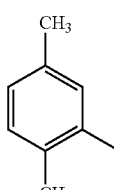 | —OC(=O)— | —C(=O)O— | 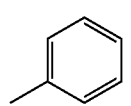 |

TABLE 1-continued
individual compounds of formula I according to the invention
| Compound No. | R¹ | A | Q | R⁹ |
|---|---|---|---|---|
| 199 | 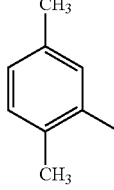 | —OC(=O)— | —C(=O)NH— | 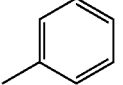 |
| 200 | 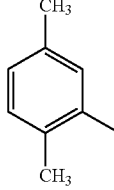 | —OC(=O)— | —SO₂— | 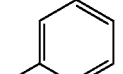 |
| 201 | 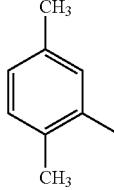 | —C(=O)— | —C(=O)— | 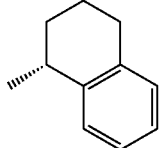 |
| 202 | 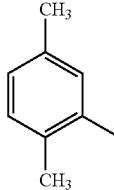 | —C(=O)— | —C(=S)— | 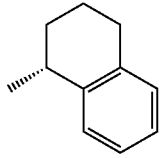 |
| 203 | 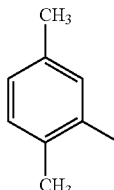 | —C(=O)— | —C(=O)O— | 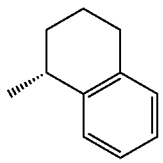 |
| 204 | 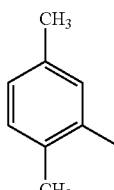 | —C(=O)— | —C(=O)NH— | 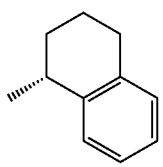 |
| 205 | 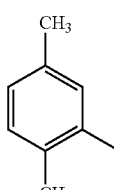 | —C(=O)— | —SO₂— | 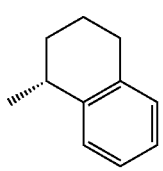 |

TABLE 1-continued
individual compounds of formula I according to the invention
| Compound No. | R¹ | A | Q | R⁹ |
|---|---|---|---|---|
| 206 | 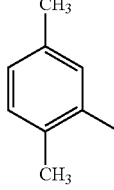 | —C(=O)— | —C(=O)— | 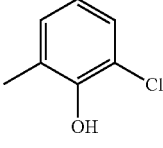 |
| 207 | 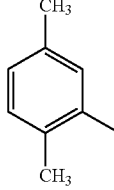 | —C(=O)— | —C(=S)— | 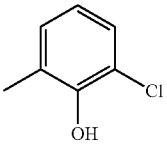 |
| 208 | 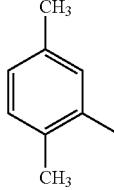 | —C(=O)— | —C(=O)O— | 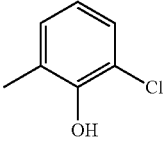 |
| 209 | 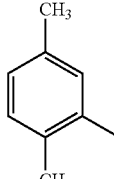 | —C(=O)— | —C(=O)NH— | 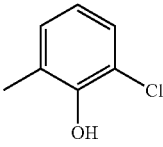 |
| 210 | 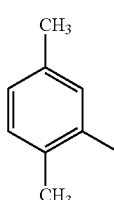 | —C(=O)— | —SO₂— | 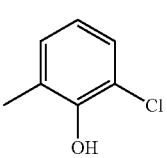 |
| 211 | 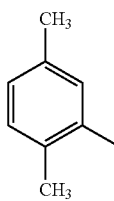 | —C(=O)— | —C(=O)— | 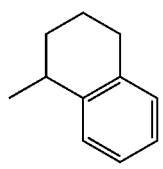 |
| 212 | 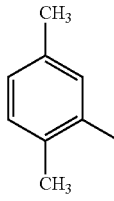 | —C(=O)— | —C(=S)— | 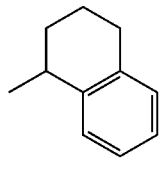 |

TABLE 1-continued
individual compounds of formula I according to the invention
| Compound No. | R¹ | A | Q | R⁹ |
|---|---|---|---|---|
| 213 | 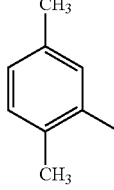 | —C(=O)— | —C(=O)O— | 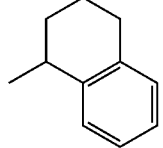 |
| 214 | 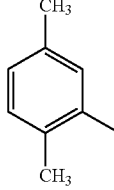 | —C(=O)— | —C(=O)NH— | 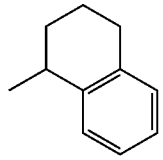 |
| 215 | 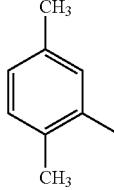 | —C(=O)— | —SO₂— | 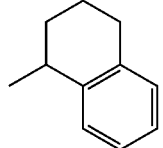 |
| 216 | 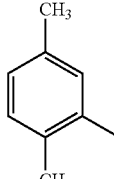 | —C(=O)— | —C(=O)— | 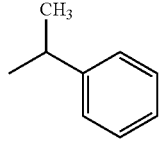 |
| 217 | 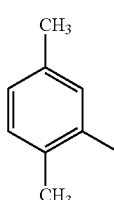 | —C(=O)— | —C(=S)— | 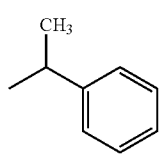 |
| 218 | 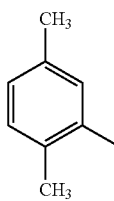 | —C(=O)— | —C(=O)O— | 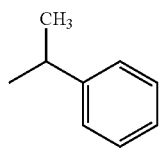 |
| 219 | 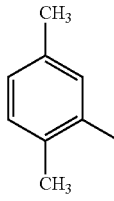 | —C(=O)— | —C(=O)NH— | 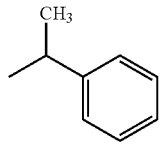 |

TABLE 1-continued
individual compounds of formula I according to the invention
| Compound No. | R¹ | A | Q | R⁹ |
|---|---|---|---|---|
| 220 | 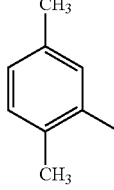 | —C(=O)— | —SO₂— | 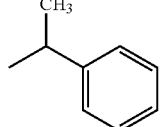 |
| 221 | 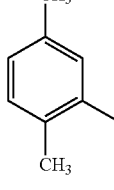 | —C(=O)— | —C(=O)— | 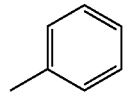 |
| 222 | 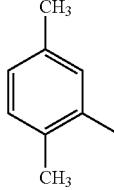 | —C(=O)— | —C(=S)— | 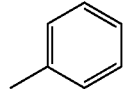 |
| 223 | 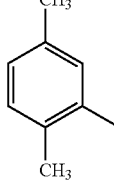 | —C(=O)— | —C(=O)O— | 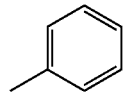 |
| 224 | 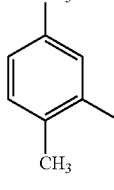 | —C(=O)— | —C(=O)NH— | 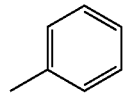 |
| 225 | 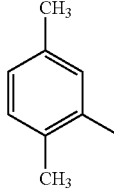 | —C(=O)— | —SO₂— | 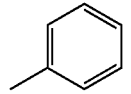 |
| 226 | 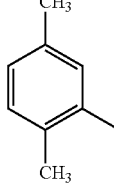 | —CH₂SO₂— | —C(=O)— | 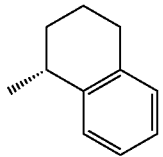 |

TABLE 1-continued
individual compounds of formula I according to the invention
| Compound No. | R¹ | A | Q | R⁹ |
|---|---|---|---|---|
| 227 | 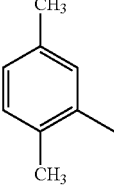 | —CH₂SO₂— | —C(=S)— | 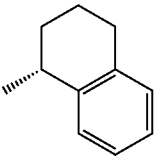 |
| 228 | 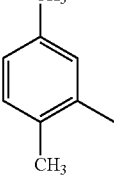 | —CH₂SO₂— | —C(=O)O— | 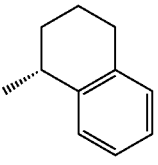 |
| 229 | 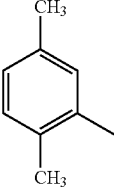 | —CH₂SO₂— | —C(=O)NH— | 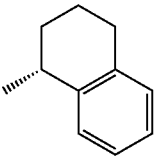 |
| 230 | 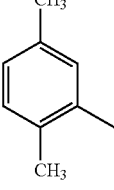 | —CH₂SO₂— | —SO₂— | 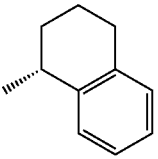 |
| 231 | 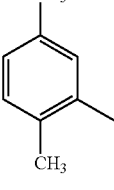 | —CH₂SO₂— | —C(=O)— | 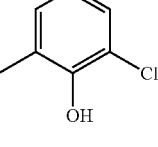 |
| 232 | 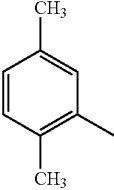 | —CH₂SO₂— | —C(=S)— | 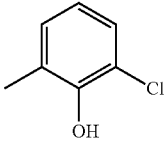 |
| 233 | 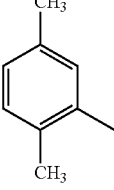 | —CH₂SO₂— | —C(=O)O— | 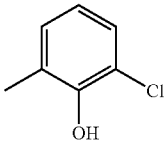 |

TABLE 1-continued
individual compounds of formula I according to the invention
| Compound No. | R¹ | A | Q | R⁹ |
|---|---|---|---|---|
| 234 | 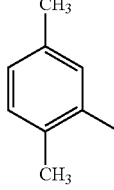 | —CH₂SO₂— | —C(=O)NH— | 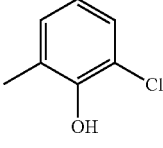 |
| 235 | 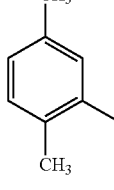 | —CH₂SO₂— | —SO₂— | 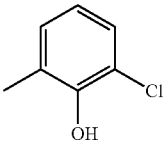 |
| 236 | 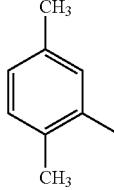 | —CH₂SO₂— | —C(=O)— | 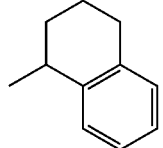 |
| 237 | 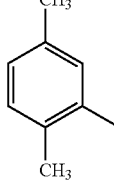 | —CH₂SO₂— | —C(=S)— | 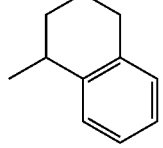 |
| 238 | 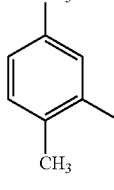 | —CH₂SO₂— | —C(=O)O— | 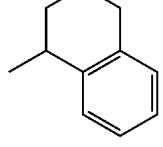 |
| 239 | 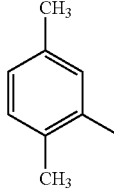 | —CH₂SO₂— | —C(=O)NH— | 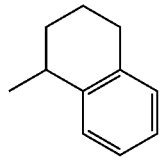 |
| 240 | 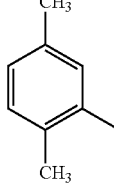 | —CH₂SO₂— | —SO₂— | 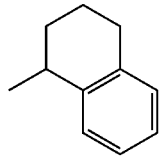 |

TABLE 1-continued
individual compounds of formula I according to the invention
| Compound No. | R¹ | A | Q | R⁹ |
|---|---|---|---|---|
| 241 | 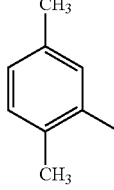 | —CH₂SO₂— | —C(=O)— | 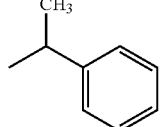 |
| 242 | 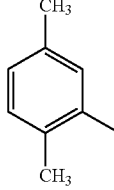 | —CH₂SO₂— | —C(=S)— | 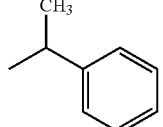 |
| 243 | 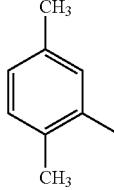 | —CH₂SO₂— | —C(=O)O— | 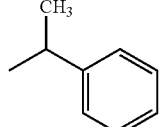 |
| 244 | 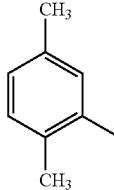 | —CH₂SO₂— | —C(=O)NH— | 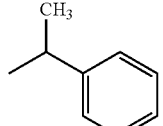 |
| 245 | 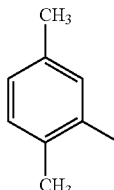 | —CH₂SO₂— | —SO₂— | 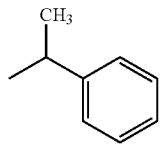 |
| 246 | 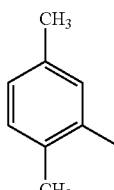 | —CH₂SO₂— | —C(=O)— | 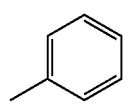 |
| 247 | 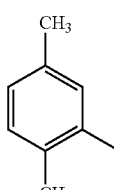 | —CH₂SO₂— | —C(=S)— | 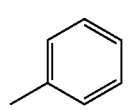 |

TABLE 1-continued
individual compounds of formula I according to the invention
| Compound No. | R¹ | A | Q | R⁹ |
|---|---|---|---|---|
| 248 | 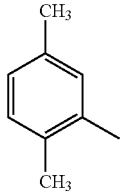 | —CH₂SO₂— | —C(=O)O— | 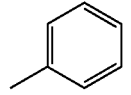 |
| 249 | 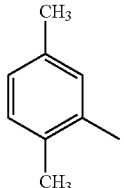 | —CH₂SO₂— | —C(=O)NH— | 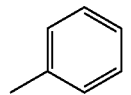 |
| 250 | 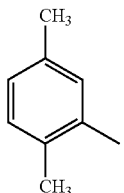 | —CH₂SO₂— | —SO₂— | 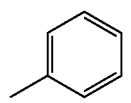 |
| 251 | 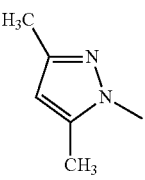 | —CH₂C(=O)— | —C(=O)— | 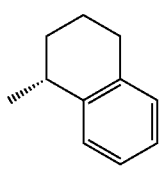 |
| 252 | 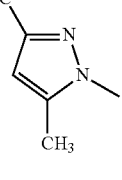 | —CH₂C(=O)— | —C(=S)— | 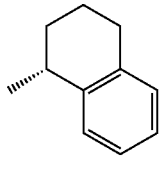 |
| 253 | 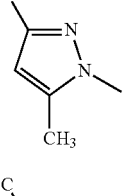 | —CH₂C(=O)— | —C(=O)O— | 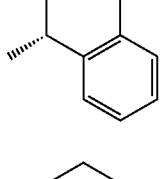 |
| 254 | 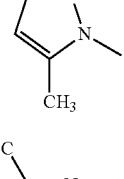 | —CH₂C(=O)— | —C(=O)NH— | 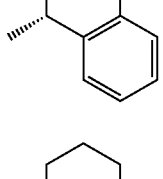 |
| 255 | 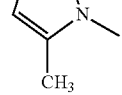 | —CH₂C(=O)— | —SO₂— | 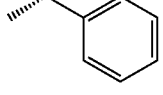 |

TABLE 1-continued
individual compounds of formula I according to the invention
| Compound No. | R¹ | A | Q | R⁹ |
|---|---|---|---|---|
| 256 | 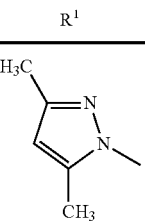 | —CH₂C(=O)— | —C(=O)— | 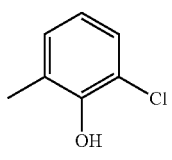 |
| 257 | 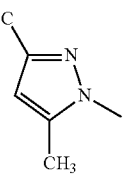 | —CH₂C(=O)— | —C(=S)— | 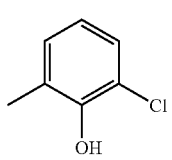 |
| 258 | 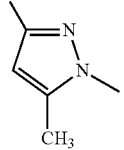 | —CH₂C(=O)— | —C(=O)O— | 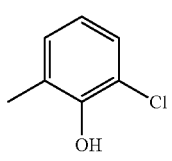 |
| 259 | 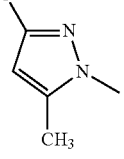 | —CH₂C(=O)— | —C(=O)NH— | 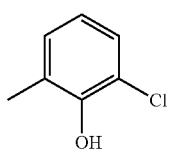 |
| 260 | 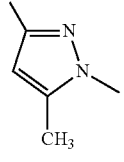 | —CH₂C(=O)— | —SO₂— | 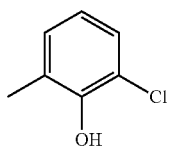 |
| 261 | 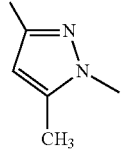 | —CH₂C(=O)— | —C(=O)— | 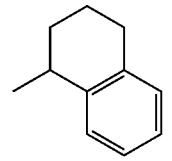 |
| 262 | 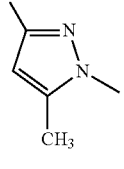 | —CH₂C(=O)— | —C(=S)— | 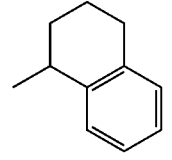 |
| 263 | 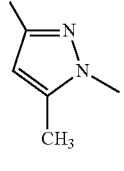 | —CH₂C(=O)— | —C(=O)O— | 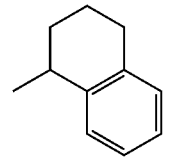 |

TABLE 1-continued
individual compounds of formula I according to the invention
| Compound No. | R¹ | A | Q | R⁹ |
|---|---|---|---|---|
| 264 | 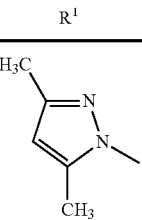 | —CH₂C(=O)— | —C(=O)NH— | 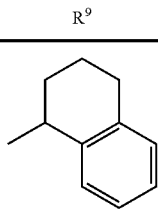 |
| 265 | 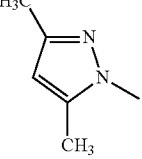 | —CH₂C(=O)— | —SO₂— | 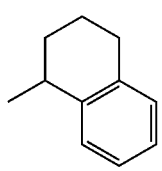 |
| 266 | 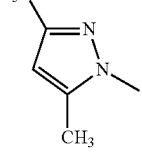 | —CH₂C(=O)— | —C(=O)— | 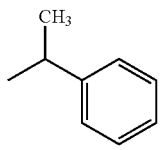 |
| 267 | 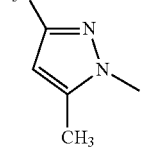 | —CH₂C(=O)— | —C(=S)— | 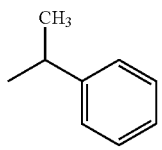 |
| 268 | 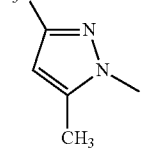 | —CH₂C(=O)— | —C(=O)O— | 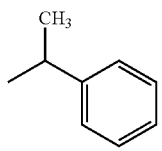 |
| 269 | 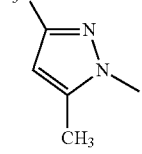 | —CH₂C(=O)— | —C(=O)NH— | 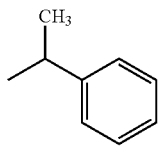 |
| 270 | 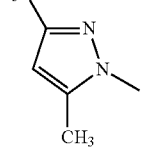 | —CH₂C(=O)— | —SO₂— | 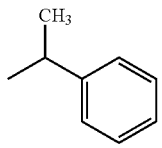 |
| 271 | 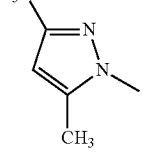 | —CH₂C(=O)— | —C(=O)— | 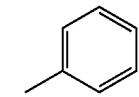 |

TABLE 1-continued
individual compounds of formula I according to the invention
| Compound No. | R¹ | A | Q | R⁹ |
|---|---|---|---|---|
| 272 | 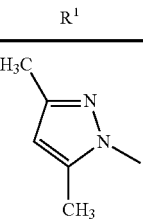 | —CH₂C(=O)— | —C(=S)— | 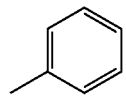 |
| 273 | 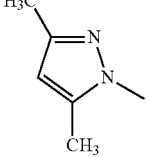 | —CH₂C(=O)— | —C(=O)O— | 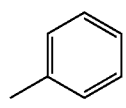 |
| 274 | 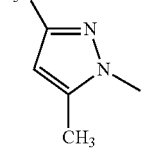 | —CH₂C(=O)— | —C(=O)NH— | 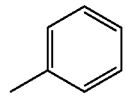 |
| 275 | 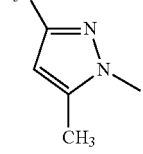 | —CH₂C(=O)— | —SO₂— | 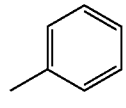 |
| 276 | 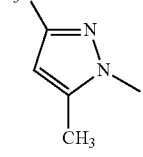 | —CH₂C(=S)— | —C(=O)— | 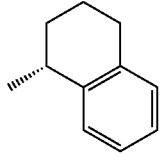 |
| 277 | 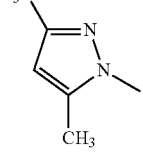 | —CH₂C(=S)— | —C(=S)— | 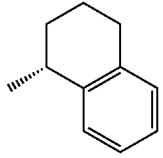 |
| 278 | 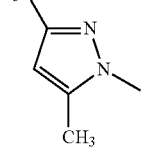 | —CH₂C(=S)— | —C(=O)O— | 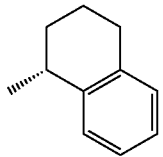 |
| 279 | 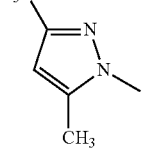 | —CH₂C(=S)— | —C(=O)NH— | 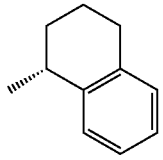 |

TABLE 1-continued
individual compounds of formula I according to the invention
| Compound No. | R¹ | A | Q | R⁹ |
|---|---|---|---|---|
| 280 | 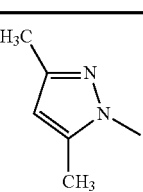 | —CH₂C(=S)— | —SO₂— | 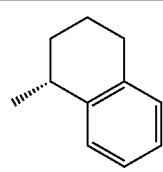 |
| 281 | 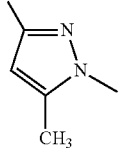 | —CH₂C(=S)— | —C(=O)— | 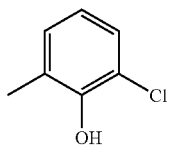 |
| 282 | 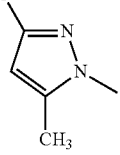 | —CH₂C(=S)— | —C(=S)— | 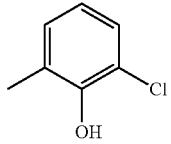 |
| 283 | 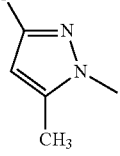 | —CH₂C(=S)— | —C(=O)O— | 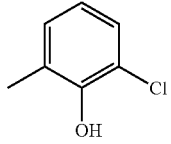 |
| 284 | 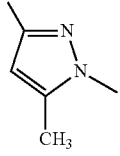 | —CH₂C(=S)— | —C(=O)NH— | 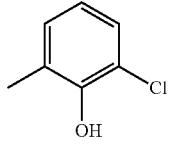 |
| 285 | 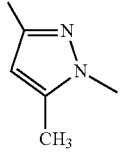 | —CH₂C(=S)— | —SO₂— | 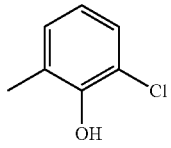 |
| 286 | 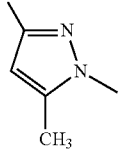 | —CH₂C(=S)— | —C(=O)— | 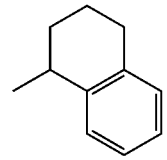 |
| 287 | 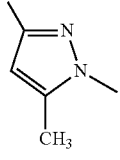 | —CH₂C(=S)— | —C(=S)— | 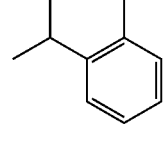 |

TABLE 1-continued
individual compounds of formula I according to the invention
| Compound No. | R¹ | A | Q | R⁹ |
|---|---|---|---|---|
| 288 | 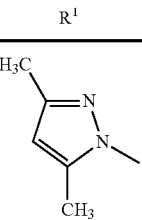 | —CH₂C(=S)— | —C(=O)O— | 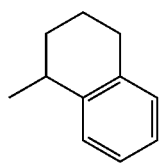 |
| 289 | 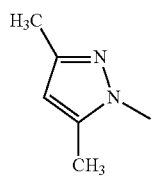 | —CH₂C(=S)— | —C(=O)NH— | 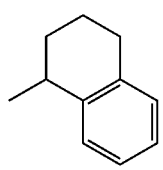 |
| 290 | 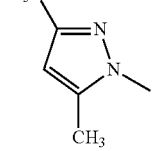 | —CH₂C(=S)— | —SO₂— | 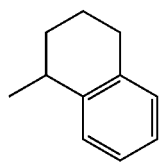 |
| 291 | 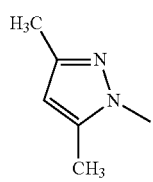 | —CH₂C(=S)— | —C(=O)— | 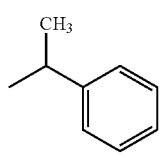 |
| 292 | 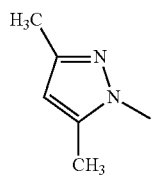 | —CH₂C(=S)— | —C(=S)— | 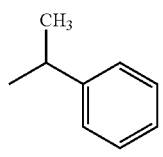 |
| 293 | 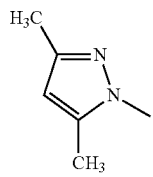 | —CH₂C(=S)— | —C(=O)O— | 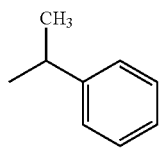 |
| 294 | 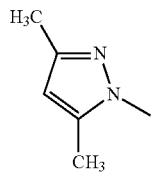 | —CH₂C(=S)— | —C(=O)NH— | 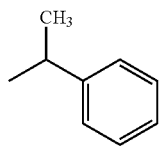 |
| 295 | 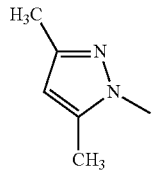 | —CH₂C(=S)— | —SO₂— | 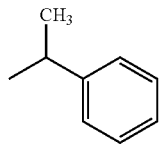 |

TABLE 1-continued
individual compounds of formula I according to the invention
| Compound No. | R¹ | A | Q | R⁹ |
|---|---|---|---|---|
| 296 | 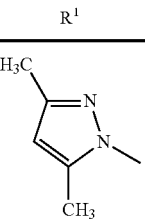 | —CH₂C(=S)— | —C(=O)— | 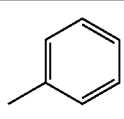 |
| 297 | 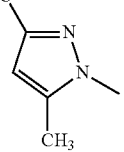 | —CH₂C(=S)— | —C(=S)— | 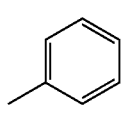 |
| 298 | 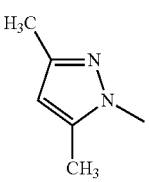 | —CH₂C(=S)— | —C(=O)O— | 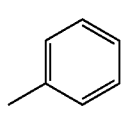 |
| 299 | 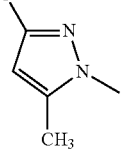 | —CH₂C(=S)— | —C(=O)NH— | 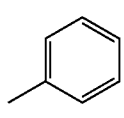 |
| 300 | 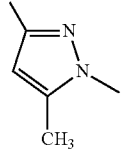 | —CH₂C(=S)— | —SO₂— | 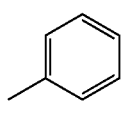 |
| 301 | 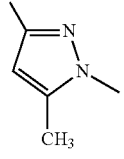 | —OC(=O)— | —C(=O)— | 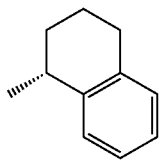 |
| 302 | 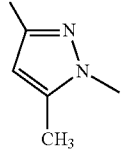 | —OC(=O)— | —C(=S)— | 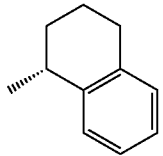 |
| 303 | 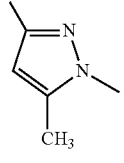 | —OC(=O)— | —C(=O)O— | 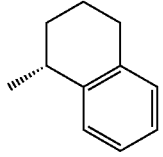 |

TABLE 1-continued individual compounds of formula I according to the invention

| Compound No. | R¹ | A | Q | R⁹ |
|---|---|---|---|---|
| 304 | 1,3-dimethyl-5-methyl-pyrazole | —OC(=O)— | —C(=O)NH— | (S)-1,2,3,4-tetrahydronaphthalen-1-yl |
| 305 | 1,3-dimethyl-5-methyl-pyrazole | —OC(=O)— | —SO₂— | (S)-1,2,3,4-tetrahydronaphthalen-1-yl |
| 306 | 1,3-dimethyl-5-methyl-pyrazole | —OC(=O)— | —C(=O)— | 2-chloro-6-methylphenol |
| 307 | 1,3-dimethyl-5-methyl-pyrazole | —OC(=O)— | —C(=S)— | 2-chloro-6-methylphenol |
| 308 | 1,3-dimethyl-5-methyl-pyrazole | —OC(=O)— | —C(=O)O— | 2-chloro-6-methylphenol |
| 309 | 1,3-dimethyl-5-methyl-pyrazole | —OC(=O)— | —C(=O)NH— | 2-chloro-6-methylphenol |
| 310 | 1,3-dimethyl-5-methyl-pyrazole | —OC(=O)— | —SO₂— | 2-chloro-6-methylphenol |
| 311 | 1,3-dimethyl-5-methyl-pyrazole | —OC(=O)— | —C(=O)— | 1-methyl-1,2,3,4-tetrahydronaphthalene |

TABLE 1-continued
individual compounds of formula I according to the invention
| Compound No. | R¹ | A | Q | R⁹ |
|---|---|---|---|---|
| 312 | 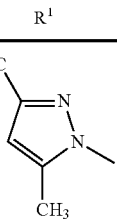 | —OC(=O)— | —C(=S)— | 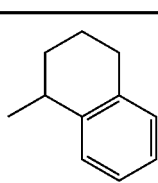 |
| 313 | 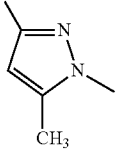 | —OC(=O)— | —C(=O)O— | 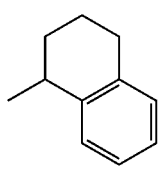 |
| 314 | 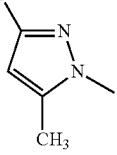 | —OC(=O)— | —C(=O)NH— | 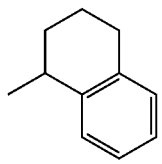 |
| 315 | 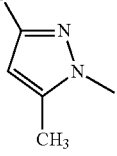 | —OC(=O)— | —SO₂— | 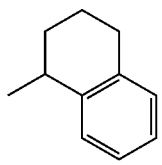 |
| 316 | 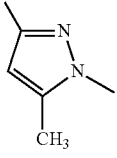 | —OC(=O)— | —C(=O)— | 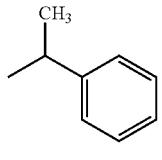 |
| 317 | 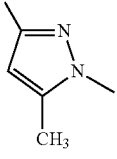 | —OC(=O)— | —C(=S)— | 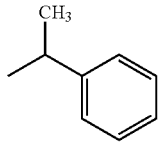 |
| 318 | 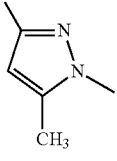 | —OC(=O)— | —C(=O)O— | 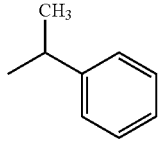 |
| 319 | 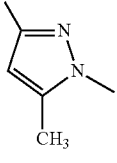 | —OC(=O)— | —C(=O)NH— | 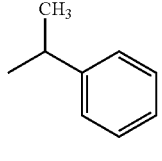 |

TABLE 1-continued
individual compounds of formula I according to the invention
| Compound No. | R¹ | A | Q | R⁹ |
|---|---|---|---|---|
| 320 | 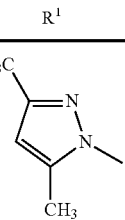 | —OC(=O)— | —SO₂— | 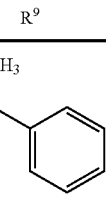 |
| 321 | 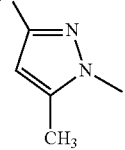 | —OC(=O)— | —C(=O)— | 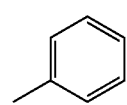 |
| 322 | 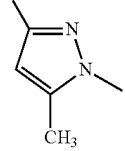 | —OC(=O)— | —C(=S)— | 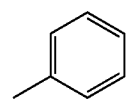 |
| 323 | 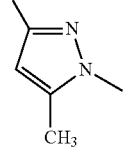 | —OC(=O)— | —C(=O)O— | 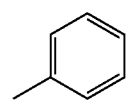 |
| 324 | 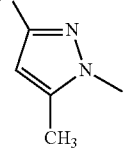 | —OC(=O)— | —C(=O)NH— | 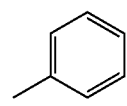 |
| 325 | 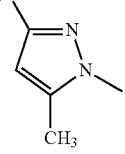 | —OC(=O)— | —SO₂— | 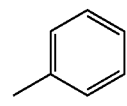 |
| 326 | 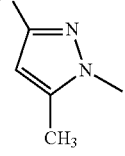 | —C(=O)— | —C(=O)— | 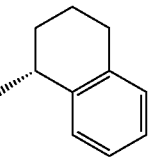 |
| 327 | 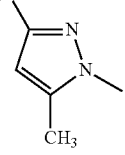 | —C(=O)— | —C(=S)— | 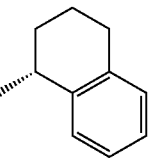 |

TABLE 1-continued
individual compounds of formula I according to the invention
| Compound No. | R[1] | A | Q | R[9] |
|---|---|---|---|---|
| 328 | 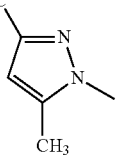 | —C(=O)— | —C(=O)O— | 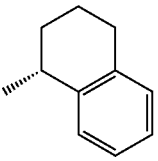 |
| 329 | 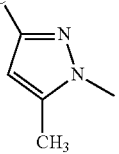 | —C(=O)— | —C(=O)NH— | 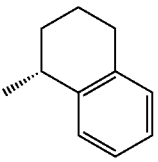 |
| 330 | 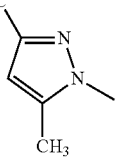 | —C(=O)— | —SO$_2$— | 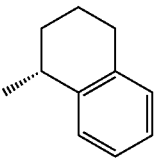 |
| 331 | 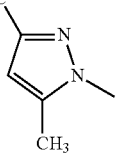 | —C(=O)— | —C(=O)— | 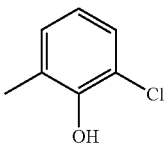 |
| 332 | 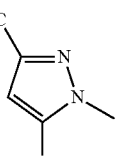 | —C(=O)— | —C(=S)— | 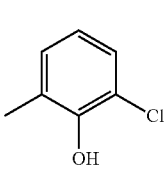 |
| 333 | 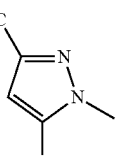 | —C(=O)— | —C(=O)O— | 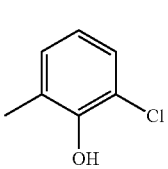 |
| 334 | 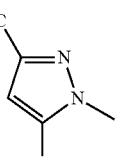 | —C(=O)— | —C(=O)NH— | 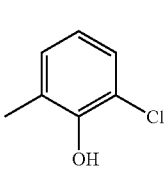 |
| 335 | 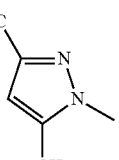 | —C(=O)— | —SO$_2$— | 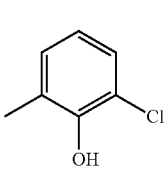 |

TABLE 1-continued individual compounds of formula I according to the invention

| Compound No. | R¹ | A | Q | R⁹ |
|---|---|---|---|---|
| 336 | 3,5-dimethylpyrazol-1-yl | —C(=O)— | —C(=O)— | 1-(1,2,3,4-tetrahydronaphthyl) |
| 337 | 3,5-dimethylpyrazol-1-yl | —C(=O)— | —C(=S)— | 1-(1,2,3,4-tetrahydronaphthyl) |
| 338 | 3,5-dimethylpyrazol-1-yl | —C(=O)— | —C(=O)O— | 1-(1,2,3,4-tetrahydronaphthyl) |
| 339 | 3,5-dimethylpyrazol-1-yl | —C(=O)— | —C(=O)NH— | 1-(1,2,3,4-tetrahydronaphthyl) |
| 340 | 3,5-dimethylpyrazol-1-yl | —C(=O)— | —SO₂— | 1-(1,2,3,4-tetrahydronaphthyl) |
| 341 | 3,5-dimethylpyrazol-1-yl | —C(=O)— | —C(=O)— | 1-phenylethyl |
| 342 | 3,5-dimethylpyrazol-1-yl | —C(=O)— | —C(=S)— | 1-phenylethyl |
| 343 | 3,5-dimethylpyrazol-1-yl | —C(=O)— | —C(=O)O— | 1-phenylethyl |

TABLE 1-continued
individual compounds of formula I according to the invention
| Compound No. | R¹ | A | Q | R⁹ |
|---|---|---|---|---|
| 344 | 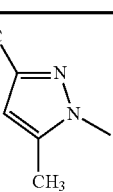 | —C(=O)— | —C(=O)NH— | 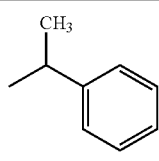 |
| 345 | 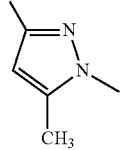 | —C(=O)— | —SO₂— | 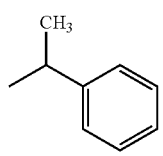 |
| 346 | 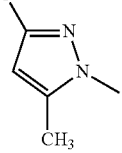 | —C(=O)— | —C(=O)— | 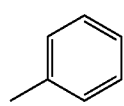 |
| 347 | 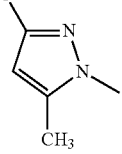 | —C(=O)— | —C(=S)— | 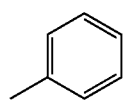 |
| 348 | 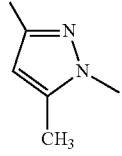 | —C(=O)— | —C(=O)O— | 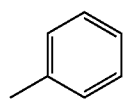 |
| 349 | 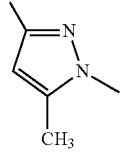 | —C(=O)— | —C(=O)NH— | 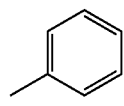 |
| 350 | 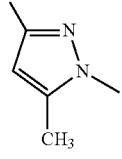 | —C(=O)— | —SO₂— | 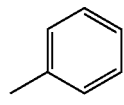 |
| 351 | 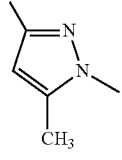 | —CH₂SO₂— | —C(=O)— | 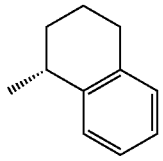 |

TABLE 1-continued
individual compounds of formula I according to the invention
| Compound No. | R¹ | A | Q | R⁹ |
|---|---|---|---|---|
| 352 | 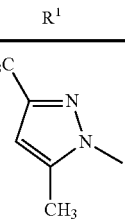 | —CH₂SO₂— | —C(=S)— | 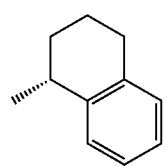 |
| 353 | 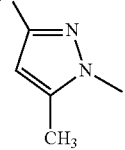 | —CH₂SO₂— | —C(=O)O— | 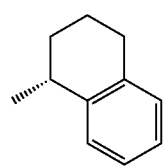 |
| 354 | 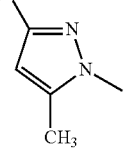 | —CH₂SO₂— | —C(=O)NH— | 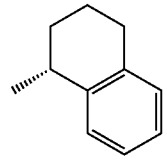 |
| 355 | 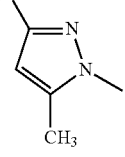 | —CH₂SO₂— | —SO₂— | 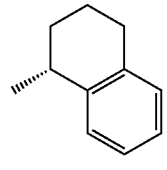 |
| 356 | 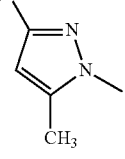 | —CH₂SO₂— | —C(=O)— | 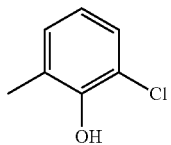 |
| 357 | 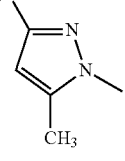 | —CH₂SO₂— | —C(=S)— | 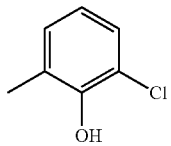 |
| 358 | 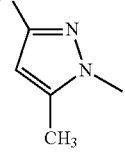 | —CH₂SO₂— | —C(=O)O— | 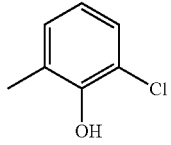 |
| 359 | 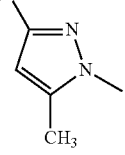 | —CH₂SO₂— | —C(=O)NH— | 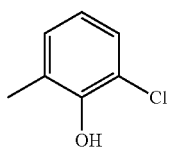 |

TABLE 1-continued
individual compounds of formula I according to the invention
| Compound No. | R¹ | A | Q | R⁹ |
|---|---|---|---|---|
| 360 | 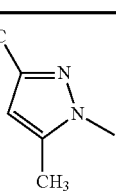 | —CH₂SO₂— | —SO₂— | 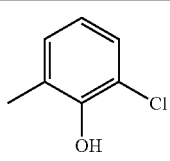 |
| 361 | 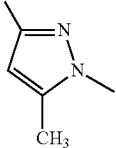 | —CH₂SO₂— | —C(=O)— | 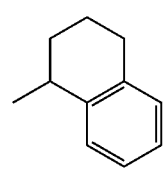 |
| 362 | 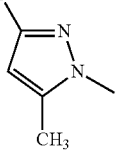 | —CH₂SO₂— | —C(=S)— | 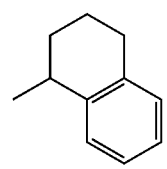 |
| 363 | 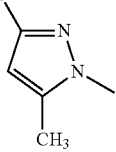 | —CH₂SO₂— | —C(=O)O— | 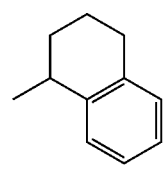 |
| 364 | 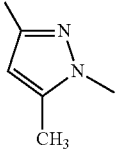 | —CH₂SO₂— | —C(=O)NH— | 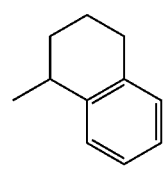 |
| 365 | 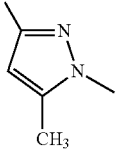 | —CH₂SO₂— | —SO₂— | 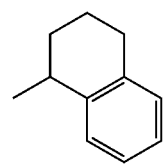 |
| 366 | 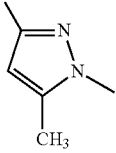 | —CH₂SO₂— | —C(=O)— | 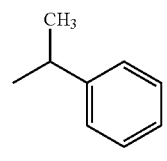 |
| 367 | 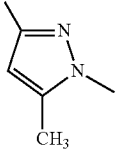 | —CH₂SO₂— | —C(=S)— | 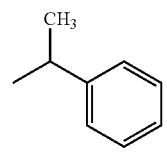 |

TABLE 1-continued individual compounds of formula I according to the invention

| Compound No. | R¹ | A | Q | R⁹ |
|---|---|---|---|---|
| 368 | 1,3,5-trimethylpyrazole | —CH$_2$SO$_2$— | —C(=O)O— | 1-phenylethyl |
| 369 | 1,3,5-trimethylpyrazole | —CH$_2$SO$_2$— | —C(=O)NH— | 1-phenylethyl |
| 370 | 1,3,5-trimethylpyrazole | —CH$_2$SO$_2$— | —SO$_2$— | 1-phenylethyl |
| 371 | 1,3,5-trimethylpyrazole | —CH$_2$SO$_2$— | —C(=O)— | 4-methylphenyl |
| 372 | 1,3,5-trimethylpyrazole | —CH$_2$SO$_2$— | —C(=S)— | 4-methylphenyl |
| 373 | 1,3,5-trimethylpyrazole | —CH$_2$SO$_2$— | —C(=O)O— | 4-methylphenyl |
| 374 | 1,3,5-trimethylpyrazole | —CH$_2$SO$_2$— | —C(=O)NH— | 4-methylphenyl |
| 375 | 1,3,5-trimethylpyrazole | —CH$_2$SO$_2$— | —SO$_2$— | 4-methylphenyl |

TABLE 1-continued
individual compounds of formula I according to the invention
| Compound No. | R¹ | A | Q | R⁹ |
|---|---|---|---|---|
| 376 | 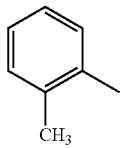 | —CH₂C(=O)— | —C(=O)— | 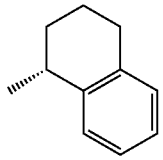 |
| 377 | 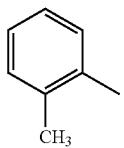 | —CH₂C(=O)— | —C(=S)— | 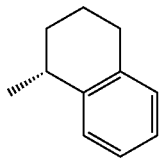 |
| 378 | 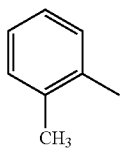 | —CH₂C(=O)— | —C(=O)O— | 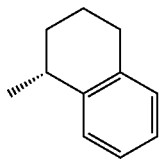 |
| 379 | 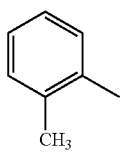 | —CH₂C(=O)— | —C(=O)NH— | 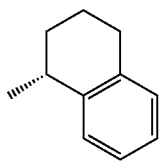 |
| 380 | 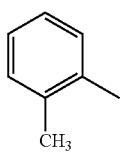 | —CH₂C(=O)— | —SO₂— | 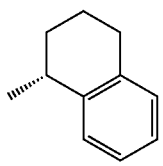 |
| 381 | 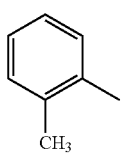 | —CH₂C(=O)— | —C(=O)— | 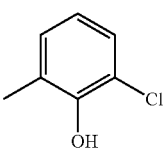 |
| 382 | 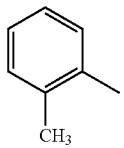 | —CH₂C(=O)— | —C(=S)— | 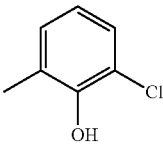 |
| 383 | 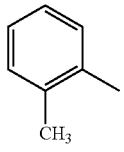 | —CH₂C(=O)— | —C(=O)O— | 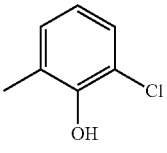 |
| 384 | 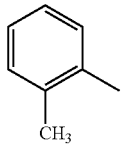 | —CH₂C(=O)— | —C(=O)NH— | 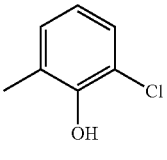 |

TABLE 1-continued individual compounds of formula I according to the invention

| Compound No. | R¹ | A | Q | R⁹ |
|---|---|---|---|---|
| 385 | 2-methylphenyl | —CH₂C(=O)— | —SO₂— | 2-chloro-6-methylphenol (2-methyl-6-chloro-phenol with OH) |
| 386 | 2-methylphenyl | —CH₂C(=O)— | —C(=O)— | 1,2,3,4-tetrahydronaphthalen-1-yl |
| 387 | 2-methylphenyl | —CH₂C(=O)— | —C(=S)— | 1,2,3,4-tetrahydronaphthalen-1-yl |
| 388 | 2-methylphenyl | —CH₂C(=O)— | —C(=O)O— | 1,2,3,4-tetrahydronaphthalen-1-yl |
| 389 | 2-methylphenyl | —CH₂C(=O)— | —C(=O)NH— | 1,2,3,4-tetrahydronaphthalen-1-yl |
| 390 | 2-methylphenyl | —CH₂C(=O)— | —SO₂— | 1,2,3,4-tetrahydronaphthalen-1-yl |
| 391 | 2-methylphenyl | —CH₂C(=O)— | —C(=O)— | 1-phenylethyl |
| 392 | 2-methylphenyl | —CH₂C(=O)— | —C(=S)— | 1-phenylethyl |
| 393 | 2-methylphenyl | —CH₂C(=O)— | —C(=O)O— | 1-phenylethyl |

TABLE 1-continued individual compounds of formula I according to the invention

| Compound No. | R¹ | A | Q | R⁹ |
|---|---|---|---|---|
| 394 | 2-methylphenyl | —CH₂C(=O)— | —C(=O)NH— | 1-phenylethyl |
| 395 | 2-methylphenyl | —CH₂C(=O)— | —SO₂— | 1-phenylethyl |
| 396 | 2-methylphenyl | —CH₂C(=O)— | —C(=O)— | 1-phenylethyl (methyl-phenyl) |
| 397 | 2-methylphenyl | —CH₂C(=O)— | —C(=S)— | 1-phenylethyl (methyl-phenyl) |
| 398 | 2-methylphenyl | —CH₂C(=O)— | —C(=O)O— | 1-phenylethyl (methyl-phenyl) |
| 399 | 2-methylphenyl | —CH₂C(=O)— | —C(=O)NH— | 1-phenylethyl (methyl-phenyl) |
| 400 | 2-methylphenyl | —CH₂C(=O)— | —SO₂— | 1-phenylethyl (methyl-phenyl) |
| 401 | 2-methylphenyl | —CH₂C(=S)— | —C(=O)— | (S)-1,2,3,4-tetrahydronaphthalen-1-yl |
| 402 | 2-methylphenyl | —CH₂C(=S)— | —C(=S)— | (S)-1,2,3,4-tetrahydronaphthalen-1-yl |

TABLE 1-continued individual compounds of formula I according to the invention

| Compound No. | R¹ | A | Q | R⁹ |
|---|---|---|---|---|
| 403 | 2-methylphenyl | —CH₂C(=S)— | —C(=O)O— | (S)-1,2,3,4-tetrahydronaphthalen-1-yl |
| 404 | 2-methylphenyl | —CH₂C(=S)— | —C(=O)NH— | (S)-1,2,3,4-tetrahydronaphthalen-1-yl |
| 405 | 2-methylphenyl | —CH₂C(=S)— | —SO₂— | (S)-1,2,3,4-tetrahydronaphthalen-1-yl |
| 406 | 2-methylphenyl | —CH₂C(=S)— | —C(=O)— | 2-chloro-6-methylphenol |
| 407 | 2-methylphenyl | —CH₂C(=S)— | —C(=S)— | 2-chloro-6-methylphenol |
| 408 | 2-methylphenyl | —CH₂C(=S)— | —C(=O)O— | 2-chloro-6-methylphenol |
| 409 | 2-methylphenyl | —CH₂C(=S)— | —C(=O)NH— | 2-chloro-6-methylphenol |
| 410 | 2-methylphenyl | —CH₂C(=S)— | —SO₂— | 2-chloro-6-methylphenol |
| 411 | 2-methylphenyl | —CH₂C(=S)— | —C(=O)— | 1,2,3,4-tetrahydronaphthalen-1-yl |

TABLE 1-continued individual compounds of formula I according to the invention

| Compound No. | R¹ | A | Q | R⁹ |
|---|---|---|---|---|
| 412 | 2-methylphenyl | —CH₂C(=S)— | —C(=S)— | 1,2,3,4-tetrahydronaphthalen-1-yl |
| 413 | 2-methylphenyl | —CH₂C(=S)— | —C(=O)O— | 1,2,3,4-tetrahydronaphthalen-1-yl |
| 414 | 2-methylphenyl | —CH₂C(=S)— | —C(=O)NH— | 1,2,3,4-tetrahydronaphthalen-1-yl |
| 415 | 2-methylphenyl | —CH₂C(=S)— | —SO₂— | 1,2,3,4-tetrahydronaphthalen-1-yl |
| 416 | 2-methylphenyl | —CH₂C(=S)— | —C(=O)— | 1-phenylethyl |
| 417 | 2-methylphenyl | —CH₂C(=S)— | —C(=S)— | 1-phenylethyl |
| 418 | 2-methylphenyl | —CH₂C(=S)— | —C(=O)O— | 1-phenylethyl |
| 419 | 2-methylphenyl | —CH₂C(=S)— | —C(=O)NH— | 1-phenylethyl |
| 420 | 2-methylphenyl | —CH₂C(=S)— | —SO₂— | 1-phenylethyl |

TABLE 1-continued individual compounds of formula I according to the invention

| Compound No. | R¹ | A | Q | R⁹ |
|---|---|---|---|---|
| 421 | 2-methylphenyl | —CH₂C(=S)— | —C(=O)— | phenyl |
| 422 | 2-methylphenyl | —CH₂C(=S)— | —C(=S)— | phenyl |
| 423 | 2-methylphenyl | —CH₂C(=S)— | —C(=O)O— | phenyl |
| 424 | 2-methylphenyl | —CH₂C(=S)— | —C(=O)NH— | phenyl |
| 425 | 2-methylphenyl | —CH₂C(=S)— | —SO₂— | phenyl |
| 426 | 2-methylphenyl | —OC(=O)— | —C(=O)— | (S)-1,2,3,4-tetrahydronaphthalen-1-yl |
| 427 | 2-methylphenyl | —OC(=O)— | —C(=S)— | (S)-1,2,3,4-tetrahydronaphthalen-1-yl |
| 428 | 2-methylphenyl | —OC(=O)— | —C(=O)O— | (S)-1,2,3,4-tetrahydronaphthalen-1-yl |
| 429 | 2-methylphenyl | —OC(=O)— | —C(=O)NH— | (S)-1,2,3,4-tetrahydronaphthalen-1-yl |

TABLE 1-continued individual compounds of formula I according to the invention

| Compound No. | R¹ | A | Q | R⁹ |
|---|---|---|---|---|
| 430 | 2-methylphenyl | —OC(=O)— | —SO$_2$— | (S)-1-methyl-1,2,3,4-tetrahydronaphthalenyl |
| 431 | 2-methylphenyl | —OC(=O)— | —C(=O)— | 2-chloro-6-methylphenol |
| 432 | 2-methylphenyl | —OC(=O)— | —C(=S)— | 2-chloro-6-methylphenol |
| 433 | 2-methylphenyl | —OC(=O)— | —C(=O)O— | 2-chloro-6-methylphenol |
| 434 | 2-methylphenyl | —OC(=O)— | —C(=O)NH— | 2-chloro-6-methylphenol |
| 435 | 2-methylphenyl | —OC(=O)— | —SO$_2$— | 2-chloro-6-methylphenol |
| 436 | 2-methylphenyl | —OC(=O)— | —C(=O)— | 1-methyl-1,2,3,4-tetrahydronaphthalenyl |
| 437 | 2-methylphenyl | —OC(=O)— | —C(=S)— | 1-methyl-1,2,3,4-tetrahydronaphthalenyl |
| 438 | 2-methylphenyl | —OC(=O)— | —C(=O)O— | 1-methyl-1,2,3,4-tetrahydronaphthalenyl |

TABLE 1-continued individual compounds of formula I according to the invention

| Compound No. | R¹ | A | Q | R⁹ |
|---|---|---|---|---|
| 439 | 2-methylphenyl | —OC(=O)— | —C(=O)NH— | 1,2,3,4-tetrahydronaphthalen-1-yl |
| 440 | 2-methylphenyl | —OC(=O)— | —SO₂— | 1,2,3,4-tetrahydronaphthalen-1-yl |
| 441 | 2-methylphenyl | —OC(=O)— | —C(=O)— | 1-phenylethyl |
| 442 | 2-methylphenyl | —OC(=O)— | —C(=S)— | 1-phenylethyl |
| 443 | 2-methylphenyl | —OC(=O)— | —C(=O)O— | 1-phenylethyl |
| 444 | 2-methylphenyl | —OC(=O)— | —C(=O)NH— | 1-phenylethyl |
| 445 | 2-methylphenyl | —OC(=O)— | —SO₂— | 1-phenylethyl |
| 446 | 2-methylphenyl | —OC(=O)— | —C(=O)— | 4-methylphenyl |
| 447 | 2-methylphenyl | —OC(=O)— | —C(=S)— | 4-methylphenyl |

TABLE 1-continued individual compounds of formula I according to the invention

| Compound No. | R¹ | A | Q | R⁹ |
|---|---|---|---|---|
| 448 | 2-CH₃-phenyl | —OC(=O)— | —C(=O)O— | phenyl |
| 449 | 2-CH₃-phenyl | —OC(=O)— | —C(=O)NH— | phenyl |
| 450 | 2-CH₃-phenyl | —OC(=O)— | —SO₂— | phenyl |
| 451 | 2-CH₃-phenyl | —C(=O)— | —C(=O)— | (S)-1,2,3,4-tetrahydronaphthyl |
| 452 | 2-CH₃-phenyl | —C(=O)— | —C(=S)— | (S)-1,2,3,4-tetrahydronaphthyl |
| 453 | 2-CH₃-phenyl | —C(=O)— | —C(=O)O— | (S)-1,2,3,4-tetrahydronaphthyl |
| 454 | 2-CH₃-phenyl | —C(=O)— | —C(=O)NH— | (S)-1,2,3,4-tetrahydronaphthyl |
| 455 | 2-CH₃-phenyl | —C(=O)— | —SO₂— | (S)-1,2,3,4-tetrahydronaphthyl |
| 456 | 2-CH₃-phenyl | —C(=O)— | —C(=O)— | 2-chloro-6-methyl-phenol |

TABLE 1-continued individual compounds of formula I according to the invention

| Compound No. | R¹ | A | Q | R⁹ |
|---|---|---|---|---|
| 457 | 2-methylphenyl | —C(=O)— | —C(=S)— | 2-chloro-6-methylphenol |
| 458 | 2-methylphenyl | —C(=O)— | —C(=O)O— | 2-chloro-6-methylphenol |
| 459 | 2-methylphenyl | —C(=O)— | —C(=O)NH— | 2-chloro-6-methylphenol |
| 460 | 2-methylphenyl | —C(=O)— | —SO₂— | 2-chloro-6-methylphenol |
| 461 | 2-methylphenyl | —C(=O)— | —C(=O)— | 1,2,3,4-tetrahydronaphthalen-1-yl |
| 462 | 2-methylphenyl | —C(=O)— | —C(=S)— | 1,2,3,4-tetrahydronaphthalen-1-yl |
| 463 | 2-methylphenyl | —C(=O)— | —C(=O)O— | 1,2,3,4-tetrahydronaphthalen-1-yl |
| 464 | 2-methylphenyl | —C(=O)— | —C(=O)NH— | 1,2,3,4-tetrahydronaphthalen-1-yl |
| 465 | 2-methylphenyl | —C(=O)— | —SO₂— | 1,2,3,4-tetrahydronaphthalen-1-yl |

TABLE 1-continued individual compounds of formula I according to the invention

| Compound No. | R¹ | A | Q | R⁹ |
|---|---|---|---|---|
| 466 | 2-methylphenyl | —C(=O)— | —C(=O)— | α-methylbenzyl (isopropylphenyl) |
| 467 | 2-methylphenyl | —C(=O)— | —C(=S)— | α-methylbenzyl |
| 468 | 2-methylphenyl | —C(=O)— | —C(=O)O— | α-methylbenzyl |
| 469 | 2-methylphenyl | —C(=O)— | —C(=O)NH— | α-methylbenzyl |
| 470 | 2-methylphenyl | —C(=O)— | —SO₂— | α-methylbenzyl |
| 471 | 2-methylphenyl | —C(=O)— | —C(=O)— | methylphenyl |
| 472 | 2-methylphenyl | —C(=O)— | —C(=S)— | methylphenyl |
| 473 | 2-methylphenyl | —C(=O)— | —C(=O)O— | methylphenyl |
| 474 | 2-methylphenyl | —C(=O)— | —C(=O)NH— | methylphenyl |

TABLE 1-continued individual compounds of formula I according to the invention

| Compound No. | R¹ | A | Q | R⁹ |
|---|---|---|---|---|
| 475 | 2-methylphenyl | —C(=O)— | —SO₂— | 2-methylphenyl |
| 476 | 2-methylphenyl | —CH₂SO₂— | —C(=O)— | (1S)-1,2,3,4-tetrahydronaphthalen-1-yl |
| 477 | 2-methylphenyl | —CH₂SO₂— | —C(=S)— | (1S)-1,2,3,4-tetrahydronaphthalen-1-yl |
| 478 | 2-methylphenyl | —CH₂SO₂— | —C(=O)O— | (1S)-1,2,3,4-tetrahydronaphthalen-1-yl |
| 479 | 2-methylphenyl | —CH₂SO₂— | —C(=O)NH— | (1S)-1,2,3,4-tetrahydronaphthalen-1-yl |
| 480 | 2-methylphenyl | —CH₂SO₂— | —SO₂— | (1S)-1,2,3,4-tetrahydronaphthalen-1-yl |
| 481 | 2-methylphenyl | —CH₂SO₂— | —C(=O)— | 2-chloro-6-methylphenol |
| 482 | 2-methylphenyl | —CH₂SO₂— | —C(=S)— | 2-chloro-6-methylphenol |
| 483 | 2-methylphenyl | —CH₂SO₂— | —C(=O)O— | 2-chloro-6-methylphenol |

TABLE 1-continued
individual compounds of formula I according to the invention
| Compound No. | R¹ | A | Q | R⁹ |
|---|---|---|---|---|
| 484 | 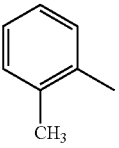 | —CH₂SO₂— | —C(=O)NH— | 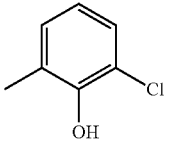 |
| 485 | 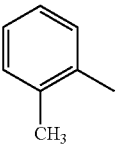 | —CH₂SO₂— | —SO₂— | 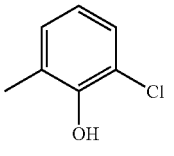 |
| 486 | 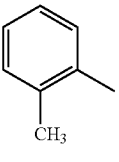 | —CH₂SO₂— | —C(=O)— | 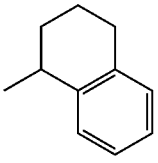 |
| 487 | 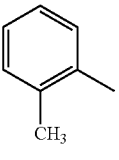 | —CH₂SO₂— | —C(=S)— | 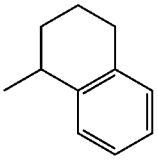 |
| 488 | 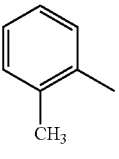 | —CH₂SO₂— | —C(=O)O— | 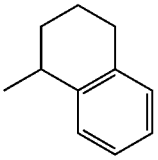 |
| 489 | 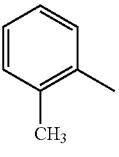 | —CH₂SO₂— | —C(=O)NH— | 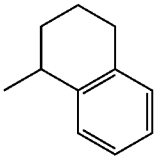 |
| 490 | 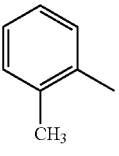 | —CH₂SO₂— | —SO₂— | 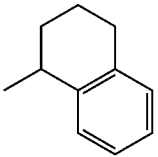 |
| 491 | 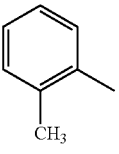 | —CH₂SO₂— | —C(=O)— | 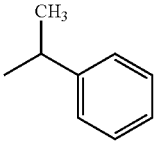 |
| 492 | 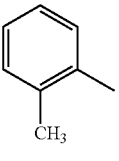 | —CH₂SO₂— | —C(=S)— | 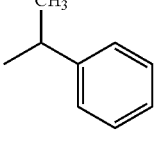 |

TABLE 1-continued individual compounds of formula I according to the invention

| Compound No. | R¹ | A | Q | R⁹ |
|---|---|---|---|---|
| 493 | 2-methylphenyl | —CH₂SO₂— | —C(=O)O— | 1-phenylethyl |
| 494 | 2-methylphenyl | —CH₂SO₂— | —C(=O)NH— | 1-phenylethyl |
| 495 | 2-methylphenyl | —CH₂SO₂— | —SO₂— | 1-phenylethyl |
| 496 | 2-methylphenyl | —CH₂SO₂— | —C(=O)— | benzyl |
| 497 | 2-methylphenyl | —CH₂SO₂— | —C(=S)— | benzyl |
| 498 | 2-methylphenyl | —CH₂SO₂— | —C(=O)O— | benzyl |
| 499 | 2-methylphenyl | —CH₂SO₂— | —C(=O)NH— | benzyl |
| 500 | 2-methylphenyl | —CH₂SO₂— | —SO₂— | benzyl |
| 501 | 3-CF₃-1,5-dimethyl-1H-pyrazol-4-yl | —CH₂C(=O)— | —C(=O)— | 2-fluoro-6-methylphenol-yl |

TABLE 1-continued individual compounds of formula I according to the invention

| Compound No. | R¹ | A | Q | R⁹ |
|---|---|---|---|---|
| 502 | 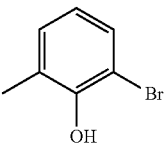 CF₃, pyrazole-N-CH₃, CH₃ | —CH₂C(=O)— | —C(=O)— | 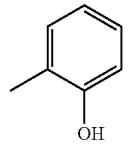 2-Br, 6-methyl phenol |
| 503 | CF₃, pyrazole-N-CH₃, CH₃ | —CH₂C(=O)— | —C(=O)— | 2-methyl phenol, OH |
| 504 | CF₃, pyrazole-N-CH₃, CH₃ | —CH₂C(=O)— | —C(=O)— | 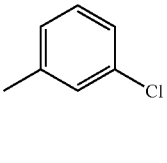 3-Cl, methyl phenyl |
| 505 | CF₃, pyrazole-N-CH₃, CH₃ | —CH₂C(=O)— | —C(=O)— | 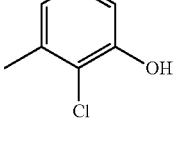 2-Cl, 3-methyl phenol |
| 506 | CF₃, pyrazole-N-CH₃, CH₃ | —CH₂C(=O)— | —C(=O)— | 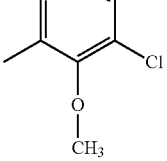 2-Cl, 6-methyl, OCH₃ phenyl |
| 507 | CF₃, pyrazole-N-CH₃, CH₃ | —CH₂C(=O)— | —C(=O)— | 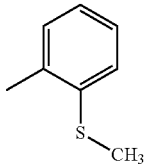 2-methyl phenyl-SCH₃ |
| 508 | CF₃, pyrazole-N-CH₃, CH₃ | —CH₂C(=O)— | —C(=O)— | 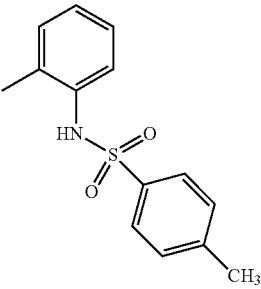 2-methyl phenyl-NH-SO₂-(4-methylphenyl) |

TABLE 1-continued
individual compounds of formula I according to the invention
| Compound No. | R¹ | A | Q | R⁹ |
|---|---|---|---|---|
| 509 | 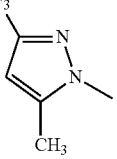 | —CH₂C(=O)— | —C(=O)— | 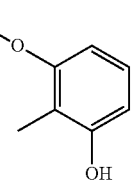 |
| 510 | 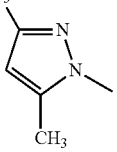 | —CH₂C(=O)— | —C(=O)— | 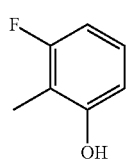 |
| 511 | 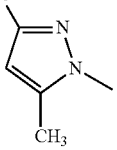 | —CH₂C(=O)— | —C(=O)— | 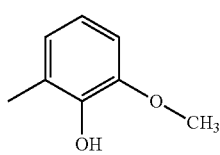 |
| 512 | 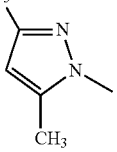 | —CH₂C(=O)— | —C(=O)— | 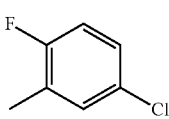 |
| 513 | 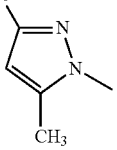 | —CH₂C(=O)— | —C(=O)— | 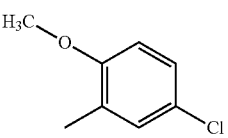 |
| 514 | 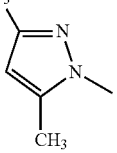 | —CH₂C(=O)— | —C(=O)— | 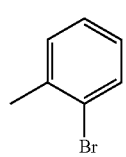 | where
a) 514 compounds of formula (I.a):

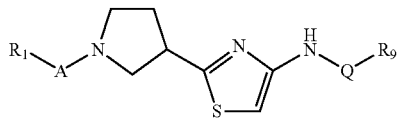
(I.a)

wherein A, Q, R¹ and R⁹ are as defined in Table 1.
b) 514 compounds of formula (I.b):

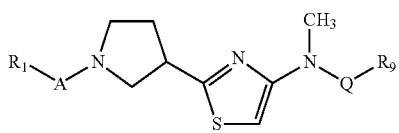
(I.b)

wherein A, Q, R¹ and R⁹ are as defined in Table 1.
c) 514 compounds of formula (I.c):

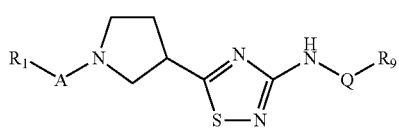
(I.c)

wherein A, Q, R¹ and R⁹ are as defined in Table 1.
d) 514 compounds of formula (I.d):

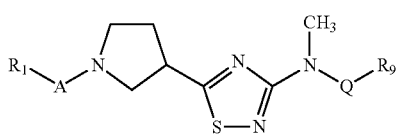
(I.d)

wherein A, Q, R¹ and R⁹ are as defined in Table 1.
e) 514 compounds of formula (I.e):

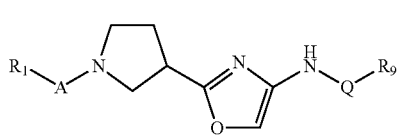
(I.e)

wherein A, Q, R¹ and R⁹ are as defined in Table 1.
f) 514 compounds of formula (I.f):

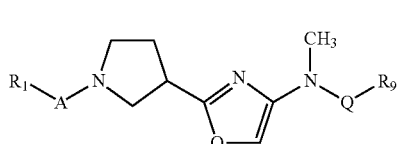
(I.f)

wherein A, Q, R¹ and R⁹ are as defined in Table 1.

g) 514 compounds of formula (I.g):

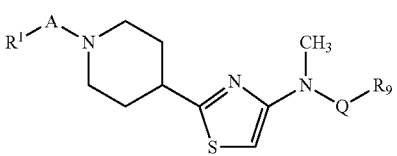
(I.g)

wherein A, Q, R¹ and R⁹ are as defined in Table 1.
h) 514 compounds of formula (I.h):

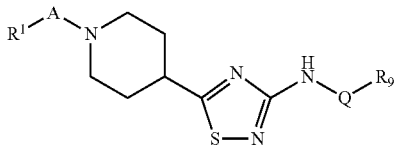
(I.h)

wherein A, Q, R¹ and R⁹ are as defined in Table 1.
i) 514 compounds of formula (I.i):

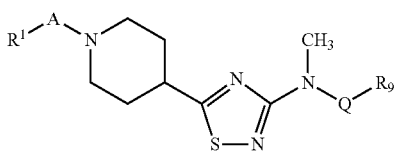
(I.i)

wherein A, Q, R¹ and R⁹ are as defined in Table 1.
j) 514 compounds of formula (I.j):

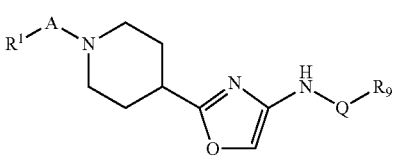
(I.j)

wherein A, Q, R¹ and R⁹ are as defined in Table 1.
k) 514 compounds of formula (I.k):

(I.k)

wherein A, Q, R¹ and R⁹ are as defined in Table 1.

m) 514 compounds of formula (I.m):

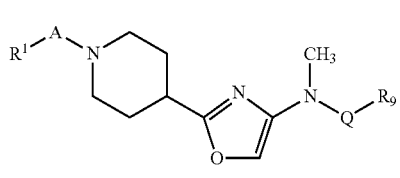
(I.m)

wherein A, Q, R¹ and R⁹ are as defined in Table 1.

n) 514 compounds of formula (I.n):

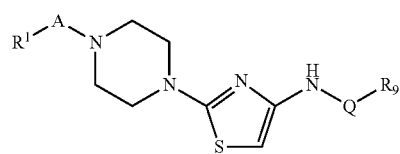
(I.n)

wherein A, Q, R¹ and R⁹ are as defined in Table 1.

o) 514 compounds of formula (I.o):

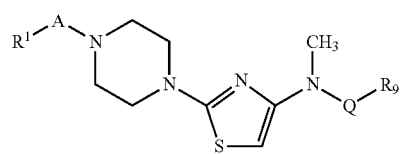
(I.o)

wherein A, Q, R¹ and R⁹ are as defined in Table 1.

p) 514 compounds of formula (I.p):

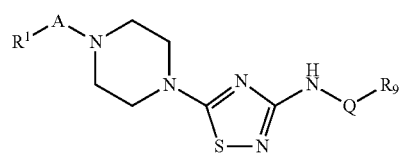
(I.p)

wherein A, Q, R¹ and R⁹ are as defined in Table 1.

q) 514 compounds of formula (I.q):

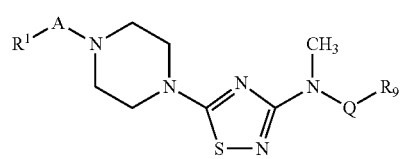
(I.q)

wherein A, Q, R¹ and R⁹ are as defined in Table 1.

r) 514 compounds of formula (I.r):

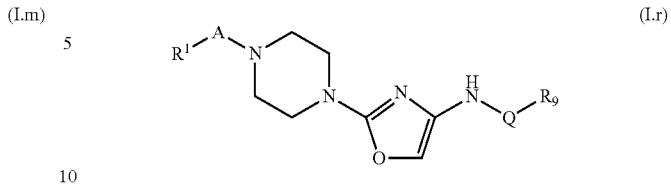
(I.r)

wherein A, Q, R¹ and R⁹ are as defined in Table 1.

s) 514 compounds of formula (I.s):

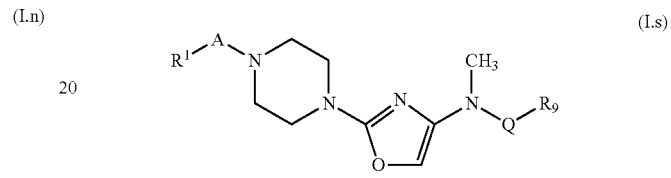
(I.s)

wherein A, Q, R¹ and R⁹ are as defined in Table 1.

t) 514 compounds of formula (I.t):

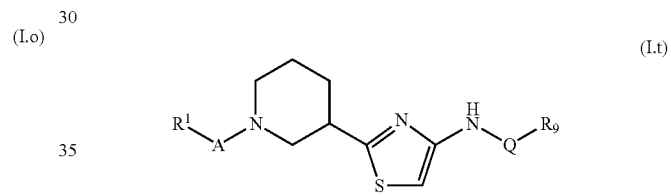
(I.t)

wherein A, Q, R¹ and R⁹ are as defined in Table 1.

u) 514 compounds of formula (I.u):

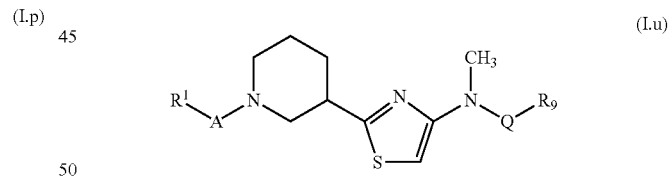
(I.u)

wherein A, Q, R¹ and R⁹ are as defined in Table 1.

v) 514 compounds of formula (I.v):

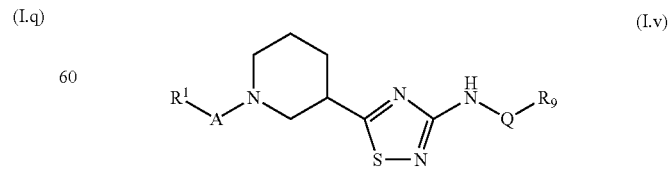
(I.v)

wherein A, Q, R¹ and R⁹ are as defined in Table 1.

w) 514 compounds of formula (I.w):

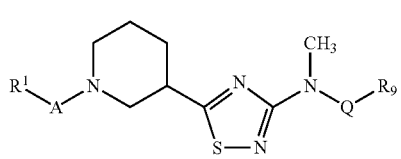
(I.w)

wherein A, Q, R$^1$ and R$^9$ are as defined in Table 1.
x) 514 compounds of formula (I.x):

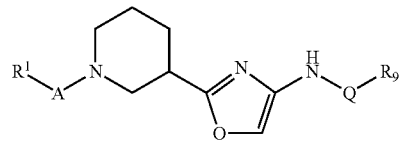
(I.x)

wherein A, Q, R$^1$ and R$^9$ are as defined in Table 1.
y) 514 compounds of formula (I.y):

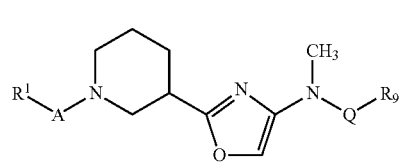
(I.y)

wherein A, Q, R$^1$ and R$^9$ are as defined in Table 1.

Throughout this description, temperatures are given in degrees Celsius and "m.p." means melting point. LC/MS means Liquid Chromatography Mass Spectroscopy and the description of the apparatus and the method is: (HP 1100 HPLC from Agilent, Phenomenex Gemini C18, 3 µm particle size, 110 Angström, 30×3 mm column, 1.7 mL/min., 60° C., H$_2$O+0.05% HCOOH (95%)/CH$_3$CN/MeOH 4:1+0.04% HCOOH (5%)–2 min.–CH$_3$CN/MeOH 4:1+0.04% HCOOH (5%)–0.8 min., ZQ Mass Spectrometer from Waters, ionization method: electrospray (ESI), Polarity: positive ions, Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400)).

Table 2 shows selected m.p. data and selected LC/MS data for compounds of Table 1.

TABLE 2

Melting point and LC/MS data for compounds of Table 1

| Compound No. | Melting point (° C.) | LC/MS |
|---|---|---|
| I.g.001 | 175 | |
| I.g.006 | | Rt = 3.27 min.; MS: m/z = 527 (M + 1) |
| I.g.011 | 179-181 | |
| I.g.013 | | Rt = 2.02 min.; MS: m/z = 570 (M + 23) |
| I.g.016 | | Rt = 1.9 min.; MS: m/z = 506 (M + 1) |
| I.g.018 | | Rt = 1.91 min.; MS: m/z = 522 (M + 23) |
| I.g.021[1] | | Rt = 2.77 min; MS: m/z = 478 (M + 1) |
| I.g.023 | 154-156 | Rt = 1.94 min; MS: m/z = 508 (M + 1) |
| I.g.024 | | Rt = 1.85 min; MS: m/z = 494 (M + 1) |
| I.g.025[1] | | Rt = 2.75 min; MS: m/z = 514 (M + 1) |

TABLE 2-continued

Melting point and LC/MS data for compounds of Table 1

| Compound No. | Melting point (° C.) | LC/MS |
|---|---|---|
| I.g.136 | | Rt = 2.01 min; MS: m/z = 488 (M + 1) |
| I.g.141 | | Rt = 1.98 min; MS: m/z = 462 (M + 1) |
| I.g.196 | | Rt = 2.17 min; MS: m/z = 490 (M + 1) |
| I.g.211 | 233-234 | |
| I.g.246 | 173-175 | |
| I.g.386 | 174-175 | |
| I.g.501 | | Rt = 1.88 min; MS: m/z = 512 (M + 1) |
| I.g.502 | 193-195 | |
| I.g.503 | | Rt = 1.85 min; MS: m/z = 494 (M + 1) |
| I.g.504 | | Rt = 1.95 min; MS: m/z = 512 (M + 1) |
| I.g.505 | | Rt = 1.70 min; MS: m/z = 528(M + 1) |
| I.g.506 | | Rt = 1.97 min; MS: m/z = 542 (M + 1) |
| I.g.507 | | Rt = 1.85 min; MS: m/z = 524 (M + 1) |
| I.g.508 | | Rt = 1.98 min; MS: m/z = 647 (M + 1) |
| I.g.509 | | Rt = 2.03 min; MS: m/z = 524 (M + 1) |
| I.g.510 | | Rt = 1.94 min; MS: m/z = 512 (M + 1) |
| I.g.511 | | Rt = 1.85 min; MS: m/z = 524 (M + 1) |
| I.g.512 | | Rt = 1.96 min; MS: m/z = 530 (M + 1) |
| I.g.513 | | Rt = 2.03 min; MS: m/z = 542 (M + 1) |
| I.g.514 | | Rt = 1.86 min; MS: m/z = 558 (M + 2) |
| I.h.011 | | Rt = 1.90 min; MS: m/z = 546 (M + 1) |
| I.n.011 | 207-209 | |
| I.n.021 | | Rt = 1.78 min; MS: m/z = 479 (M + 1) |
| I.n. 023 | | Rt = 1.83 min; MS: m/z = 495 (M + 1) |
| I.n. 024 | 175-178 | |

The compounds according to the present invention can be prepared according to the above-mentioned reaction schemes, in which, unless otherwise stated, the definition of each variable is as defined above for a compound of formula (I).

BIOLOGICAL EXAMPLES

*Phytophthora infestans*/Tomato/Leaf Disc Preventative (Tomato Late Blight)

Tomato leaf disks are placed on water agar in multiwell plates (24-well format) and sprayed with the formulated test compound diluted in water. The leaf disks are inoculated with a spore suspension of the fungus 1 day after application. The inoculated leaf disks are incubated at 16° C. and 75% rh under a light regime of 24 h darkness followed by 12 h light/12 h darkness in a climate cabinet and the activity of a compound is assessed as percent disease control compared to untreated when an appropriate level of disease damage appears in untreated check leaf disks (5-7 days after application).

Compounds I.g.001, I.g.006, I.g.011, I.g.013, I.g.016, I.g.018, I.g.021, I.g.023, I.g.024, I.g.136, I.g.386, I.g.501, I.g.503, I.g.506, I.g.508, I.g.509, I.g.510, I.g.511, I.h.011, I.n.011 and I.n.021 at 200 ppm give at least 80% disease control in this test when compared to untreated control leaf disks under the same conditions, which show extensive disease development.

*Phytophthora infestans*/Potato/Preventative (Potato Late Blight)

2-week old potato plants cv. Bintje are sprayed in a spray chamber with the formulated test compound diluted in water. The test plants are inoculated by spraying them with a sporangia suspension 2 days after application. The inoculated test plants are incubated at 18° C. with 14 h light/day and 100% rh in a growth chamber and the percentage leaf area covered by disease is assessed when an appropriate level of disease appears on untreated check plants (5-7 days after application).

Compounds I.g.001, I.g.006, I.g.011, I.g.016, I.g.023, I.g.024, I.g.136, I.g.501, I.g.502 and I.g.511 at 200 ppm give at least 80% disease control in this test when compared to untreated control leaf disks under the same conditions, which show extensive disease development.

*Phytophthora infestans*/Potato/Long Lasting (Potato Late Blight)

2-week old potato plants cv. Bintje are sprayed in a spray chamber with the formulated test compound diluted in water. The test plants are inoculated by spraying them with a sporangia suspension 6 days after application. The inoculated test plants are incubated at 18° C. with 14 h light/day and 100% rh in a growth chamber and the percentage leaf area covered by disease is assessed when an appropriate level of disease appears on untreated check plants (9-11 days after application).

Compounds I.g.001, I.g.006, I.g.011, I.g.016, I.g.023, I.g.024, I.g.501 and I.g.502 at 200 ppm give at least 80% disease control in this test when compared to untreated control leaf disks under the same conditions, which show extensive disease development.

*Phytophthora infestans*/Potato/Curative (Potato Late Blight)

2-week old potato plants cv. Bintje are inoculated by spraying them with a sporangia suspension one day before application. The inoculated plants are sprayed in a spray chamber with the formulated test compound diluted in water. The inoculated test plants are incubated at 18° C. with 14 h light/day and 100% rh in a growth chamber and the percentage leaf area covered by disease is assessed when an appropriate level of disease appears on untreated check plants (3-4 days after application).

Compounds I.g.001, I.g.011 and I.g.023 at 200 ppm give at least 80% disease control in this test when compared to untreated control leaf disks under the same conditions, which show extensive disease development.

*Plasmopara viticola*/Grape/Leaf Disc Preventative (Grape Downy Mildew)

Grape vine leaf disks are placed on water agar in multiwell plates (24-well format) and sprayed with the formulated test compound diluted in water. The leaf disks are inoculated with a spore suspension of the fungus 1 day after application. The inoculated leaf disks are incubated at 19° C. and 80% rh under a light regime of 12 h light/12 h darkness in a climate cabinet and the activity of a compound is assessed as percent disease control compared to untreated when an appropriate level of disease damage appears in untreated check leaf disks (6-8 days after application).

Compounds I.g.001, I.g.011, I.g.013, I.g.016, I.g.018, I.g.021, I.g.023, I.g.024, I.g.246 I.g.386, I.g.501, I.g.503, I.g.506, I.g.508, I.g.509, I.g.510, I.n.011 and I.n.021 at 200 ppm give at least 80% disease control in this test when compared to untreated control leaf disks under the same conditions, which show extensive disease development.

*Plasmopara viticola*/Grape/Preventative (Grape Downy Mildew)

5-week old grape seedlings cv. Gutedel are sprayed in a spray chamber with the formulated test compound diluted in water. The test plants plants are inoculated by spraying a sporangia suspension on their lower leaf surface one day after application. The inoculated test plants are incubated at 22° C. and 100% rh in a greenhouse and the percentage leaf area covered by disease is assessed when an appropriate level of disease appears on untreated check plants (6-8 days after application).

Compounds I.g.001, I.g.006, I.g.011, I.g.016, I.g.023 and I.g.024, I.g.501, I.g.502 and I.g.503 at 200 ppm give at least 80% disease control in this test when compared to untreated control leaf disks under the same conditions, which show extensive disease development.

*Plasmopara viticola*/Grape/Long Lasting (Grape Downy Mildew)

5-week old grape seedlings cv. Gutedel are sprayed in a spray chamber with the formulated test compound diluted in water. The test plants are inoculated by spraying a sporangia suspension on their lower leaf surface 6 days after application. The inoculated test plants are incubated at 22° C. and 100% rh in a greenhouse and the percentage leaf area covered by disease is assessed when an appropriate level of disease appears on untreated check plants (11-13 days after application).

Compounds I.g.001, I.g.006, I.g.011, I.g.023 and I.g.024, I.g.501 and I.g.502 at 200 ppm give at least 80% disease control in this test when compared to untreated control leaf disks under the same conditions, which show extensive disease development.

*Plasmopara viticola*/Grape/Curative (Grape Downy Mildew)

5-week-old grape seedlings cv. Gutedel are inoculated by spraying a sporangia suspension on their lower leaf surface one day before application. The inoculated grape plants are sprayed in a spray chamber with the formulated test compound diluted in water. The inoculated test plants are incubated at 22° C. and 100% rh in a greenhouse and the percentage leaf area covered by disease is assessed when an appropriate level of disease appears on untreated check plants (4-6 days after application).

Compounds I.g.001, I.g.006, I.g.011 and I.g.023 at 200 ppm give at least 80% disease control in this test when compared to untreated control leaf disks under the same conditions, which show extensive disease development.

*Pythium ultimum*/Liquid Culture (Seedling Damping Off)

Mycelia fragments and oospores of a newly grown liquid culture of the fungus are directly mixed into nutrient broth (PDB potato dextrose broth). After placing a (DMSO) solution of test compound into a microtiter plate (96-well format), the nutrient broth containing the fungal mycelia/spore mixture is added. The test plates are incubated at 24° C. and the inhibition of growth is determined photometrically 2-3 days after application.

Compounds I.g.006, I.g.501, I.g.502, I.g.503 and I.g.511 at 200 ppm give at least 80% disease control in this test when compared to untreated control leaf disks under the same conditions, which show extensive disease development.

*Pythium ultimum*/Cotton/Soil Drench (Seedling Damping Off)

The test is carried out in plastic containers (650 ml volume) using a mixture of (50% Vermiculit+sterile 50% Cugy soil)+10% v/v water. 10 seeds (cotton, cv. Sure Grow 747) are sown in 2 rows of 5 seeds per container (3 replicates for evaluation of the activity, 3 replicates for evaluation of phytotox). Application is carried out directly after sowing by pouring 10 ml compound diluted in water per row over the seeds. Just afterwards the seeds are covered with a thin layer of the same soil and the inoculation is happening. *Pythium ultimum* is cultivated for 14 days on carrot slices in Roux bottles. For inoculation, the content of the Roux bottles is mixed and homogenously dispensed over the plastic containers without further filtering (70 ml suspension per container). Incubation conditions: 20° C., 12 h/12 h day/night period in the greenhouse. The activity of a compound is assessed as percent disease control relative to untreated check plants when an appropriate level of disease damage appears in untreated check plants (13-16 days after application).

Compounds I.g.006, I.g.501, I.g.502 and I.g.511 at 200 ppm give at least 80% disease control in this test when compared to untreated control leaf disks under the same conditions, which show extensive disease development.

What is claimed is:
1. A compound of formula I:

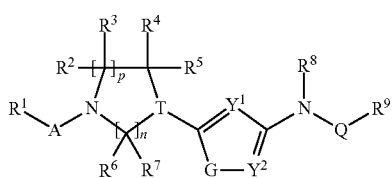

(I)

wherein
A is x-C(=O)—, x-C(=S)—, x-C($R^{10}R^{11}$)—C(=O)—, x-C($R^{12}R^{13}$)—C(=S)—, x-O—C(=O)—, x-O—C(=S)—, x-N($R^{14}$)—C(=O)—, x-N($R^{15}$)—C(=S)—, x-C($R^{16}R^{17}$)—$SO_2$— or x-N=C($R^{26}$)—, in each case x indicates the bond that is connected to $R^1$;
T is $CR^{18}$ or N;
G is O or S;
$Y^1$ and $Y^2$ are independently $CR^{19}$ or N;
Q is —C(=O)-z, —C(=S)-z, —C(=O)—O-z, —C(=S)—O-z, —C(=O)—N($R^{20}$)-z, —C(=S)—N($R^{21}$)-z or —$SO_2$-z-, in each case z indicates the bond that is connected to $R^9$;
n is 1 or 2;
p is 1 or 2, providing that when n is 2, p is 1;
$R^1$ is phenyl, pyridyl, imidazolyl, or pyrazolyl; wherein the phenyl, pyridyl, imidazolyl and pyrazolyl are each optionally substituted by 1 to 3 substituents independently selected from $C_1$-$C_4$ alkyl, $C_1$-$C_4$ haloalkyl, halogen, cyano, hydroxy and amino;
$R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$, $R^{19}$ and $R^{26}$ each independently are hydrogen, halogen, cyano, $C_1$-$C_4$ alkyl or $C_1$-$C_4$ haloalkyl;
$R^8$, $R^{14}$, $R^{15}$, $R^{20}$ and $R^{21}$ each independently are hydrogen, $C_1$-$C_4$ alkyl or $C_1$-$C_4$ alkoxy; and
$R^9$ is phenyl, benzyl or group (a):

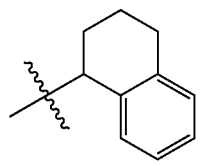

(a)

wherein the phenyl, benzyl and group (a) are each optionally substituted with 1 to 3 substituents independently selected from $C_1$-$C_4$ alkyl, $C_1$-$C_4$ haloalkyl, $C_1$-$C_4$ alkoxy, $C_1$-$C_4$ haloalkoxy, halogen, cyano, hydroxyl, N($R^{27}$)$_2$, SH, $C_1$-$C_4$ alkylthio, nitro, phenylsulfonyl and phenylsulfinyl, wherein the phenylsulfonyl and phenylsulfinyl are optionally substituted by 1 to 3 substituents independently selected from $C_1$-$C_4$ alkyl, $C_1$-$C_4$ haloalkyl, $C_1$-$C_4$ alkoxy, $C_1$-$C_4$ haloalkoxy, halogen and cyano;
each $R^{27}$ independently is hydrogen, $C_1$-$C_4$ alkyl, phenylsulfonyl or phenylsulfinyl, wherein the phenylsulfonyl and phenylsulfinyl are optionally substituted by 1 to 3 substituents independently selected from $C_1$-$C_4$ alkyl, $C_1$-$C_4$ haloalkyl, $C_1$-$C_4$ alkoxy, $C_1$-$C_4$ haloalkoxy, halogen and cyano;
or a salt or a N-oxide thereof.

2. The compound according to claim 1, wherein
A is x-C(=O)—, x-C(=S)—, x-C($R^{10}R^{11}$)—C(=O)—, x-C($R^{12}R^{13}$)—C(=S)—, x-O—C(=O)—, x-O—C(=S)—, x-N($R^{14}$)—C(=O)—, x-N($R^{15}$)—C(=S)— or x-C($R^{16}R^{17}$)—$SO_2$—, in each case x indicates the bond that is connected to $R^1$;
T is $CR^{18}$ or N;
G is O or S;
$Y^1$ and $Y^2$ are independently $CR^{19}$ or N;
Q is —C(=O)-z, —C(=S)-z, —C(=O)—O-z, —C(=S)—O-z, —C(=O)—N($R^{20}$)-z, —C(=S)—N($R^{21}$)-z or —$SO_2$-z-, in each case z indicates the bond that is connected to $R^9$;
n is 1 or 2;
p is 1 or 2, providing that when n is 2, p is 1;
$R^1$ is phenyl, pyridyl, imidazolyl or pyrazolyl; wherein the phenyl, pyridyl, imidazolyl and pyrazolyl are each optionally substituted by 1 to 3 substituents independently selected from $C_1$-$C_4$ alkyl, $C_1$-$C_4$ haloalkyl, halogen, cyano, hydroxy and amino;
$R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$ and $R^{19}$ each independently are hydrogen, halogen, cyano, $C_1$-$C_4$ alkyl or $C_1$-$C_4$ haloalkyl;
$R^8$, $R^{14}$, $R^{15}$, $R^{20}$, and $R^{21}$ each independently are hydrogen or $C_1$-$C_4$ alkyl; and
$R^9$ is phenyl, benzyl or group (a):

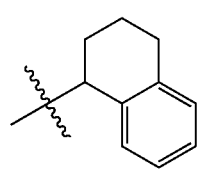

(a)

wherein the phenyl, benzyl and group (a) are each optionally substituted with 1 to 3 substituents independently selected from $C_1$-$C_4$ alkyl, $C_1$-$C_4$ haloalkyl, halogen, cyano, hydroxy and amino.

3. The compound according to claim 1, wherein
A is x-C(=O)—, x-C(=S)—, x-C($R^{10}R^{11}$)—C(=O)—, x-C($R^{12}R^{13}$)—C(=S)—, x-O—C(=O)—, x-O—C(=S)— or x-C($R^{16}R^{17}$)—$SO_2$—, in each case x indicates the bond that is connected to $R^1$;
T is $CR^{18}$ or N;
G is O or S;
$Y^1$ is N;
$y^2$ is $CR^{19}$ or N;
Q is —C(=O)-z, —C(=S)-z, —C(=O)—O-z, —C(=S)—O-z, —C(=O)—N($R^{20}$)-z, —C(=S)—N($R^{21}$)-z or —$SO_2$-z-, in each case z indicates the bond that is connected to $R^9$;
n is 1 or 2;
p is 1;
$R^1$ is phenyl or pyrazolyl; wherein the phenyl and pyrazolyl are each optionally substituted by 1 to 3 substituents independently selected from $C_1$-$C_4$ alkyl, $C_1$-$C_4$ haloalkyl, halogen, cyano, hydroxy, and amino;
$R^2$, $R^3$, $R^4$, $R^5$, $R^6$, $R^7$, $R^{10}$, $R^{11}$, $R^{12}$, $R^{13}$, $R^{16}$, $R^{17}$, $R^{18}$ and $R^{19}$ each independently are hydrogen, halogen, $C_1$-$C_4$ alkyl or $C_1$-$C_4$ haloalkyl;

$R^8$, $R^{20}$ and $R^{21}$ each independently are hydrogen or $C_1$-$C_4$ alkyl; and $R^9$ is phenyl, benzyl or group (a):

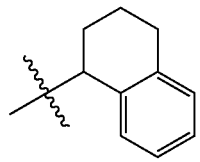
(a)

wherein the phenyl, benzyl and group (a) are each optionally substituted with 1 to 3 substituents independently selected from $C_1$-$C_4$ alkyl, $C_1$-$C_4$ haloalkyl, halogen, cyano, hydroxy and amino.

4. The compound according to claim 1, wherein
A is x-C(=O)—, -x-CR$^{10}$R$^{11}$—C(=O)—, x-O—C(=O)— or x-C(R$^{16}$R$^{17}$)—SO$_2$—, in each case x indicates the bond that is connected to R$^1$;
T is CR$^{18}$ or N;
G is S;
Y$^1$ is N;
y$^2$ is CR$^{19}$ or N;
Q is —C(=O)-z, —C(=O)—O-z, —C(=O)—N(R$^{20}$)-z or —SO$_2$-z-, in each case z being the bond to R$^9$;
n is 1 or 2;
p is 1;
R$^1$ is phenyl or pyrazolyl, wherein the phenyl and pyrazolyl are each optionally substituted with 1 to 3 substituents independently selected from $C_1$-$C_4$ alkyl, $C_1$-$C_4$ haloalkyl and halogen;
R$^2$, R$^3$, R$^4$, R$^5$, R$^6$, R$^7$, R$^{10}$, R$^{11}$, R$^{16}$, R$^{17}$, R$^{18}$, and R$^{19}$ each independently are hydrogen, fluoro or methyl;
R$^8$ and R$^{20}$ each independently are hydrogen or methyl; and
R$^9$ is phenyl, benzyl or group (a):

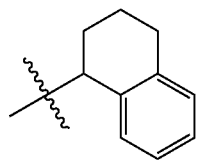
(a)

wherein the phenyl, benzyl and group (a) are each optionally substituted with 1 to 3 substituents independently selected from $C_1$-$C_4$ alkyl, $C_1$-$C_4$ haloalkyl, hydroxy and halogen.

5. The compound according to claim 1, wherein
A is x-C(=O)—, x-CH$_2$—C(=O)—, x-O—C(=O)— or x-CH$_2$—SO$_2$—, in each case x indicates the bond that is connected to R$^1$;
T is CH or N;
G is S;
Y$^1$ is N;
y$^2$ is CH or N;
Q is —C(=O)-z, —C(=O)—O-z, —C(=O)—NH-z or —SO$_2$-z-, in each case z indicates the bond that is connected to R$^9$;
n is 1 or 2;
p is 1;

R$^1$ is phenyl or group (b):

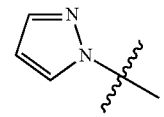
(b)

wherein the phenyl and group (b) are optionally substituted with 1 to 3 substituents independently selected from halogen, $C_1$-$C_4$ alkyl and $C_1$-$C_4$ haloalkyl;
R$^2$, R$^3$, R$^4$, R$^5$, R$^6$ and R$^7$ are each hydrogen;
R$^8$ is hydrogen; and
R$^9$ is phenyl, benzyl or group (a):

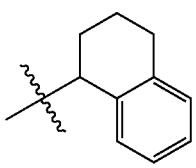
(a)

wherein the phenyl, benzyl and group (a) are each optionally substituted with 1 to 3 substituents independently selected from $C_1$-$C_4$ alkyl, $C_1$-$C_4$ haloalkyl, hydroxy and halogen.

6. The compound according to claim 1, wherein
A is x-CH$_2$—C(=O)— wherein x indicates the bond that is connected to R$^1$;
T is CH;
G is S;
Y$^1$ is N;
y$^2$ is CH;
Q is —C(=O)-z, —C(=O)—O-z or C(=O)—N(R$^{20}$)-z, in each case z indicates the bond that is connected to R$^9$;
n is 2;
p is 1;
R$^1$ is selected from group (c) or (d):

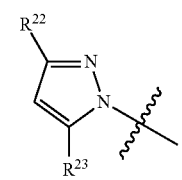
(c)

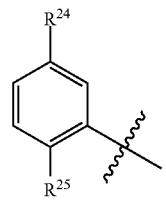
(d)

wherein R$^{22}$, R$^{23}$, R$^{24}$ and R$^{25}$ are independently selected from hydrogen, halogen, methyl and halomethyl;
R$_2$, R$_3$, R$_4$, R$_5$, R$_6$, and R$_7$ are each hydrogen;
R$_8$, is hydrogen;

$R^9$ is phenyl, benzyl or group (a):

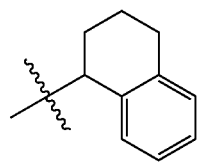

(a)

wherein the phenyl, benzyl and group (a) are optionally substituted with 1 to 3 substituents independently selected from halogen, hydroxy, methyl and halomethyl.

7. The compound according to claim 1, wherein G is S, $Y^1$ is N and $Y^2$ is CH.

8. The compound according to claim 1, wherein p is 1 and n is 2.

9. The compound according to claim 1, wherein $R^2$, $R^3$, $R^4$, $R^5$, $R^6$ and $R^7$ are H.

10. The compound according to claim 1, wherein Q is —C(=O)-z, wherein z indicates the bond that is connected to $R^9$.

11. The compound according to claim 1, wherein $R^9$ is phenyl substituted by hydroxy and optionally substituted by one or two further substituents.

12. The compound according to claim 11, wherein the hydroxy is at the ortho position.

13. A compound of formula I.a:

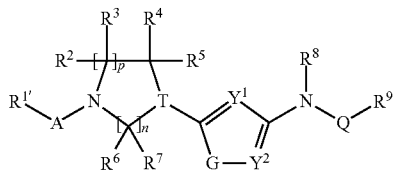

(I.a)

in which $R^{1'}$ is $C_1$-$C_8$ alkyl or a compound of formula II:

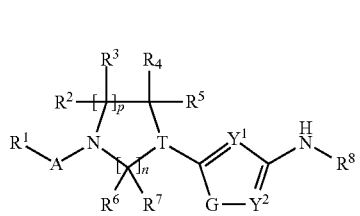

(II)

or a compound of formula VIII:

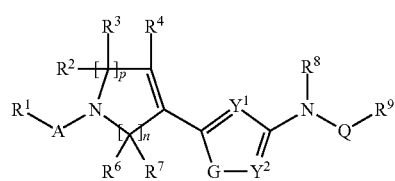

(VIII)

14. A fungicidal composition comprising at least one compound as defined in claim 1 and an agriculturally acceptable carrier, optionally comprising an adjuvant, and optionally comprising at least one additional fungicidally active compound.

15. A method of controlling an infestation of plants, propagation material thereof, harvested crops or non-living materials by phytopathogenic or spoilage microorganisms or organisms potentially harmful to man, which comprises the application of a compound as defined in claim 1, to the plant, to parts of the plants or to the locus thereof, to propagation material thereof or to any part of the non-living materials; wherein the phytopathogenic microorganisms are preferably fungal organisms.

* * * * *